(12) United States Patent
Asami et al.

(10) Patent No.: US 9,175,037 B2
(45) Date of Patent: Nov. 3, 2015

(54) NEUROMEDIN U DERIVATIVE

(75) Inventors: Taiji Asami, Fujisawa (JP); Hiroshi Inooka, Fujisawa (JP); Naoki Nishizawa, Fujisawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 620 days.

(21) Appl. No.: 13/263,630

(22) PCT Filed: Apr. 8, 2010

(86) PCT No.: PCT/JP2010/002588
§ 371 (c)(1),
(2), (4) Date: Dec. 27, 2011

(87) PCT Pub. No.: WO2010/116752
PCT Pub. Date: Oct. 14, 2010

(65) Prior Publication Data
US 2012/0094899 A1 Apr. 19, 2012

(30) Foreign Application Priority Data
Apr. 8, 2009 (JP) ................................ 2009-094000

(51) Int. Cl.
*A61K 38/00* (2006.01)
*C07K 7/06* (2006.01)
*C07K 7/02* (2006.01)

(52) U.S. Cl.
CPC ... *C07K 7/06* (2013.01); *C07K 7/02* (2013.01); *A61K 38/00* (2013.01)

(58) Field of Classification Search
None
See application file for complete search history.

(56) References Cited

U.S. PATENT DOCUMENTS

2010/0286035 A1  11/2010  Ohtaki et al.

FOREIGN PATENT DOCUMENTS

| WO | WO-2007/075439 A2 | 7/2007 | | |
|----|----|----|----|----|
| WO | WO 2007/109135 | * | 9/2007 | ............. C07K 14/43 |
| WO | WO-2007/109135 A2 | 9/2007 | | |
| WO | WO-2009/042053 A2 | 4/2009 | | |
| WO | WO-2009/044918 A1 | 4/2009 | | |

OTHER PUBLICATIONS

Ioannides-Demos et al., Drugs, 2005, 10, pp. 1391-1418.*
Mayo Clinic-Obesity Risk Factors, http://mayoclinic.com/health/obesity/DS00314, accessed Nov. 26, 2013.*
Lawlor et al., International Journal of Epidiology, 2006, 36, pp. 3-9.*
Pasut, G. et al., PEGylation of Proteins as Tailored Chemistry for Optimized Bioconjugates, Advances in Polymer Science, 2006, vol. 192, pp. 95-134.
Hashimoto, T. et al., Structure-Activity Relationships of Neuromedin U. II. Highly Potent Analogs Substituted or Modified at the N-Terminus of Neuromedin U-8[1,2], Chem. Pharm. Bull., 1995, vol. 43, No. 7, pp. 1154-1157.
Sakura, N. et al., Structure-Activity Relationships of Neuromedin U. I. Contractile Activity of Dog Neuromedin U-Related Peptides on Isolated Chicken Crop Smooth Muscle, Chem. Pharm. Bull., 1995, vol. 43, No. 7, pp. 1148-1153.
International Search Report for corresponding PCT/JP2010/002588.
Drug Delivery System, NOF Corporation, Catalogue version 10 (May 2008).

* cited by examiner

*Primary Examiner* — Karlheinz R Skowronek
*Assistant Examiner* — Roy Teller
(74) *Attorney, Agent, or Firm* — Mintz Levin Cohn Ferris Glovsky and Popeo, P.C.; David G. Conlin; George W. Neuner

(57) ABSTRACT

An object of the present invention is to provide a novel anorectic agent. Another object of the invention is to provide an NMU derivative which exhibits a high anorectic effect even when administered in a usual manner, for example, peripherally. These objects can be achieved by the compound represented by formula (I)

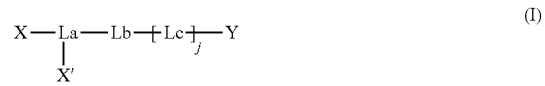

or a salt thereof. In formula (I), Y represents a polypeptide containing an amino acid sequence set forth in SEQ ID NO.: 1 wherein 1 to 4 amino acids are substituted; X represents a methoxypolyethylene glycol; X' is absent or represents a methoxypolyethylene glycol; and a moiety represented by formula:

La-Lb-[Lc]$_j$ represents a linker.

9 Claims, 9 Drawing Sheets

NEUROMEDIN U DERIVATIVE

CROSS-REFERENCE TO RELATED APPLICATIONS

This application is the national phase application pursuant to 35 U.S.C. §371 of International Application No. PCT/JP2010/002588, filed Apr. 8, 2010, which claims the benefit of priority of Japanese Patent Application No. 2009-094000, filed Apr. 8, 2009. These applications are hereby incorporated herein by reference in their entireties.

TECHNICAL FIELD

The present invention relates to a neuromedin U derivative.

BACKGROUND ART

Neuromedin U (NMU) was first isolated, as a peptide consisting of 25 amino acid residues or as a peptide consisting of 8 amino acid residues, from the pig small intestine using uterine smooth muscle contraction activity as an index. These peptides are named porcine NMU-25 or porcine NMU-8, based on the number of amino acid residues. Porcine NMU-8 is a cleavage product of porcine NMU-25 and consists of the C-terminal 8 residues of porcine NMU-25.

Similarly, NMU-25 is known in humans. The amino acid sequence of the C-terminal 8 residues of human NMU-25 is the same as that of the C-terminal 8 residues of porcine NMU-8.

Rat NMU consists of 23 amino acid residues, and is named NMU-23. The amino acid sequence of the C-terminal 8 residues of rat NMU-23 differs from that of the C-terminal 8 residues of porcine NMU-8 by one amino acid residue.

As a receptor for NMU, FM3, which is an orphan GPCR, was initially identified; subsequently, TGR1 was identified. Today, these receptors are called NMUR1 and NMUR2, respectively. FM3 is primarily distributed in the intestinal tract, whereas TGR1 is localized in the hypothalamus.

As a receptor for TGR1, a novel peptide has been isolated from rat brain. Since this peptide is localized in the suprachiasmatic nucleus within the hypothalamus, it was named neuromedin S (NMS), using the initial letter of the suprachiasmatic nucleus.

Human NMS consists of 33 amino acid residues, and the amino acid sequence of the C-terminal 8 amino acid residues are the same as the amino acid sequence of the C-terminal 8 residues of rat NMU-23.

NMUR1 and NMUR2 exhibit similar affinity to NMU, NMS, and NMU-8. It has been suggested that these receptors strongly recognize the amino acid sequence of the C-terminal 8 residues, the sequence of which is common to NMU and NMS.

An intracerebroventricular administration of rat NMU-23 in rats induces food intake suppression. A local injection of NMU to the paraventricular nucleus (PVN) or arcuate nucleus (ARC) has also been reported to induce an anorectic activity as in the case of its intracerebroventricular administration; therefore, the action sites of NMU are assumed to be PVN and ARC. Further, an intracerebroventricular administration of anti-NMU antibody has shown to increase food intake, suggesting that the central NMU produces physiological effects that suppress food intake. It has also been reported that NMU KO mice exhibited an obese phenotype, and that mice over-expressing NMU exhibited lower body weight and reduced food intake. This clarifies the physiological significance of endogenous NMU.

It has further been reported that an intracerebroventricular administration of NMU causes an elevation of body temperature, generation of heat, and elevation of oxygen consumption. These activities are assumed to be due to sympathetic activation of adipose tissue and muscle system.

It has also been reported that suppression of gastric acid secretion and suppression of gastric emptying are caused by an intracerebroventricular administration of NMU. These activities are assumed to be due to the central effects via CRH secretion. These activities result in reduced food intake.

It has not yet been examined in detail how a peripheral administration of NMU causes an action on the intestinal tract; however, considering that NMUR1 is expressed in the intestinal tract, it can be assumed that the peripheral administration of NMU causes a certain action on the intestinal tract. Based on this assumption, action on the stomach or intestinal tract caused by NMU peripheral administration was examined, and colon-specific prokinetic activity has been discovered.

Patent Literature (PTL) 1 and 2 disclose that an anorectic effect is achieved by peripheral administration of NMU.

The present inventors also discovered on their own accord that NMU-23 induces an anorectic activity via peripheral administration. In contrast, NMU-8 does not induce an anorectic activity via peripheral administration, although NMU-8 has a sufficiently strong agonist activity on the receptors, NMUR1 and NMUR2.

In order for a neuromedin U to be useful as an anorectic agent, it is very important that a neuromedin U induces a high anorectic activity even when administered in a usual manner, for example, peripherally.

As PEG derivatives, which are used for chemical modifications in the field of medicine, various compounds are known.

CITATION LIST

Patent Literature

PTL 1: WO 2007/075439
PTL 2: WO 2007/109135

SUMMARY OF INVENTION

Technical Problem

An object of the present invention is to provide a novel anorectic agent.

Another object of the present invention is to provide a novel neuromedin U derivative that exhibits a high anorectic effect even when administered in a usual manner, for example, peripherally.

Solution to Problem

The inventors of the present invention hypothesized that a cause for the absence of anorectic activity upon peripheral administration is instability of the NMU-8 in the blood. Further, the inventors inferred that a NMU-8 derivative (or a modified compound thereof) that is highly stable in the blood exhibits a sufficient anorectic activity.

Thus, the inventors prepared a neuromedin U derivative comprising a specific polypeptide which is produced by introducing substitution of 1 to 4 amino acid residues into an amino acid sequence consisting of 8 amino acids of the C-terminus of neuromedin U and to which a methoxypolyethylene glycol is bound via a linker. The inventors revealed that such a modified compound of NMU-8 exhibits a sufficiently strong anorectic effect and bodyweight reducing effect even when administered peripherally.

Based on this finding, the inventors continued their research, and completed the present invention.

More specifically, the present invention provides the following compounds defined in items [1] to [9], agents in items [10] and [11], method in item [12], and use in item [13].

[1] A compound represented by formula

(I)

[wherein Y represents a polypeptide consisting of an amino acid sequence set forth in SEQ ID NO.: 1 wherein 1 to 4 amino acids are substituted,
the amino acid substitution is selected from:
(1) substitution of Tyr at position 1 with Ala, Arg, Glu, Ser, Gln, NMeArg, Phe, NMeTyr, D-Tyr, Trp, or Pro;
(2) substitution of Phe at position 2 with Val, Gln, Arg, Glu, Ser, Tyr, Pro, Cha, Trp, NMePhe, Nle, Tyr(PO$_3$H$_2$), Hse, Nal(1), Nal(2), Phe(4F), or Aib;
(3) substitution of Leu at position 3 with Gln, Arg, Glu, Ser, Val, Phe, Pro, Thr, Cha, Nle, NMeArg, Ile, Leu(Me), Lys, NMeLeu, D-Leu, Ala, D-Ala, Gly, Abu, or Aib;
(4) substitution of Phe at position 4 with Gln, Leu, Pro, Cha, NMePhe, Trp, Phe(4F), Pya(4), αMePhe, Nle, Ala, or Aib;
(5) substitution of Arg at position 5 with Nle, Gln, NMeArg, Orn, Dbu, Pya(4), Hse, or Aib;
(6) substitution of Pro at position 6 with Ala, Hyp, NMeAla, MeGly, NMeSer, D-NMeAla, or Aib;
(7) substitution of Arg at position 7 with Arg(Me) or NMeArg; and
(8) substitution of Asn at position 8 with Nle, Gln, Arg, Asp, Pro, Abu, NMeAsn, or Aib;
X represents a methoxypolyethylene glycol;
X' is absent or represents a methoxypolyethylene glycol;
La is a divalent or trivalent group represented by formula

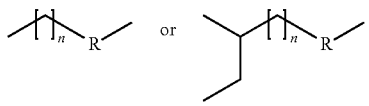

(wherein R represents a bond, —O—, —CO—O—, —O—CO—, —NH—, —CO—, —S—, —S—S—, —SO—, —SO$_2$—, —NH—SO$_2$—, —SO$_2$—NH—, —C(=O)—NH—N=CH—, —C(=NH)—NH—, —CO—CH$_2$—S—, or

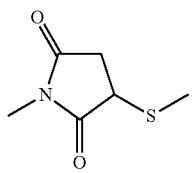

and
n is an integer of 0 to 5);
Lb represents —(CH$_2$)$_i$— (wherein i is an integer of 1 to 5);
Lc is a divalent group represented by formula (i):

—NH-Q$^c$-C$^b$ (wherein Q$^c$ is a divalent group represented by formula:

—(CH$_2$)$_{m1}$—Z$^c$—(CH$_2$)$_{m2}$—

(wherein m1 is an integer of 0 to 15,
Z$^c$ represents (a) a bond or (b) a divalent group selected from —CO—, —O—CO—, —CO—O—, —CO—NH—, —NH—CO—, —CO—NH—CO—, —NH—CO—NH—, —CH(NH$_2$)—, —CH(—NHR$^{zc1}$)—, —CH(R$^{zc2}$)—, —CH(OH)—, —CH(COOH)— —C(=NH)—, —S—, —S—S—, —SO—, —SO$_2$—, —NH—SO$_2$—, —SO$_2$—NH—,

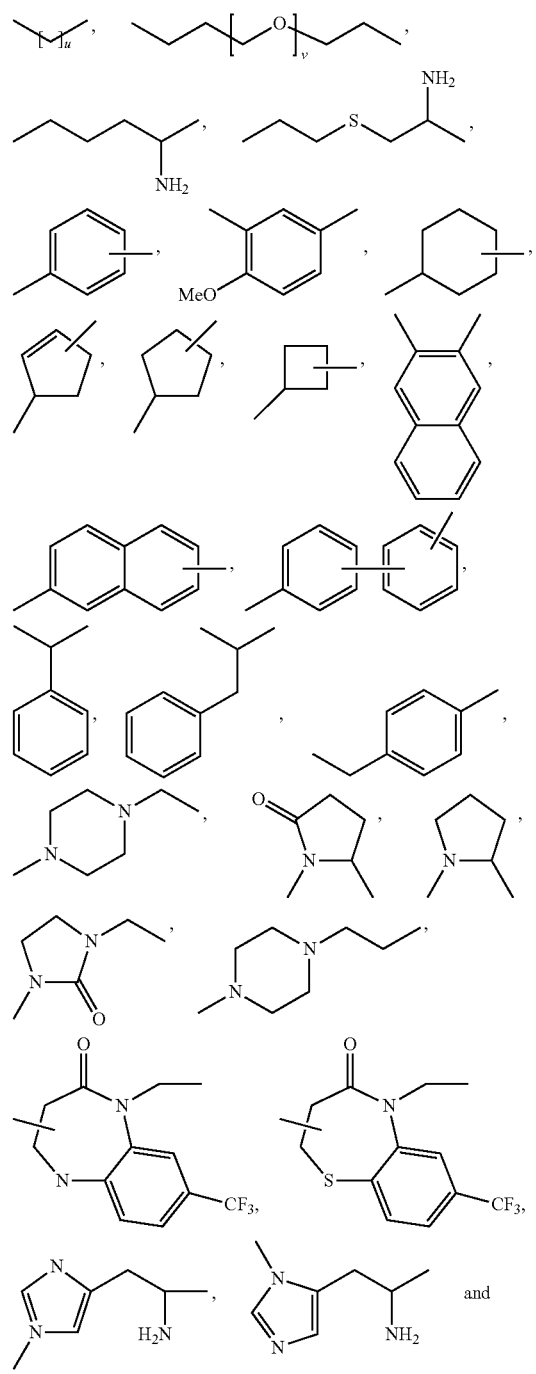

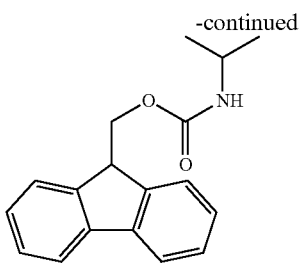

(wherein u is an integer of 1 to 18,
v is an integer of 1 to 12,
$R^{zc1}$ represents an amino-straight chain $C_{1-5}$ alkyl-carbonyl group, or an X-straight chain $C_{1-5}$ alkyl group (wherein X is as defined above), and
$R^{zc2}$ represents an amino-straight chain $C_{1-5}$ alkyl-carbonylamino-straight chain $C_{1-5}$ alkyl group), and
m2 is an integer of 0 to 15), and
$C^b$ represents a bond, —CO—, or —SO$_2$—), or
a divalent group represented by formula (ii):

-Q$^{c'}$-C$^{b'}$—

(wherein $Q^{c'}$ represents a divalent group selected from formula:

—(CH$_2$)$_{m1'}$—Z$^{c'}$—(CH$_2$)$_{m2'}$—

(wherein m1' is an integer of 0 to 15,
$Z^{c'}$ represents a divalent group selected from

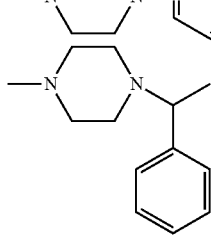

and m2' is an integer of 0 to 15), and
$C^{b'}$ represents —CO— or —SO$_2$—; and
j is an integer of 1 to 3]; or
a salt thereof.

[2] The compound of item [1] or a salt thereof, wherein the amino acid substitution is selected from:
(1) substitution of Tyr at position 1 with Ala, Arg, Glu, Ser, Gln, NMeArg, or Pro;
(2) substitution of Phe at position 2 with Val, Gln, Arg, Glu, Ser, Tyr, Pro, Cha, or Aib;
(3) substitution of Leu at position 3 with Gln, Arg, Glu, Ser, Val, Phe, Pro, Thr, Cha, Nle, NMeArg, or Aib;
(4) substitution of Phe at position 4 with Gln, Leu, Pro, Cha, NMePhe, or Aib;
(5) substitution of Arg at position 5 with Nle, Gln, NMeArg, or Aib;
(6) substitution of Pro at position 6 with Ala or Aib;
(7) substitution of Arg at position 7 with Arg(Me); and
(8) substitution of Asn at position 8 with Nle, Gln, Arg, Asp, Pro, or Aib.

[3] The compound of item [1] or a salt thereof, wherein the amino acid substitution is selected from:
(1) substitution of Tyr at position 1 with Arg, NMeArg, or Pro;
(2) substitution of Phe at position 2 with Gln;
(3) substitution of Leu at position 3 with Gln, Arg, Cha, NMeArg, or Val;
(4) substitution of Arg at position 5 with Gln or NMeArg; and
(5) substitution of Arg at position 7 with Arg(Me).

[4] The compound of item [1] or a salt thereof, wherein the amino acid substitution is selected from:
(1) substitution of Tyr at position 1 with Arg, Phe, NMeTyr, or Pro;
(2) substitution of Phe at position 2 with Glu, Tyr, Trp, or Nal(2);
(3) substitution of Leu at position 3 with Gln, Arg, Val, Cha, or NMeLeu;
(4) substitution of Phe at position 4 with Trp;
(5) substitution of Arg at position 5 with Gln or NMeArg;
(6) substitution of Pro at position 6 with Ala or NMeAla; and
(7) substitution of Arg at position 7 with Arg(Me) or NMeArg.

[5] The compound of item [1] or a salt thereof, wherein Y is a polypeptide consisting of an amino acid sequence selected from SEQ ID NOs.: 2 to 20.

[6] The compound of item [1] or a salt thereof, wherein the distance from the nitrogen atom closest to the Lb in the Lc to the nitrogen atom at the N-terminus of neuromedin U is 3.5 to 30 Å.

[7] The compound of item [1] or a salt thereof, wherein Lc is a divalent group represented by formula (i):

—NH-Q$^c$-C$^b$—

[wherein $Q^c$ is a divalent group represented by formula:

—(CH$_2$)$_{m1}$—

(wherein $m^1$ is an integer of 0 to 15), and
$C^b$ represents a bond, —CO—, or —SO$_2$—].

[8] The compound of item [1] or a salt thereof, wherein Lc is a divalent group represented by formula (i):

—NH-Q$^c$-C$^b$—

[wherein $Q^c$ represents a divalent group represented by formula:

—(CH$_2$)$_{m1}$—Z$^c$—(CH$_2$)$_{m2}$—

(wherein m1 is an integer of 0 to 10,
$Z^c$ is a divalent group selected from —CO—, —O—CO—, —CO—O—, —CO—NH—, —NH—CO—, —CO—NH—CO—, —NH—CO—NH—, —CH(NH$_2$)—, —CH(—NHR$^{zc1}$)—, —CH(R$^{zc2}$)—, —CH(OH)—, —CH(COOH)—, —C(=NH)—, —S—, —S—S—, —SO—, —SO$_2$—, —NH—SO$_2$—, —SO$_2$—NH—,

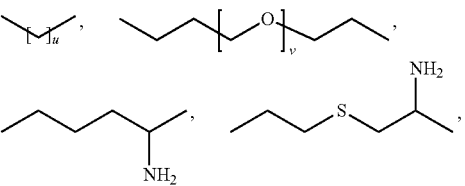

-continued

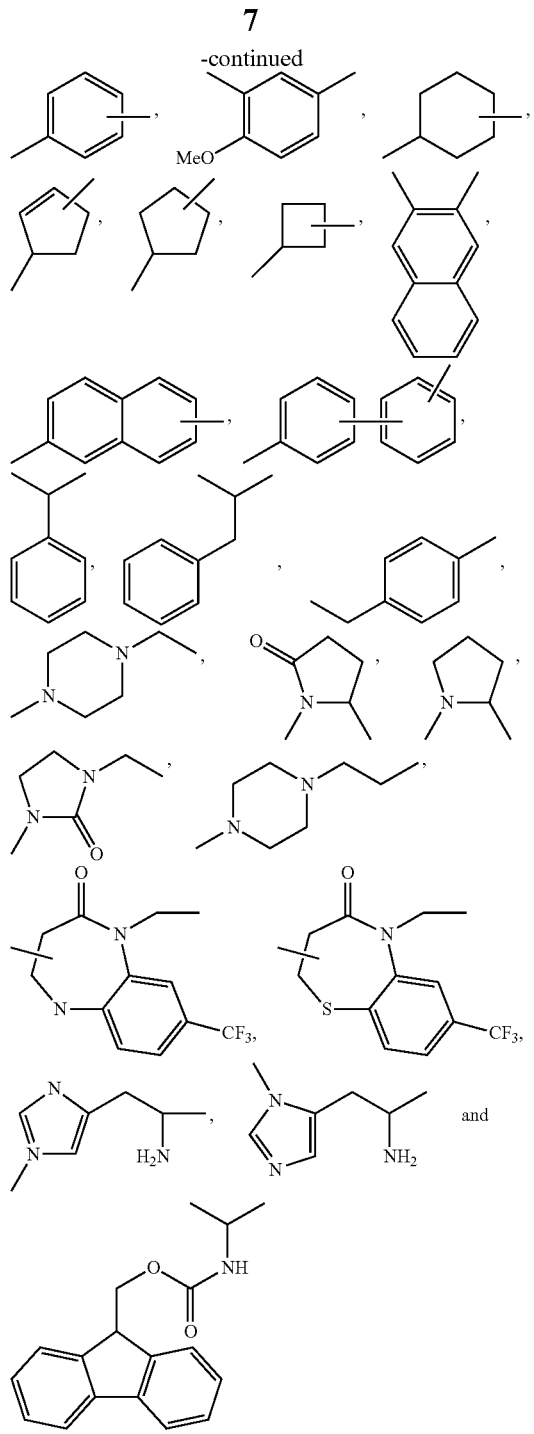

(wherein u is an integer of 1 to 10,
v is an integer of 1 to 10,
$R^{zc1}$ represents an amino-straight chain $C_{1-5}$ alkyl-carbonyl group, or an X-straight chain $C_{1-5}$ alkyl group (wherein X is as defined above),
$R^{zc2}$ represents an amino-straight chain $C_{1-5}$ alkyl-carbonylamino-straight chain $C_{1-5}$ alkyl group), and
m2 is an integer of 0 to 5), and
$C^b$ represents a bond, —CO—, or —SO$_2$—].

[9] The compound of item [1] or a salt thereof, wherein Lc is a divalent group represented by formula (ii):

-$Q^{c'}$-$C^{b'}$—

[wherein $Q^{c'}$ is a divalent group represented by formula:

—(CH$_2$)$_{m1'}$—$Z^{c'}$—(CH$_2$)$_{m2'}$—

(wherein m1' is an integer of 0 to 15,
$Z^{c'}$ represents

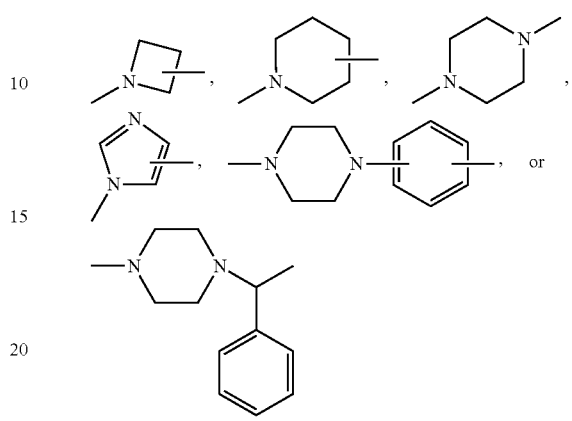

and m2' is an integer of 0 to 15), and
$C^{b'}$ represents a bond, —CO— or —SO$_2$—].

[10] An anorectic agent comprising the compound of item [1] or a salt thereof.

[11] An agent for preventing or treating obesity comprising the compound of item [1] or a salt thereof.

[12] A method for preventing or treating obesity in a mammal, comprising administering the compound of item [1] or a salt thereof to the mammal.

[13] Use of the compound of item [1] or a salt thereof for producing an agent for preventing or treating obesity.

The present invention further provides the following compounds of items [14] and [15].

[14] A compound represented by formula

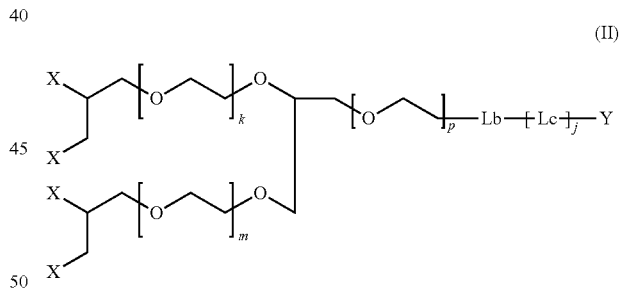

(II)

[wherein Y represents a polypeptide consisting of an amino acid sequence set forth in SEQ ID NO.: 1 wherein 1 to 4 amino acids are substituted, and
the amino acid substitution in the amino acid sequence set forth in SEQ ID NO.: 1 is selected from:
(1) substitution of Tyr at position 1 with Ala, Arg, Glu, Ser; Gln, NMeArg, or Pro;
(2) substitution of Phe at position 2 with Val, Gln, Arg, Glu, Ser, Tyr, Pro, Cha, or Aib;
(3) substitution of Leu at position 3 with Gln, Arg, Glu, Ser, Val, Phe, Pro, Thr, Cha, Nle, NMeArg, or Aib;
(4) substitution of Phe at position 4 with Gln, Leu, Pro, Cha, NMePhe, or Aib;
(5) substitution of Arg at position 5 with Nle, Gln, NMeArg, or Aib;
(6) substitution of Pro at position 6 with Ala or Aib;

(7) substitution of Arg at position 7 with Arg(Me); and (8) substitution of Asn at position 8 with Nle, Gln, Arg, Asp, Pro, or Aib;

X represents a methoxypolyethylene glycol (provided that a plurality of Xs, each representing a methoxypolyethylene glycol, may be the same or different);

Lb represents —$(CH_2)_i$— (wherein i is an integer of 1 to 5);

Lc represents a divalent group represented by formula (i):

—NH-$Q^c$-$C^b$—

(wherein $Q^c$ represents formula:

—$(CH_2)_{m1}$—$Z^c$—$(CH_2)_{m2}$—

(wherein $m^1$ is an integer of 0 to 15, $Z^c$ represents (a) a bond, or (b) a divalent group selected from —CO—, —O—CO—, —CO—O—, —CO—NH—, —NH—CO—, —CO—NH—CO—, —NH—CO—NH—, —CH($NH_2$)—, —CH(—$NHR^{zc1}$)—, —CH($R^{zc2}$)—, —CH(OH)—, —CH(COOH)—, —C(=NH)—, —S—, —S—S—, —SO—, —$SO_2$—, —NH—$SO_2$—, —$SO_2$—NH—,

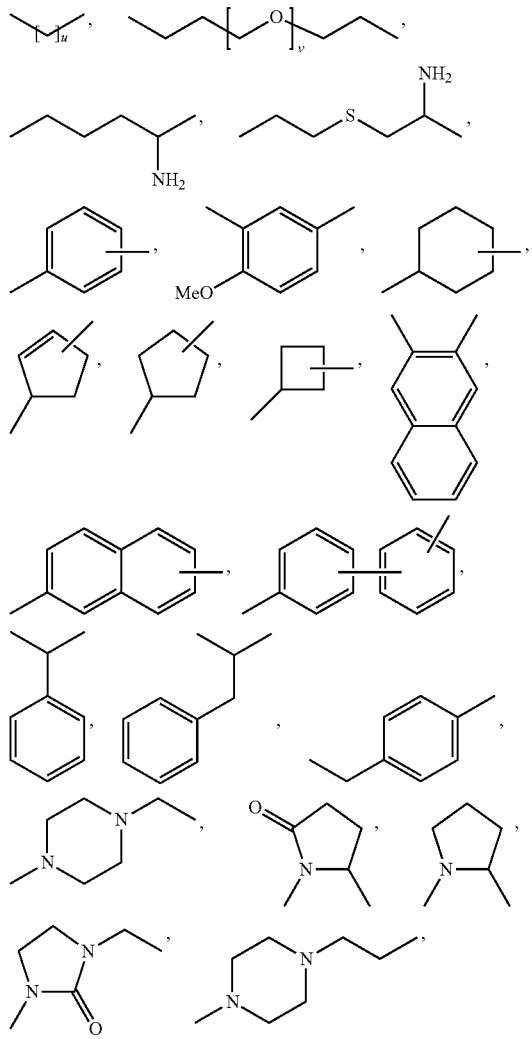

(wherein u is an integer of 1 to 18, v represents an integer of 1 to 12, $R^{zc1}$ represents an amino-straight chain $C_{1-5}$ alkyl-carbonyl group or an X-straight chain $C_{1-5}$ alkyl group (wherein X is as defined above), $R^{zc2}$ represents an amino-straight chain $C_{1-5}$ alkyl-carbonylamino-straight chain $C_{1-5}$ alkyl group), and m2 represents an integer of 0 to 15), $C^b$ represents a bond, —CO—, or —$SO_2$—), or a divalent group represented by formula (ii):

-$Q^{c'}$-$C^{b'}$—

(wherein $Q^{c'}$ represents formula:

—$(CH_2)_{m1'}$—$Z^{c'}$—$(CH_2)_{m2'}$—

(wherein m1' is an integer of 0 to 15, and $Z^{c'}$ represents a divalent group selected from

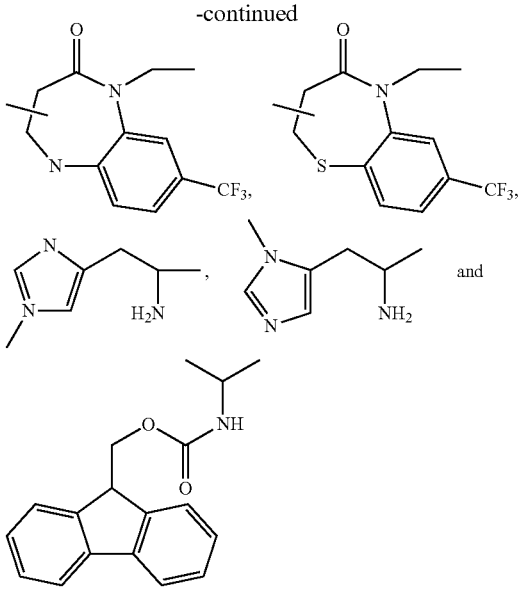

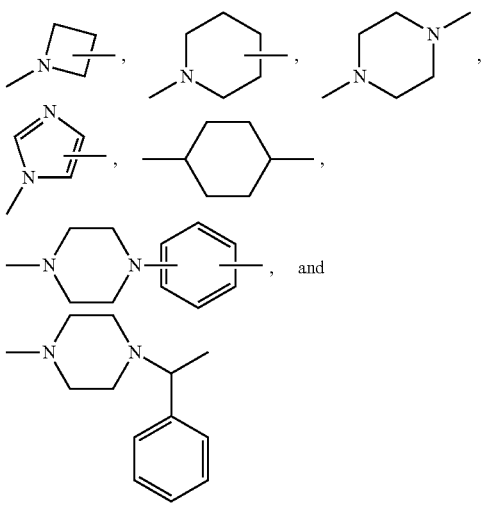

and m2' is an integer of 0 to 15), and $C^{b'}$ is —CO— or —$SO_2$—);

k is an integer of 1 to 100;

m is an integer of 1 to 100;

p is an integer of 1 to 100; and
j is an integer of 0 to 3] or a salt thereof.

[15] A compound represented by formula

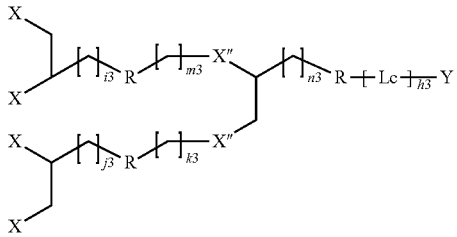
(III)

[wherein Y represents a polypeptide comprising an amino acid sequence set forth in SEQ ID NO.: 1 wherein 1 to 4 amino acids are substituted,
the amino acid substitution in the amino acid sequence set forth in SEQ ID NO.: 1 is selected from:
(1) substitution of Tyr at position 1 with Ala, Arg, Glu, Ser, Gln, NMeArg, or Pro;
(2) substitution of Phe at position 2 with Val, Gln, Arg, Glu, Ser, Tyr, Pro, Cha, or Aib;
(3) substitution of Leu at position 3 with Gln, Arg, Glu, Ser, Val, Phe, Pro, Thr, Cha, Nle, NMeArg, or Aib;
(4) substitution of Phe at position 4 with Gln, Leu, Pro, Cha, NMePhe, or Aib;
(5) substitution of Arg at position 5 with Nle, Gln, NMeArg, or Aib;
(6) substitution of Pro at position 6 with Ala or Aib;
(7) substitution of Arg at position 7 with Arg(Me); and
(8) substitution of Asn at position 8 with Nle, Gln, Arg, Asp, Pro, or Aib;
X represents a methoxypolyethylene glycol (provided that a plurality of Xs, each representing a methoxypolyethylene glycol, may be the same or different), and
X" represents a polyethylene glycol (provided that a plurality of X"s, each representing a polyethylene glycol, may be the same or different);
Lc represents a divalent group represented by formula (i):

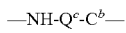

(wherein $Q^c$ is a divalent group represented by formula:

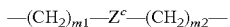

(wherein $m^1$ is an integer of 0 to 15),
$Z^c$ represents (a) a bond, or (b) a divalent group selected from —CO—, —O—CO—, —CO—O—, —CO—NH—, —NH—CO—, —CO—NH—CO—, —NH—CO—NH—, —CH(NH$_2$)—, —CH(—NHR$^{zc1}$)—, —CH(R$^{zc2}$)—, —CH(OH)—, —CH(COOH)— —C(=NH)—, —S—, —S—S—, —SO—, —SO$_2$—, —NH—SO$_2$—, —SO$_2$—NH—,

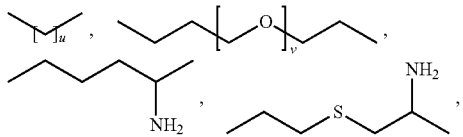

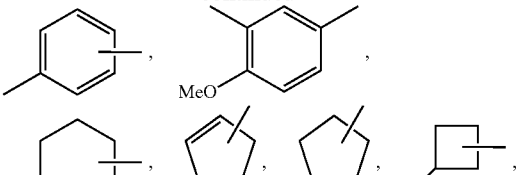

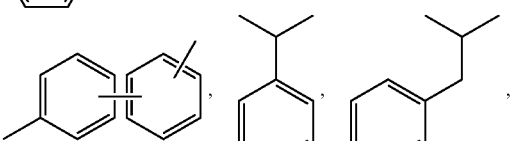

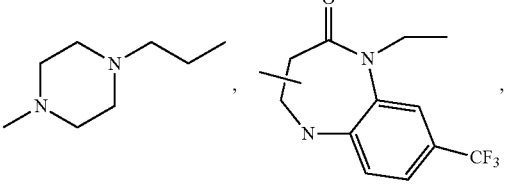

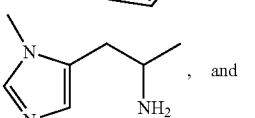, and

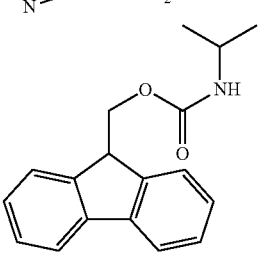

(wherein u is an integer of 1 to 18,
v is an integer of 1 to 12,
$R^{zc1}$ represents an amino-straight chain $C_{1-5}$ alkyl-carbonyl group, or an X-straight chain $C_{1-5}$ alkyl group (wherein X is as defined above), and
$R^{zc2}$ represents an amino-straight chain $C_{1-5}$ alkyl-carbonylamino-straight chain $C_{1-5}$ alkyl group), and m2 is an integer of 0 to 15), and
$C^b$ represents a bond, —CO—, or —SO$_2$—), or
a divalent group represented by formula (ii):

(wherein $Q^{c'}$ is a divalent group represented by formula:

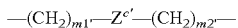

(wherein m1' is an integer of 0 to 15,
$Z^{c'}$ represents a divalent group selected from

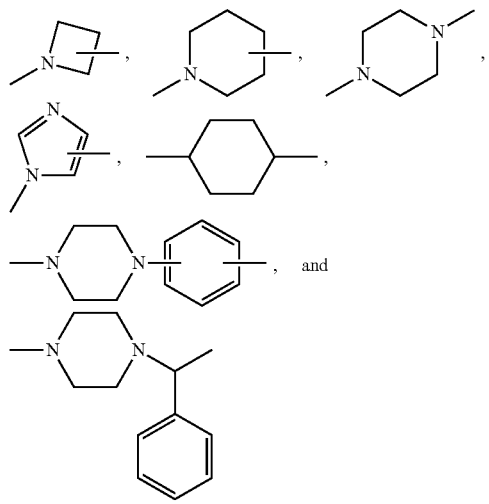

and m2' represents an integer of 0 to 15), and
$C^{b'}$ represents —CO— or —SO$_2$—); and
R is, at each occurrence, the same or different, and represents a divalent group selected from a bond, —O—, —CO—O—, —O—CO—, —NH—, —CO—, —S—, —S—S—, —SO—, —SO$_2$—, —NH—SO$_2$—, —SO$_2$—NH—, —C(=O)—NH—N=CH—, —C(=NH)—NH—, —CO—CH$_2$—S—, or

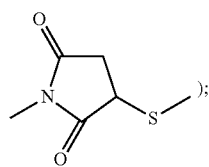

h3 is an integer of 0 to 3; and
i3, j3, k3, m3, and n3 may be the same or different, and each represents an integer of 0 to 5]; or a salt thereof.

The compounds (I), (II) and (III) may be collectively referred to as the compound of the invention (or the neuromedin U derivative of the present invention).

Advantageous Effects of Invention

The neuromedin U derivative of the present invention is highly stable and can exhibit a high anorectic effect, even when administered in a usual manner, for example, peripherally. Thus, the neuromedin U derivative of the invention is useful as an anorectic agent.

Further, the neuromedin U derivative of the invention is useful as an agent for preventing or treating obesity, since the neuromedin U derivative of the present invention is highly stable and can exhibit a high antiobesity effect, even when administered in a usual manner, for example, peripherally.

MODE FOR CARRYING OUT THE INVENTION

In the present specification, examples of the "straight chain $C_{1-5}$ alkyl" include methyl, ethyl, n-propyl, n-butyl, and n-pentyl. Methyl(CH$_3$) may be hereinafter indicated as "Me" according to convention.

The abbreviations used herein to indicate amino acids, etc. are according to abbreviations defined in the IUPAC-IUB Commission on Biochemical Nomenclature or common abbreviations used in this field, examples of which are shown below.

For amino acids that may exist as optical isomers, their L-forms are denoted unless otherwise specified.
Gly: glycine
Ala: alanine
Val: valine
Leu: leucine
Ile: isoleucine
Ser: serine
Thr: threonine
Cys: cysteine
Met: methionine
Glu: glutamic acid
Asp: aspartic acid
Lys: lysine
Arg: arginine
His: histidine
Phe: phenylalanine
Tyr: tyrosine
Trp: tryptophan
Pro: proline
Asn: asparagine
Gln: glutamine
Aib: 2-aminoisobutyric acid
Arg(Me): N$^\omega$-methylarginine
Cha: β-cyclohexylalanine
Nle: norleucine
NMeArg: N$^\alpha$-methylarginine
NMePhe: N-methylphenylalanine
Arg: arginine
Phe: phenylalanine
NMeTyr: N$^\alpha$-methyltyrosine
D-Tyr: D-tyrosine
Tyr(PO$_3$H$_2$): O-phosphotyrosine
Hse: homoserine
Nal(1): 1-naphthylalanine
Nal(2): 2-naphthylalanine
Leu(Me): γ-methylleucine
NMeLeu: N$^\alpha$-methylleucine
D-Leu: D-leucine
D-Ala: D-alanine
Abu: 2-aminobutanoic acid
Phe(4F): 4-fluorophenylalanine
Pya(4): 4-pyridylalanine
αMePhe: C$^\alpha$-methylphenylalanine
Orn: ornithine
Dbu: 2,4-diaminobutanoic acid
Hyp: trans-4-hydroxyproline
NMeAla: N$^\alpha$-methylalanine
MeGly: N-methylglycine
NMeAsn: N$^\alpha$-methylasparagine In the specification, the peptides are shown in accordance with the conventional way of describing peptides; that is, the N-terminus (amino terminus) is shown on the left-hand side, and the C-terminus (carboxyl terminus) on the right-hand side.

In brief, the compound of the present invention is a polypeptide that consisting of an amino acid sequence of 8 residues at the C-terminus of NMU whose 1 to 4 amino acids are substituted, and that is linked to a methoxypolyethylene glycol via a linker. More specifically, such a compound is a neuromedin U derivative and conjugate.

The amino acid sequence of 8 residues at the C-terminus of NMU is represented by SEQ ID NO.: 1 (Tyr-Phe-Leu-Phe-Arg-Pro-Arg-Asn-NH$_2$). In the present specification, the phrase "polypeptide consisting of an amino acid sequence set forth in SEQ ID: 1 whose 1 to 4 amino acids are substituted" may be simply referred to as "peptide to be used in the present invention". The first amino acid residue at the N-terminus is designated as position 1 in accordance with the conventional way of describing peptides.

The peptide used in the present invention is bound to a linker preferably at the α-amino group of the N-terminus.

The terms used in formula (i) alone or commonly used in formulas (I), (II), and (III) will be explained below. Y represents a polypeptide consisting of an amino acid sequence set forth in SEQ ID NO.: 1 whose 1 to 4 amino acids are substituted, i.e., a peptide to be used in the present invention.

When 3 or 4 amino acids are substituted, the amino acid substitution preferably includes at least one of the following substitutions: substitution of Tyr at position 1; substitution of Phe at position 2; substitution of Leu at position 3; substitution of Arg at position 5; and substitution of Pro at position 6.

Embodiment 1

The amino acid substitution in the amino acid sequence set forth in SEQ ID NO.: 1 is selected from the following:
(1) substitution of Tyr at position 1 with Ala, Arg, Glu, Ser, Gln, NMeArg, Phe, NMeTyr, D-Tyr, Trp, or Pro;
(2) substitution of Phe at position 2 with Val, Gln, Arg, Glu, Ser, Tyr, Pro, Cha, Trp, NMePhe, Nle, Tyr(PO$_3$H$_2$), Hse, Nal (1), Nal (2), Phe (4F), or Aib;
(3) substitution of Leu at position 3 with Gln, Arg, Glu, Ser, Val, Phe, Pro, Thr, Cha, Nle, NMeArg, Ile, Leu(Me), Lys, NMeLeu, D-Leu, Ala, D-Ala, Gly, Abu, or Aib;
(4) substitution of Phe at position 4 with Gln, Leu, Pro, Cha, NMePhe, Trp, Phe(4F), Pya(4), aMePhe, Nle, Ala, or Aib;
(5) substitution of Arg at position 5 with Nle, Gln, NMeArg, Orn, Dbu, Pya(4), Hse, or Aib;
(6) substitution of Pro at position 6 with Ala, Hyp, NMeAla, MeGly, NMeSer, D-NMeAla, or Aib;
(7) substitution of Arg at position 7 with Arg(Me) or NMe-Arg; and
(8) substitution of Asn at position 8 with Nle, Gln, Arg, Asp, Pro, Abu, NMeAsn, or Aib.

More preferably, the amino acid substitution is selected from the following:
(1) substitution of Tyr at position 1 with Arg, Phe, NMeTyr, or Pro;
(2) substitution of Phe at position 2 with Glu, Tyr, Trp, or Nal(2);
(3) substitution of Leu at position 3 with Gln, Arg, Val, Cha, or NMeLeu;
(4) substitution of Phe at position 4 with Trp;
(5) substitution of Arg at position 5 with Gln or NMeArg;
(6) substitution of Pro at position 6 with Ala or NMeAla; and
(7) substitution of Arg at position 7 with Arg(Me) or NMe-Arg.

Embodiment 2

In another embodiment of the present invention, the amino acid substitution in the amino acid sequence set forth in SEQ ID NO.: 1 is selected from the following:
(1) substitution of Tyr at position 1 with Ala, Arg, Glu, Ser, Gln, NMeArg, or Pro;
(2) substitution of Phe at position 2 with Val, Gln, Arg, Glu, Ser, Tyr, Pro, Cha, or Aib;
(3) substitution of Leu at position 3 with Gln, Arg, Glu, Ser, Val, Phe, Pro, Thr, Cha, Nle, NMeArg, or Aib;
(4) substitution of Phe at position 4 with Gln, Leu, Pro, Cha, NMePhe, or Aib;
(5) substitution of Arg at position 5 with Nle, Gln, NMeArg, or Aib;
(6) substitution of Pro at position 6 with Ala or Aib;
(7) substitution of Arg at position 7 with Arg(Me); and
(8) substitution of Asn at position 8 with Nle, Gln, Arg, Asp, Pro, or Aib.

More preferably, the amino acid substitution in the amino acid sequence set forth in SEQ ID NO.: 1 is selected from the following:
(1) substitution of Tyr at position 1 with Ala, Arg, Ser, Gln, NMeArg, or Pro;
(2) substitution of Phe at position 2 with Val, Gln, Arg, Glu, Ser, Tyr, Pro, or Cha;
(3) substitution of Leu at position 3 with Gln, Arg, Glu, Ser, Val, Phe, Pro, Thr, Cha, Nle, NMeArg, or Aib;
(4) substitution of Phe at position 4 with Leu, Pro, Cha, or NMePhe;
(5) substitution of Arg at position 5 with Nle, Gln, or NMe-Arg;
(6) substitution of Pro at position 6 with Ala or Aib;
(7) substitution of Arg at position 7 with Arg(Me); and
(8) substitution of Asn at position 8 with Nle, Gln, or Asp.

More preferably, the amino acid substitution is selected from the following:
(1) substitution of Tyr at position 1 with Arg, NMeArg, or Pro;
(2) substitution of Phe at position 2 with Gln or Tyr;
(3) substitution of Leu at position 3 with Gln, Arg, Cha, Val, or NMeArg;
(4) substitution of Arg at position 5 with Gln or NMeArg; and
(5) substitution of Arg at position 7 with Arg(Me).

In view of metabolism stability, the amino acid substitution includes preferably (1) substitution of Arg at position 5 with NMeArg; (2) substitution of Arg at position 7 with Arg(Me); or both.

More preferably, the amino acid substitution includes (1) substitution of Phe at position 2 with Nal(2); (2) substitution of Pro at position 6 with NMeAla; or both.

The number of amino acids substituted is preferably 1 or 2, and more preferably 1.

The peptide to be used in the present invention has substantially the same activity as that of neuromedin U.

"Examples of activities which are substantially the same as those of neuromedin U" include an FM3 binding activity, TGR1 binding activity, and anorectic activity. "Substantially the same" means that the properties are characteristically (e.g., physiologically or pharmacologically) similar. Although it is desirable that these activities are similar (e.g., about 0.01 to 100 times, preferably about 0.1 to 10 times, and more preferably 0.5 to 2 times), the potency of these activities may be different. These activities can be measured according to the methods described in the Examples of this specification.

The peptide to be used in the present invention is particularly preferably a polypeptide consisting of an amino acid sequence selected from SEQ ID NOs.: 2 to 20:

```
                                         (SEQ ID NO: 2)
Tyr-Phe-Leu-Phe-Gln-Pro-Arg-Asn-NH2;

(SEQ ID NO: 3)
Tyr-Phe-Gln-Phe-Arg-Pro-Arg-Asn-NH2;

(SEQ ID NO: 4)
Tyr-Phe-Arg-Phe-Arg-Pro-Arg-Asn-NH2;

(SEQ ID NO: 5)
Tyr-Phe-Val-Phe-Arg-Pro-Arg-Asn-NH2;

(SEQ ID NO: 6)
Tyr-Tyr-Leu-Phe-Arg-Pro-Arg-Asn-NH2;

(SEQ ID NO: 7)
Tyr-Phe-Cha-Phe-Arg-Pro-Arg-Asn-NH2;

(SEQ ID NO: 8)
Arg-Phe-Leu-Phe-Arg-Pro-Arg-Asn-NH2;

(SEQ ID NO: 9)
Pro-Phe-Leu-Phe-Arg-Pro-Arg-Asn-NH2;

(SEQ ID NO: 10)
Phe-Trp-Leu-Phe-Arg-Ala-Arg-Asn-NH2;

(SEQ ID NO: 11)
Tyr-Phe-Leu-Phe-Arg-Pro-Arg-Asp-NH2;

(SEQ ID NO: 12)
Tyr-Phe-Leu-Phe-NMeArg-Pro-Arg-Asn-NH2;

(SEQ ID NO: 13)
Tyr-Phe-Leu-Phe-Arg-Pro-Arg(Me)-Asn-NH2;

(SEQ ID NO: 14)
Tyr-Phe-NMeLeu-Phe-Arg-Pro-NMeArg-Asn-NH2;

(SEQ ID NO: 15)
NMeTyr-Phe-NMeLeu-Phe-NMeArg-Pro-Arg-Asn-NH2;

(SEQ ID NO: 16)
Tyr-Trp-Leu-Phe-Arg-NMeAla-Arg-Asn-NH2;

(SEQ ID NO: 17)
Tyr-Glu-Leu-Phe-Arg-NMeAla-Arg-Asn-NH2;

(SEQ ID NO: 18)
Tyr-Glu-Leu-Phe-Arg-Ala-Arg-Asn-NH2;

(SEQ ID NO: 19)
Tyr-Trp-Leu-Phe-Arg-Ala-Arg-Asn-NH2;
and (SEQ ID NO: 20)
Tyr-Nal(2)-Leu-Phe-Arg-NMeAla-Arg-Asn-NH2.
```

In another embodiment (Embodiment 2) of the present invention, the peptide to be used in the present invention is a polypeptide consisting of an amino acid sequence set forth in one of SEQ ID NOs.: 2 to 9. As is clear from the above, the C-terminus in SEQ ID NOs.: 2 to 20 is amidated (that is, —OH in the carboxyl group (—COOH) is replaced by $NH_2$).

The peptide to be used in the present invention may be derived from the cells of warm-blooded animals (e.g., humans, mice, rats, guinea pigs, hamsters, rabbits, sheep, goats, swine, bovine, horses, birds, cats, dogs, monkeys, and chimpanzees) [e.g., splenocytes, nerve cells, glial cells, pancreatic β-cells, bone marrow cells, mesangial cells, Langerhans' cells, epidermal cells, epithelial cells, goblet cells, endothelial cells, smooth muscle cells, fibroblasts, fibrocytes, muscle cells, fat cells, immune cells (e.g., macrophages, T cells, B cells, natural killer cells, mast cells, neutrophils, basophils, eosinophils, monocytes, and dendritic cells), megakaryocytes, synovial cells, chondrocytes, osteocytes, osteoblasts, osteoclasts, mammary cells, hepatic cells or interstitial cells, and the corresponding precursor cells, stem cells, and cancer cells], or from any tissues where such cells are present [for example, brain or parts of the brain (e.g., olfactory bulb, amygdaloid nucleus, basal ganglia, hippocampus, thalamus, hypothalamus, cerebral cortex, medulla oblongata, and cerebellum), spinal cord, pituitary gland, stomach, pancreas, kidney, liver, gonads, thyroid gland, gall bladder, bone marrow, adrenal gland, skin, muscle, lung, gastrointestinal tract (e.g., large intestine and small intestine), blood vessel, heart, thymus, spleen, submandibular gland, peripheral blood, prostate, testis, ovary, placenta, uterus, bone, joint, adipose tissue, skeletal muscle, and peritoneum]. The peptide to be used in the present invention may be synthesized chemically or in a cell-free translation system. Alternatively, the peptide to be used in the present invention may be a genetically modified peptide produced from a transformant to which a nucleic acid containing a base sequence that encodes the amino acid sequence is induced.

X represents a methoxypolyethylene glycol.

X' is absent or represents a methoxypolyethylene glycol.

X' is preferably absent.

The "methoxypolyethylene glycol" represented by X and X' may be linear or branched. The molecular weight (or average molecular weight) of the "methoxypolyethylene glycol" and "polyethylene glycol" is not particularly limited, and is preferably about 10,000 to 40,000 daltons, preferably about 20,000 to 40,000 daltons, more preferably about 20,000 to 35,000 daltons, and even more preferably about 20,000 daltons.

The "methoxypolyethylene glycol" is represented by formula:

$$MeO—(CH_2—CH_2—O)_n—$$

wherein n represents the degree of polymerization (or average degree of polymerization), which is preferably about 350 to 1350, and more preferably about 450 to 1350.

The partial structure represented by:

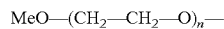

in formula (i) is a linker which connects a "methoxypolyethylene glycol" represented by X and X' to a polypeptide represented by Y. The linker is not particularly limited, and linkers that are commonly used for PEGylation of polypeptides can be used.

La is a divalent or trivalent group represented by formula

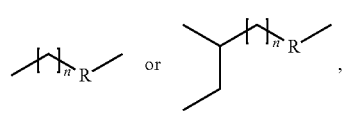

(wherein R represents a bond, —O—, —CO—O—, —O—CO—, —NH—, —CO—, —S—, —S—S—,

—SO—, —SO$_2$—, —NH—SO$_2$—, —SO$_2$—NH—, —C(=O)—NH—N=CH—, —C(=NH)—NH—, —CO—CH$_2$—S— or

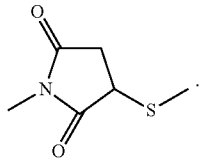

La is preferably a divalent or trivalent group represented by formula

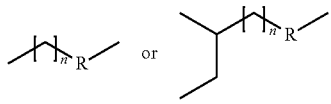

(wherein R represents a bond, and n is an integer of 0).

Specifically, La is preferably a bond or

Lb represents —(CH$_2$)$_i$— (wherein i is an integer of 1 to 5).
Lb is preferably —(CH$_2$)$_i$— (wherein i is an integer of 3).
Lc is a divalent group represented by formula (i):

—NH-Q$^c$-C$^b$—

(wherein Q$^c$ is a divalent group represented by formula:

—(CH$_2$)$_{m1}$—Z$^c$—(CH$_2$)$_{m2}$—

(wherein m1 is an integer of 0 to 15,
Z$^c$ is (a) a bond, or (b) —CO—, —O—CO—, —CO—O—, —CO—NH—, —NH—CO—, —CO—NH—CO—, —NH—CO—NH—, —CH(NH$_2$)—, —CH(—NHR$^{zc1}$)—, —CH(R$^{zc2}$)—, —CH(OH)—, —CH(COOH)—, —C(=NH)—, —S—, —S—S—, —SO—, —SO$_2$-, —NH—SO$_2$—, —SO$_2$—NH—,

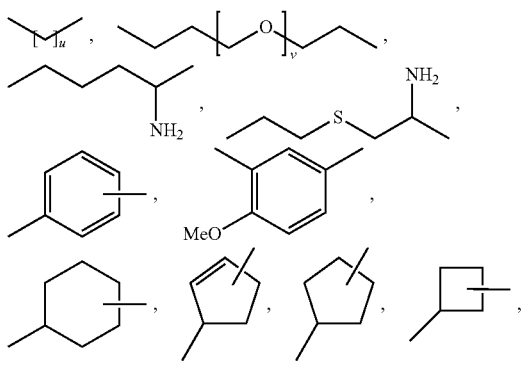

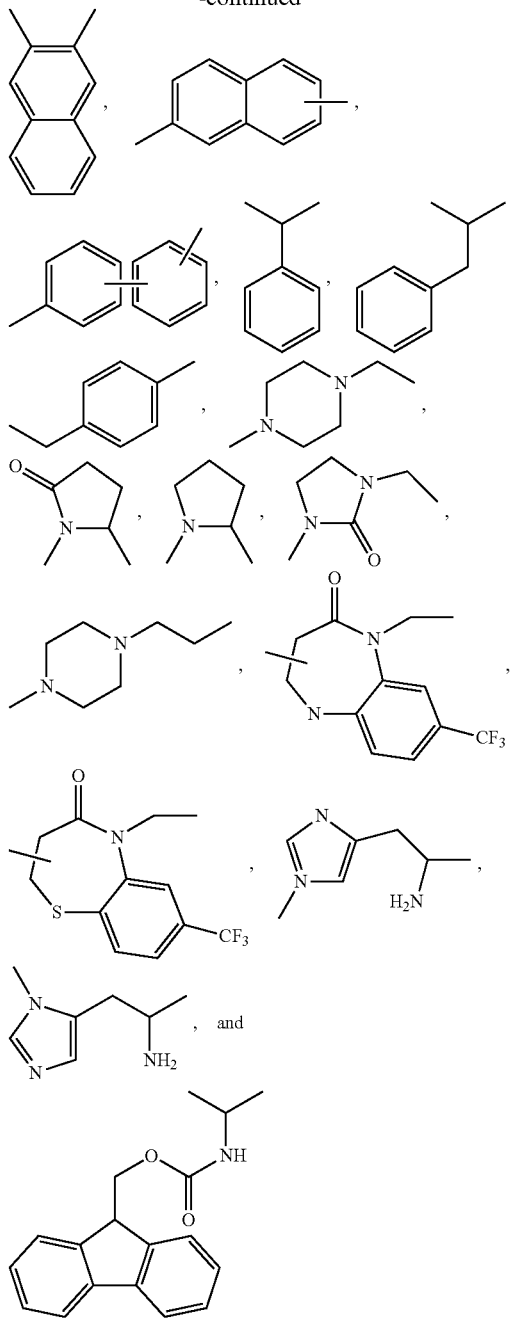

(wherein u is an integer of 1 to 18,
v is an integer of 1 to 12,
R$^{zc1}$ represents an amino-straight chain C$_{1-5}$ alkyl-carbonyl group, or an X-linear C$_{1-5}$ alkyl group (X is as defined above), and
R$^{zc2}$ represents an amino-straight chain C$_{1-5}$ alkyl-carbonylamino-straight chain C$_{1-5}$ alkyl group, and
m2 is an integer of 0 to 15),
C$^b$ represents a bond, —CO—, or —SO$_2$—), or
a divalent group represented by formula (ii):

-Q$^{c'}$-C$^{b'}$—

(wherein Q$^{c'}$ represents formula:

—(CH$_2$)$_{m1'}$—Z$^{c'}$—(CH$_2$)$_{m2'}$—

(wherein m1' is an integer of 0 to 15,
Z$^{c'}$ represents a divalent group selected from

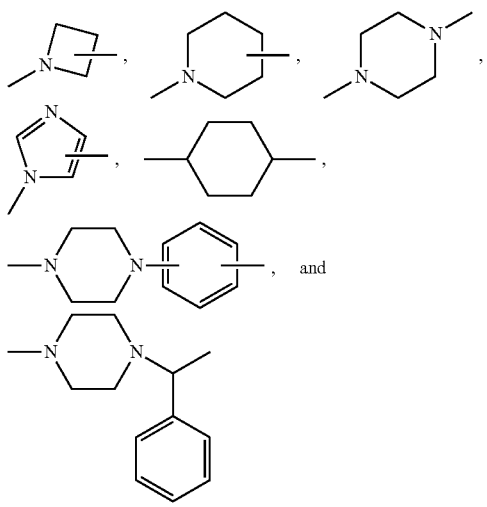

and
m2' is an integer of 0 to 15), and
C$^{b'}$ represents —CO— or —SO$_2$—).

Lc is preferably a divalent group represented by formula (i):

(wherein Q$^c$ is a divalent group represented by formula:

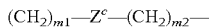

(wherein m1 is an integer of 0,
Z$^c$ represents (a) a bond, or (b) a divalent group selected from —CO—, —CH(—NHR$^{zc1}$)—, —CH(R$^{zc2}$)—,

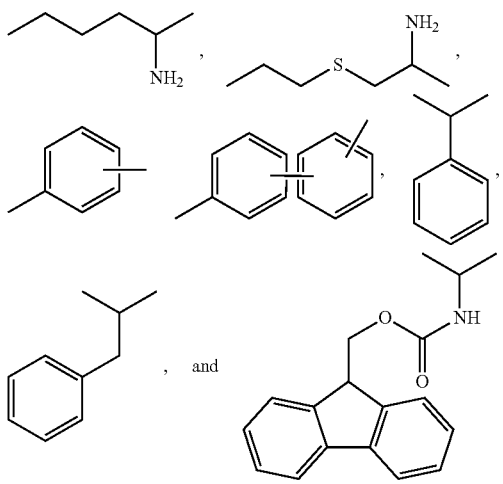

(wherein u is an integer of 1 to 18,
v is an integer of 1 to 12,
R$^{zc1}$ represents an amino-straight chain C$_{1-5}$ alkyl-carbonyl group, or an X-linear C$_{1-5}$ alkyl group (wherein X is as defined above),
R$^{zc2}$ represents an amino-straight chain C$_{1-5}$ alkyl-carbonylamino-straight chain C$_{1-5}$ alkyl group), and
m2 is an integer of 0 to 10),
C$^b$ represents a bond, —CO—, or —SO$_2$—), or a divalent group represented by formula (ii):

(wherein Q$^{c'}$ is a divalent group represented by formula:

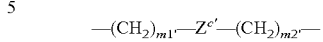

(wherein m1' is 0, and
Z$^{c'}$ is a divalent group selected from

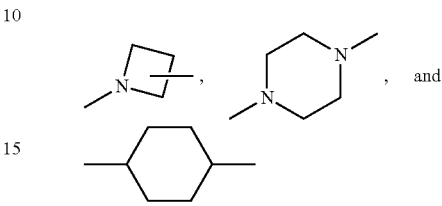

and m2' is an integer of 0 to 2), and
C$^{b'}$ represents —CO— or —SO$_2$—).
j is an integer of 1 to 3, and
j is preferably an integer of 1 or 2.

The distance from the nitrogen atom closest to the Lb in the Lc to the nitrogen atom at the N-terminus of the polypeptide represented by Y is preferably 3.5 to 30 Å, and more preferably 3.5 to 15 Å.

Lc is preferably a divalent group represented by formula (i):

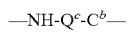

[wherein Q$^c$ is a divalent group represented by formula:

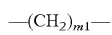

(wherein m1 is an integer of 0 to 15), and C$^b$ represents a bond, —CO— or —SO$_2$—].

Preferably, the distance from the nitrogen atom of NH of formula:

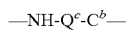

to the nitrogen atom of the N-terminus of the polypeptide represented by Y is 3.5 to 7.0 Å.

The nitrogen atom of NH of formula:

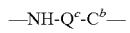

is marked with an asterisk (*) in the formula below.

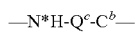

Preferably, Lc is a divalent atom represented by formula (i):

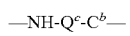

[wherein Q$^c$ is a divalent group represented by formula:

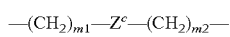

(wherein m1 is an integer of 0 to 10,
Z$^c$ is a divalent group selected from —CO—, —O—CO—, —CO—O—, —CO—NH—, —NH—CO—, —CO—NH—CO—, —NH—CO—NH—, —CH(NH$_2$)—, —CH(—NHR$^{zc1}$)—, —CH(R$^{zc2}$)—, —CH(OH)—, —CH(COOH)—, —C(=NH)—, —S—, —S—S—, —SO—, —SO$_2$—, —NH—SO$_2$—, —SO$_2$NH—,

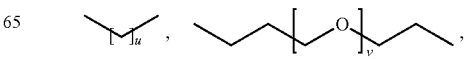

-continued

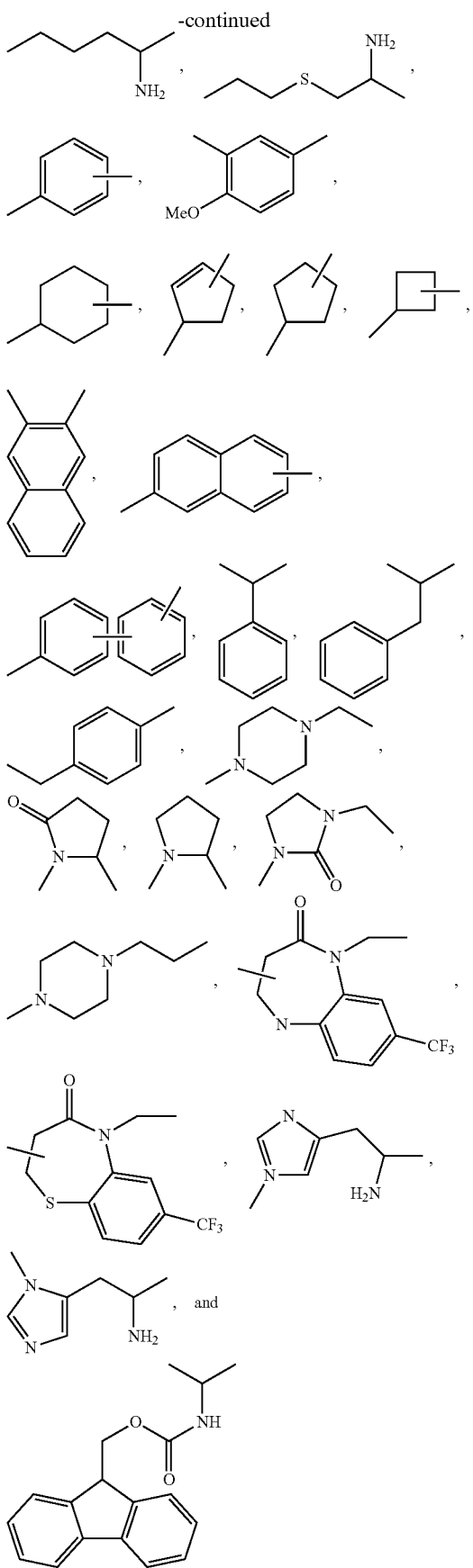

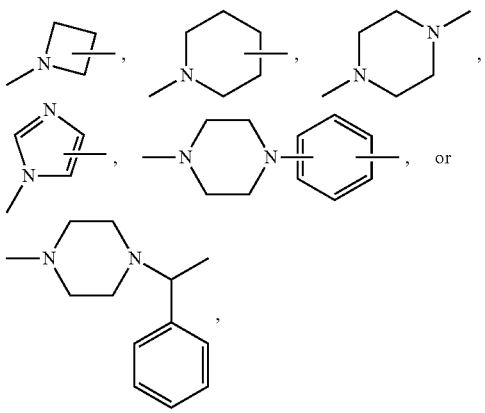

(wherein u is an integer of 1 to 10,
v is an integer of 1 to 10,
$R^{zc1}$ represents an amino-straight chain $C_{1-5}$ alkyl-carbonyl group, or an X-linear $C_{1-5}$ alkyl group (wherein X is as defined above),
$R^{zc2}$ represents an amino-straight chain $C_{1-5}$ alkyl-carbonylamino-straight chain $C_{1-5}$ alkyl group),
m2 is an integer of 0 to 5), and
$C^b$ represents a bond, —CO—, or —SO$_2$—].

Preferably, the distance from the nitrogen atom of NH in formula:

—NH-Q$^c$-C$^b$— to the atom closest to —(CH$_2$)$_{m1}$— in $Z^c$ is 3.5 to 10 Å, and the distance from the atom closest to —(CH$_2$)$_{m1}$— to the nitrogen atom of the N-terminus of the polypeptide represented by Y is 3.5 to 7.0 Å.

Preferably, Lc is a divalent group represented by formula (ii):

-Q$^{c'}$-C$^{b'}$—

[wherein Q$^{c'}$ is a divalent group represented by formula:

—(CH$_2$)$_{m1'}$—Z$^{c'}$—(CH$_2$)$_{m2'}$—

(wherein m1' is an integer of 0 to 15, $Z^{c'}$ represents and m2' is an integer of 0 to 15), and
$C^{b'}$ represents a bond, —CO—, or —SO$_2$—].

Preferably, the distance from the nitrogen atom closest to Lb in $Z^{c'}$ to the nitrogen atom at the N-terminus of the polypeptide represented by Y is 5 to 10 Å.

Each of these distances is an interatomic distance in a three-dimensional stable structure that is output by subjecting a three-dimensional molecular model of a compound or a partial structure thereof to commercial molecular modeling and calculation software (e.g., Gaussian, MOPAC, AMBER, CHARMM, MOE, Insight, etc., sold by Ryoka Systems Inc.) to make energy stabilization calculations as an extended structure. In each software, parameters are pre-set in such a manner that the interatomic distance corresponds to the interatomic distance estimated from X-ray crystal structural analysis (for example, Cambridge Structural Database, etc.). For example, the error of molecules consisting of approximately 20 common heavy atoms is less than 0.2 Å (regarding AMBER, see J. Am. Chem. Soc, 106, 765-784).

(Lc)$_j$ is preferably (a) a bond, or (b) a divalent group selected from —NH—(CH$_2$)$_{mc1}$—CO—, —NH—(CH$_2$)$_{mc2}$—CO—NH—(CH$_2$)$_{mc3}$—CO—,

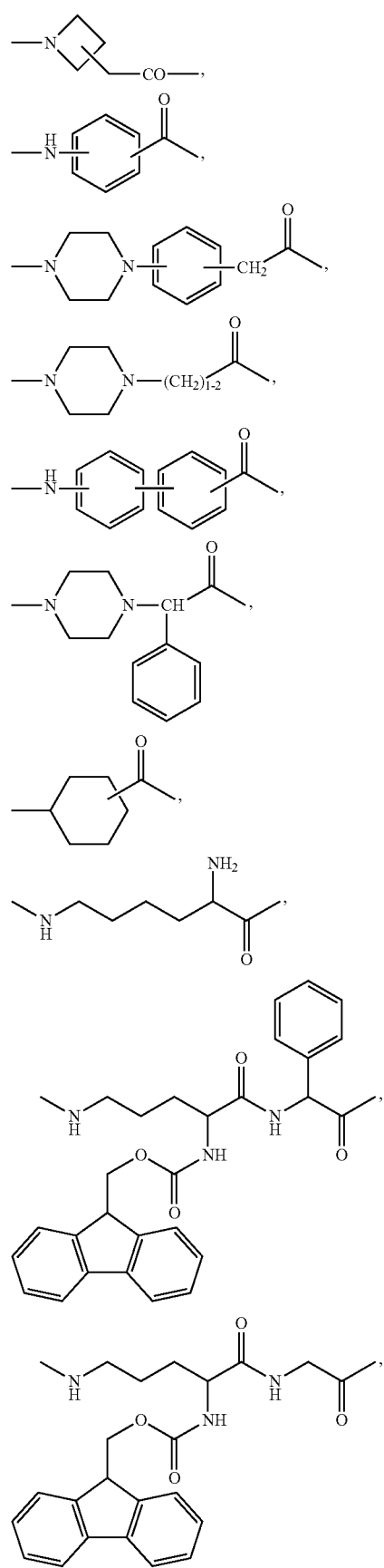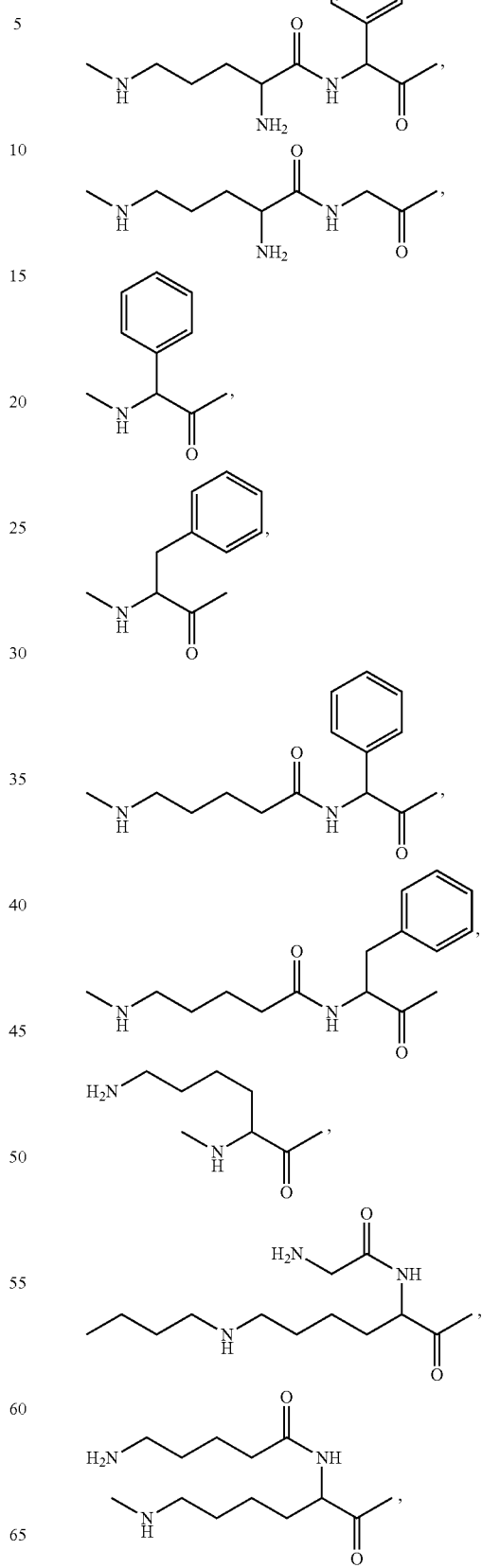

-continued
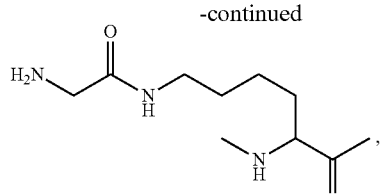
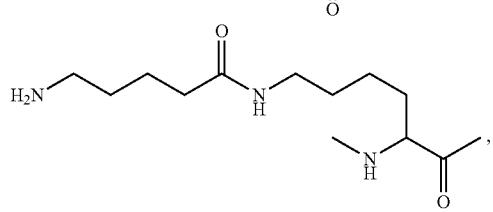
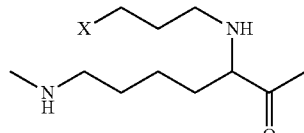
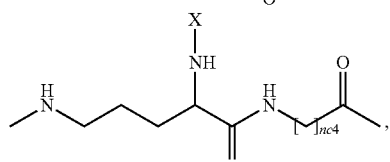
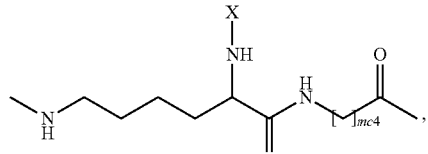
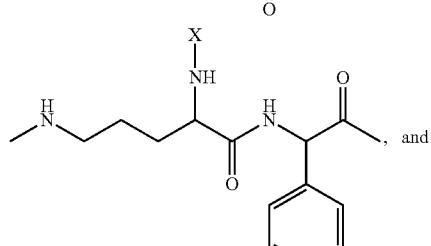, and
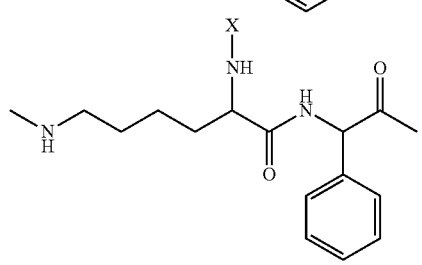
(wherein mc1 is an integer of 1 to 11, mc2 and mc3 independently represent an integer of 1 to 5 (preferably provided that the sum of mc2 and mc3 is 4 to 7), mc4 is an integer of 1 to 5, and X is as defined above).
Preferably, Lb is a bond, and (Lc)$_j$ is
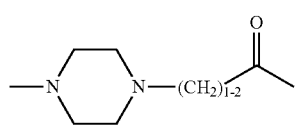
The partial structure represented by:
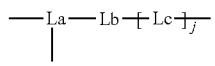
is preferably
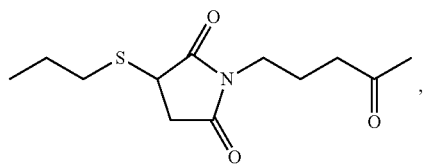,
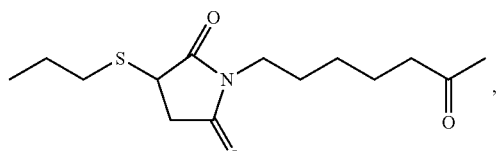,
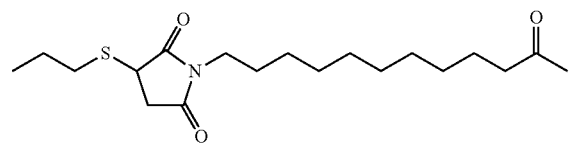,
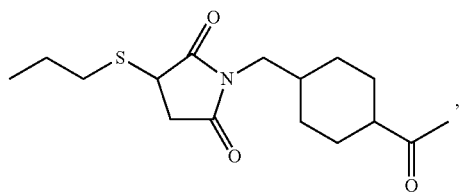,
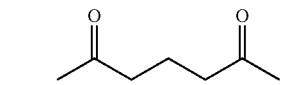,
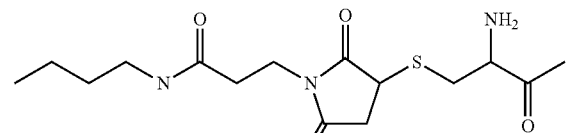,
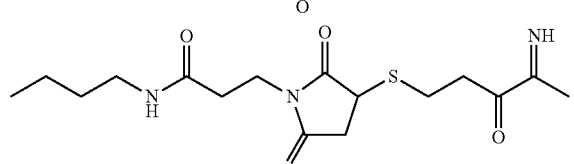,
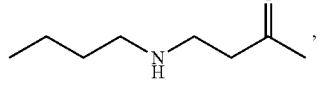,
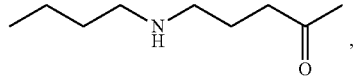,
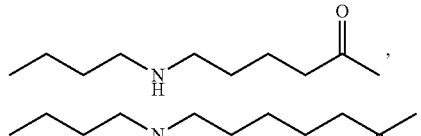, or

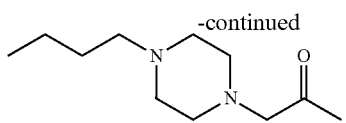

The partial structure represented by:

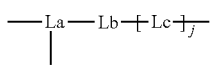

is particularly preferably

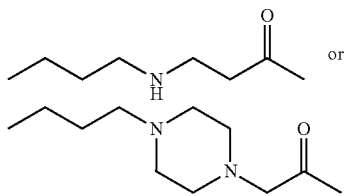

Preferable examples of the compound represented by formula (i) include compounds represented by formula:

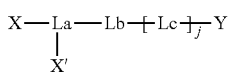  (I)

[wherein Y represents a polypeptide consisting of an amino acid sequence selected from SEQ ID NOs.: 2 to 20,
X represents a methoxypolyethylene glycol;
X' is absent;
La is a divalent or trivalent group represented by formula

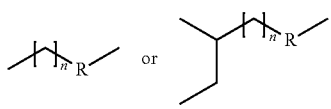

(wherein R is a bond, —O—, —CO—, —O—CO—, —NH—, —CO—, —S—, —S—S—, —SO—, —SO$_2$—, —NH—SO$_2$—, —SO$_2$—NH—, —C(=O)—NH—N=CH—, —C(=NH)—NH—, —CO—CH$_2$—S—, or

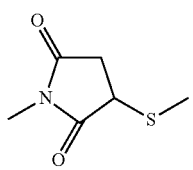

and n is an integer of 0 to 5);
Lb represents —(CH$_2$)$_i$— (wherein i is an integer of 1 to 5);
Lc is a divalent group represented by formula (i):

—NH-Q$^c$-C$^b$—

(wherein Q$^c$ is a divalent group represented by formula:

—(CH$_2$)$_{m1}$—Z$^c$—(CH$_2$)$_{m2}$—

(wherein m1 is an integer of 0 to 10, Z$^c$ is a divalent group selected from —CO—, —O—CO—, —CO—O—, —CO—NH—, —NH—CO—, —CO—NH—CO—, —NH—CO—NH—, —CH(NH$_2$)—, —CH(—NHR$^{zc1}$)—, —CH(R$^{zc2}$)—, —CH(OH)—, —CH(COOH)—C(=NH)—, —S—, —S—S—, —SO—, —SO$_2$—, —SO$_2$—NH—,

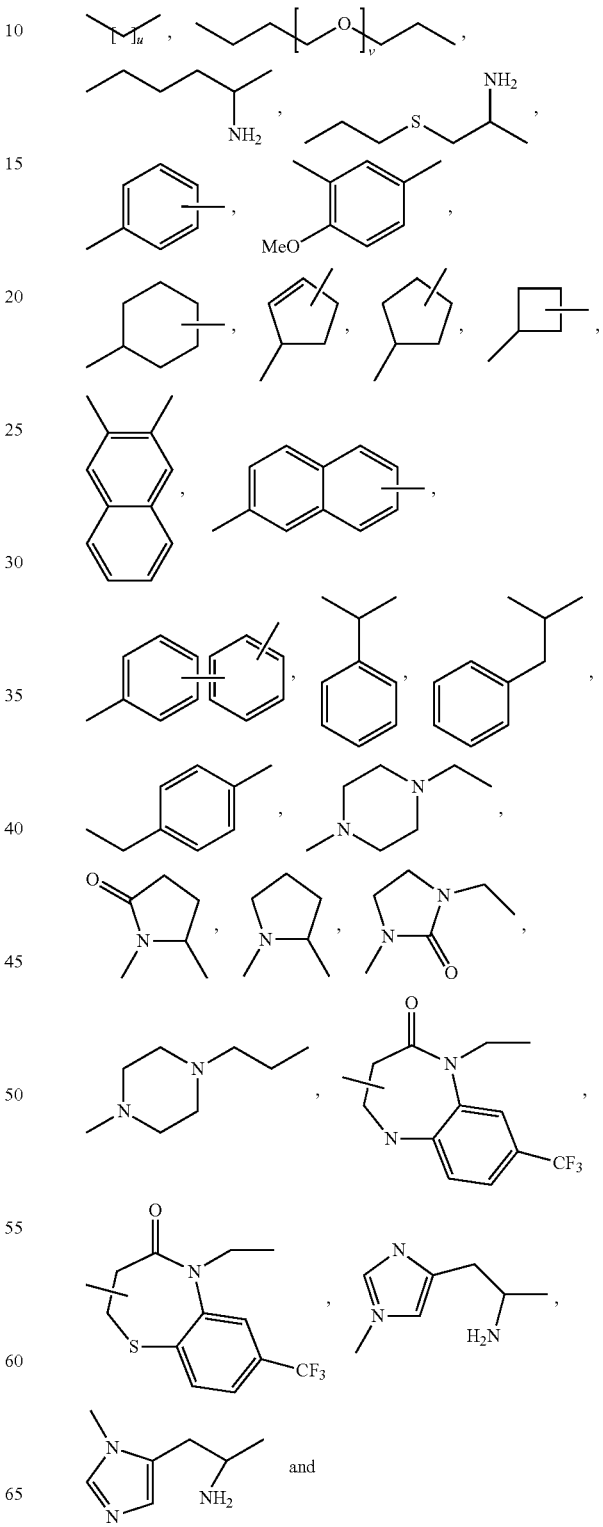

-continued

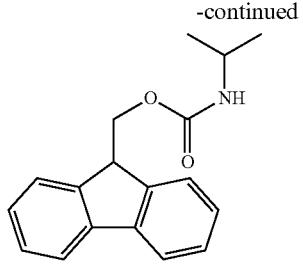

(wherein u is an integer of 1 to 10, v is an integer of 1 to 10, $R^{zc1}$ represents an amino straight chain $C_{1-5}$ alkyl-carbonyl group, or an X-linear $C_{1-5}$ alkyl group (wherein X is as defined above), $R^{zc2}$ represents an amino-straight chain $C_{1-5}$ alkyl-carbonylamino-straight chain $C_{1-5}$ alkyl group), and m2 is an integer of 0 to 5), and $C^b$ represents a bond, —CO—, or —$SO_2$—); and j is an integer of 1 to 3]; and salts thereof.

Preferably, the partial structure represented by:

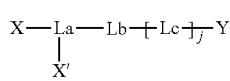

is

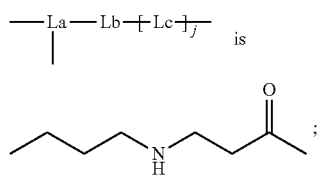

;

Other preferable examples of the compound represented by formula (i) include compounds represented by formula $$X—La—Lb—(Lc)_j—Y \quad (I)$$
$$\quad | \quad$$
$$\quad X'$$

(wherein Y represents an amino acid sequence selected from SEQ ID NOs.: 2 to 20, X represents a methoxypolyethylene glycol;

X' is absent;

La is a divalent or trivalent group represented by formula

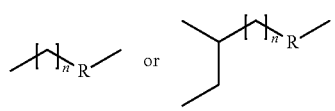

(wherein R represents a bond, —O—, —CO—O—, —O—CO—, —NH—, —CO—, —S—, —S—S—, —SO—, —$SO_2$—, —NH—$SO_2$—, —$SO_2$—NH—, —C(=O)—NH—N=CH—, —C(=NH)—NH—, —CO—$CH_2$—S— or

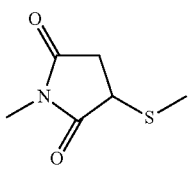

and n is an integer of 0 to 5);

Lb is a divalent group represented by —$(CH_2)_i$— (wherein i is an integer of 1 to 5);

Lc is a divalent group represented by formula:

$$-Q^{c'}-C^{b'}-$$

(wherein $Q^{c'}$ is a divalent group represented by formula:

$$—(CH_2)_{m1'}—Z^{c'}—(CH_2)_{m2'}—$$

(wherein m1' is an integer of 0 to 15, $Z^{c'}$ represents

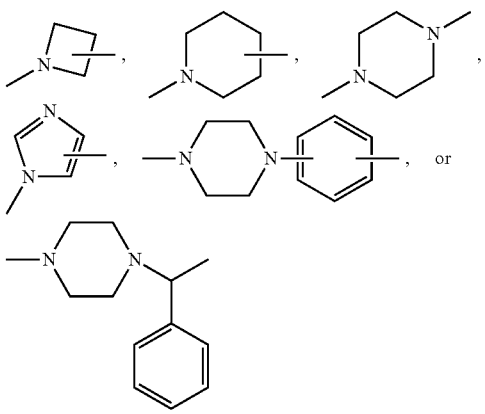

m2' is an integer of 0 to 15), $C^{b'}$ represents a bond, —CO— or —$SO_2$—; and j is an integer of 1 to 3); and salts thereof.

Preferably, the moiety represented by the partial structure:

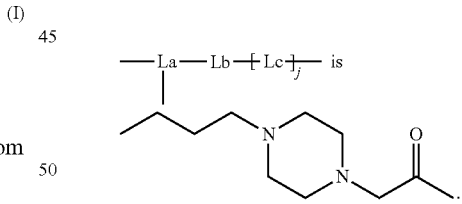

Further, other preferable examples of the compound represented by formula (i) include compounds represented by formula

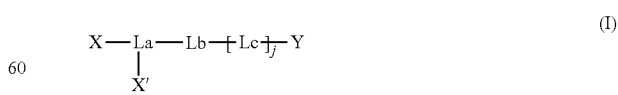

[wherein Y represents a polypeptide consisting of an amino acid sequence set forth in SEQ ID NO.: 1 whose 1 to 4 amino acids are substituted;

the amino acid substitution in the amino acid sequence set forth in SEQ ID NO.: 1 is selected from:

(1) substitution of Tyr at position 1 with Arg, NMeArg, or Pro;
(2) substitution of Phe at position 2 with Gln;
(3) substitution of Leu at position 3 with Gln, Arg, Cha, Val, or NMeArg;
(4) substitution of Arg at position 5 with Gln or NMeArg; and
(5) substitution of Arg at position 7 with Arg(Me);
X represents a methoxypolyethylene glycol;
X' is absent or represents a methoxypolyethylene glycol;
La is a divalent or trivalent group represented by formula

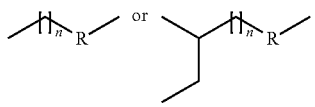

(wherein
R represents a bond, and
n is an integer of 0);
Lb is —$(CH_2)_i$— (wherein i is an integer of 3); and
Lc is a divalent group represented by formula (i):

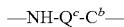

(wherein $Q^c$ is a divalent group represented by formula:

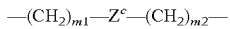

(wherein m1 is an integer of 0,
$Z^c$ represents (a) a bond or (b) a divalent group selected from —CO—, —CH(—$NHR^{zc1}$)—, —CH($R^{zc2}$)—,

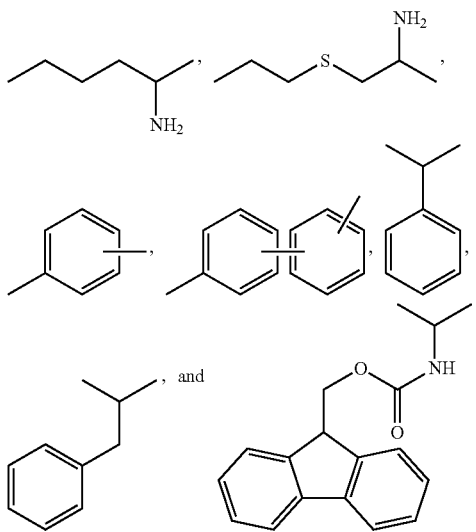

(wherein u represents an integer of 1 to 18,
v is an integer of 1 to 12,
$R^{zc1}$ represents an amino-straight chain $C_{1-5}$ alkyl-carbonyl group, or an X-linear $C_{1-5}$ alkyl group (wherein X is as defined above),
$R^{zc2}$ represents an amino-straight chain $C_{1-5}$ alkyl-carbonylamino-straight chain $C_{1-5}$ alkyl group),
m2 is an integer of 0 to 10, and
$C^b$ represents a bond, —CO—, or —$SO_2$—), or
a divalent group represented by formula (ii):

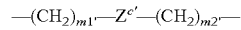

(wherein $Q^{c'}$ is a divalent group represented by formula:

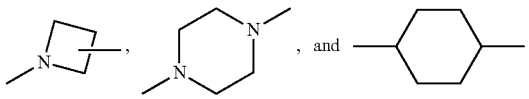

(wherein m1' is 0,
$Z^{c'}$ represents a divalent group selected from

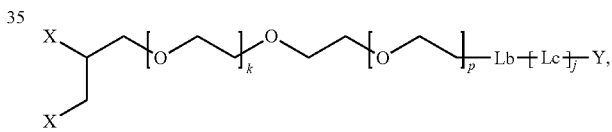

wherein m2' is an integer of 0 to 2), and
$C^{b'}$ represents CO— or —$SO_2$—); and
j is an integer of 1 to 2]; and
salts thereof.

In the above embodiments, straight chain linkers and 2-branched linkers that can connect two methoxypolyethylene glycol molecules were explained. In other embodiments of the present invention, a linker that is branched into many branches and can thereby connect numerous methoxypolyethylene glycols may be used.

For example, a 4-branched linker structure can be easily designed by branching a 2-branched linker alkylene portion.

For example, when the neuromedin U derivative of the present invention having a 2-branched linker has the following structure:

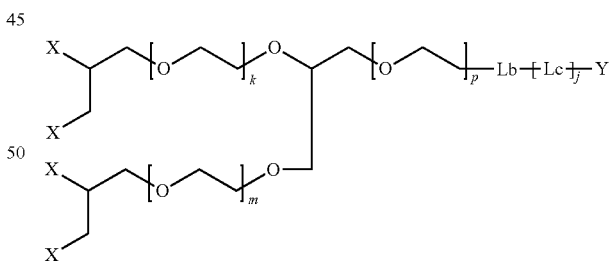

a 4-branched linker structure can be designed as follows.

Further, when the neuromedin U derivative of the present invention having a 2-branched linker has the following structure:

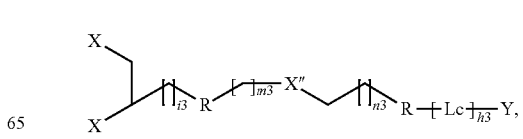

a 4-branched linker structure can be designed as follows.

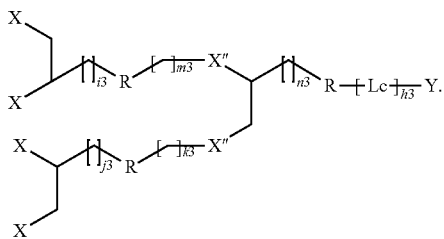

Similarly, 6-branched, 8-branched, and 10-branched to 32-branched linkers can be designed. These linkers can also be used in the neuromedin U derivatives of the present invention.

The neuromedin U derivative having a 4-branched linker will be explained below.

One embodiment of such a neuromedin U derivative is compound (II) as defined above.

In formula (II), k is an integer of 1 to 100, m is an integer of 1 to 100, and p is an integer of 1 to 100.

Other symbols are as explained above.

Another embodiment of the neuromedin U derivative of the present invention having a four-branched linker is compound (III) as defined above.

In formula (III), h3 is an integer of 0 to 3; and i3, j3, k3, m3, and n3 are the same or different, and each represents an integer of 0 to 5.

Other symbols are as explained above.

[Production Method]

The method for producing the neuromedin derivative of the present invention will be explained below.

The neuromedin derivatives of the present invention can be produced by binding a methoxypolyethylene glycol via a linker to a peptide to be used in the present invention.

The peptide used in the neuromedin derivative of the present invention can be prepared from the aforementioned warm-blooded animal cells or tissues by a known peptide purification method. Specifically, the tissues or cells of warm-blooded animals are homogenized, and the soluble fractions are isolated and purified by chromatography, such as reversed phase chromatography, ion exchange chromatography, and affinity chromatography, to prepare a neuromedin derivative of the present invention.

Further, the peptide used in the neuromedin derivative of the present invention can be purchased as a commercial product.

The peptide used in the neuromedin derivative of the present invention can be produced according to a peptide synthesis method known per se.

The peptide synthesis method may be, for example, a solid phase synthesis method or a liquid phase synthesis method. A desired protein can be produced by condensing a partial peptide or amino acids that can form the neuromedin derivative of the present invention, and the remaining portion, and eliminating any protecting group the resultant product may have.

The condensation and elimination of the protecting group can be performed according to methods known per se, such as those described in (1) to (5) below:

(1) M. Bodanszky and M. A. Ondetti, Peptide Synthesis, Interscience Publishers, New York (1966);
(2) Schroeder and Luebke, The Peptide, Academic Press, New York (1965);
(3) Nobuo Izumiya, et al.: Peptide Gosei-no-Kiso to Jikken (Peptide Synthesis Fundamentals and Experiments), published by Maruzen Co. (1975);
(4) Haruaki Yajima and Shunpei Sakakibara: Seikagaku Jikken Koza (Biochemistry Experiment Lecture Series) 1, Tanpakushitsu no Kagaku (Protein Chemistry) IV, 205 (1977); and
(5) Haruaki Yajima, ed.: Zoku Iyakuhin no Kaihatsu (Second Series Drug Development), Vol. 14, Peptide Synthesis, published by Hirokawa Shoten.

The neuromedin derivative of the present invention thus obtained can be isolated and purified by known purification methods.

Further, the peptide to be used in the present invention can also be produced by culturing a transformant containing a nucleic acid that encodes the peptide, and isolating and purifying the peptide to be used in the present invention from the obtained culture.

The nucleic acid that encodes the peptide used in the present invention may be DNA or RNA, or a DNA/RNA chimera, and is preferably DNA. The nucleic acid may be double-stranded or single-stranded. The double-stranded nucleic acid may be double-stranded DNA, double-stranded RNA, or a DNA-RNA hybrid. The single-stranded nucleic acid may be a sense strand (i.e., coding strand) or an antisense strand (i.e., non-coding strand).

Examples of DNA that encodes the peptide to be used in the present invention include genomic DNA; cDNA derived from any cells of warm-blooded animals (e.g., humans, mice, rats, guinea pigs, hamsters, rabbits, sheep, goats, swine, bovine, horses, birds, cats, dogs, monkeys, and chimpanzees) [e.g., splenocytes, nerve cells, glial cells, pancreatic β-cells, bone marrow cells, mesangial cells, Langerhans' cells, epidermal cells, epithelial cells, endothelial cells, fibroblasts, fibrocytes, muscle cells, fat cells, immune cells (e.g., macrophages, T cells, B cells, natural killer cells, mast cells, neutrophils, basophils, eosinophils, monocytes, and dendritic cells), megakaryocytes, synovial cells, chondrocytes, osteocytes, osteoblasts, osteoclasts, mammary cells, hepatic cells or interstitial cells, and the corresponding precursor cells, stem cells, or cancer cells, and blood cells] or from any tissues where such cells are present [for example, brain or parts of the brain (e.g., olfactory bulb, amygdaloid nucleus, basal ganglia, hippocampus, thalamus, hypothalamus, subthalamic nucleus, cerebral cortex, medulla oblongata, cerebellum, occipital lobe, frontal lobe, temporal lobe, putamen, caudate nucleus, corpus callosum, nigra), spinal cord, pituitary gland, stomach, pancreas, kidney, liver, gonad, thyroid gland, gall bladder, bone marrow, adrenal gland, skin, muscle, lung, gastrointestinal tract (e.g., large intestine and small intestine), blood vessel, heart, thymus, spleen, submandibular gland, peripheral blood, peripheral hemocyte, prostate, testis, ovary, placenta, uterus, bone, joint, skeletal muscle, and peritoneum]; and synthetic DNA.

The genomic DNA and cDNA that encode the peptide to be used in the present invention can be directly amplified according to a method known per se, for example, the Polymerase Chain Reaction (hereinafter referred to as the "PCR method") and the Reserve Transcriptase-PCR (hereinafter abbreviated as the "RT-PCR method") using a genomic DNA fraction and total RNA or a mRNA fraction prepared from the aforementioned cells or tissues as templates. Alternatively, the genomic DNA and cDNA that encode the peptide to be used in the present invention can be respectively cloned from a genomic DNA library and a cDNA library that are prepared by inserting genomic DNA and total RNA or a mRNA fragment prepared from the aforementioned cells and tissues into an appropriate vector, by a method known per se, such as colony or plaque hybridization or PCR. The vector to be used in the libraries may be, for example, any of bacteriophages, plasmids, cosmids, and phagemids.

The neuromedin derivative of the present invention can be synthesized, for example, by any of the following methods.

(1) A PEGylation reagent containing an active ester (e.g., SUNBRIGHT MEGC-30-TS (trade name), NOF Corporation) is bound to the amino group of the peptide to be used in the present invention.

(2) A PEGylation reagent containing an aldehyde (e.g., SUNBRIGHT ME-300-AL (trade name), NOF Corporation) is bound to the amino group of the peptide to be used in the present invention.

(3) A divalent crosslinking reagent (e.g., GMBS (Dojindo Laboratories), EMCS (Dojindo Laboratories), KMUS (Dojindo Laboratories), SMCC (Pierce)) is bound to the peptide to be used in the present invention, and subsequently a PEGylation reagent containing a thiol group (e.g., SUNBRIGHT ME-300-SH (trade name), NOF Corporation) is bound. In this case, the linker in the neuromedin derivative of the present invention is derived from the PEGylation reagent and the divalent crosslinking reagent.

(4) An SH introduction agent (e.g., D-cysteine residue, L-cysteine residue, Traut's reagent) is introduced into the peptide to be used in the present invention, and a PEGylation reagent containing a maleimide group (e.g., SUNBRIGHT ME-300-MA (trade name), NOF Corporation) is reacted with this thiol group. In this case, the linker in the neuromedin derivative of the present invention is derived from the PEGylation reagent and the SH introduction agent.

(5) An SH introduction agent (e.g., D-cysteine residue, L-cysteine residue, Traut's reagent) is introduced into the peptide to be used in the present invention, and a PEGylation reagent containing an iodo-acetamide group (e.g., SUNBRIGHT ME-300-IA (trade name), NOF Corporation) is reacted with this thiol group. In this case, the linker in the neuromedin derivative of the present invention is derived from the PEGylation reagent and the SH introduction agent.

(6) ω-aminocarboxylic acid or α-amino acid is introduced as a linker to the N-terminal amino group of the peptide to be used in the present invention, and a PEGylation reagent containing an active ester (e.g., SUNBRIGHT MEGC-30-TS (trade name), NOF Corporation) is reacted with the amino group derived from this linker. In this case, the linker in the neuromedin derivative of the present invention is derived from the PEGylation reagent and ω-aminocarboxylic acid, or the PEGylation reagent and α-amino acid.

(7) ω-aminocarboxylic acid or α-amino acid is introduced as a linker to the N-terminal amino group of the peptide to be used in the present invention, and a PEGylation reagent containing an aldehyde group (e.g., SUNBRIGHT MEGC-30-AL (trade name), NOF Corporation) is reacted with the amino group derived from this linker. In this case, the linker in the neuromedin derivative of the present invention is derived from the PEGylation reagent and ω-aminocarboxylic acid, or the PEGylation reagent and α-amino acid.

The aforementioned reagents can be obtained, for example, as commercial products. Each reaction can be carried out by a method known to those in the art.

The neuromedin U derivative of the present invention may be a salt. Examples of such salts include salts with inorganic bases, salts with organic bases, salts with inorganic acids, salts with organic acids, and salts with basic or acidic amino acids.

Preferable examples of salts with inorganic bases include alkali metal salts such as sodium salts and potassium salts; alkali earth metal salts such as calcium salts and magnesium salts; and aluminum salts and ammonium salts.

Preferable examples of salts with organic bases include salts with trimethylamine, triethylamine, pyridine, picoline, ethanolamine, diethanolamine, triethanolamine, dicyclohexylamine, N,N-dibenzylethylenediamine, or the like.

Preferable examples of salts with inorganic bases include salts with hydrochloric acid, hydrobromic acid, nitric acid, sulfuric acid, phosphoric acid, or the like.

Preferable examples of salts with organic acids include salts with formic acid, acetic acid, trifluoroacetic acid, fumaric acid, oxalic acid, tartaric acid, maleic acid, succinic acid, malic acid, methanesulfonic acid, benzenesulfonic acid, p-toluenesulfonic acid, or the like.

Preferable examples of salts with basic amino acids include salts with arginine, lysine, ornithine, or the like.

Preferable examples of salts with acidic amino acids include salts with aspartic acid, glutamic acid, or the like.

When the neuromedin U derivative of the present invention is obtained in a free state by the aforementioned synthetic method, it may be converted to a salt according to a usual method. When the neuromedin U derivative of the present invention is obtained as a salt, it can be converted to a free form or other salts according to a usual method. The neuromedin U derivative of the present invention thus obtained can be isolated and purified from the reaction solution by a known means, such as phase transfer, concentration, solvent extraction, fractional distillation, crystallization, recrystallization, and chromatography.

When the neuromedin U derivative of the present invention is present in the form of a configurational isomer, diastereomer, conformer, etc., each can be isolated by the above-mentioned separation and purification means, if desired. When the neuromedin U derivative is racemic, it can be separated into an S-form and an R-form by usual optical resolution means.

When the neuromedin U derivative of the present invention is present in the form of a stereoisomer, those in the form of individual isomers and a mixture thereof are included within the scope of the present invention.

The neuromedin U derivative of the present invention may be a hydrate or non-hydrate. Further, the neuromedin U derivative of the present invention may be a solvate or a non-solvate.

The neuromedin U derivative of the present invention may be labeled with an isomer (e.g., $^3H$, $^{14}C$, or $^{35}S$), etc. Further, the neuromedin U derivative of the present invention may be substituted with deuterium.

The neuromedin U derivative of the present invention is useful as an anorectic agent, or as an agent for preventing or treating obesity.

The neuromedin U derivative of the present invention, which has high safety and low toxicity, can be administered as an anorectic agent or an agent for preventing or treating obesity to mammals (e.g., humans, mice, rats, rabbits, sheep, swine, bovine, horses, birds, cats, dogs, monkeys, and chimpanzees) in a usual manner, for example, peripherally.

The neuromedin U derivative of the present invention is typically used as a pharmaceutical composition obtained by formulating the derivative with a pharmacologically acceptable carrier according to a known method (e.g., a method described in the Japanese Pharmacopoeia).

As pharmacologically acceptable carriers, various organic or inorganic carrier substances usually used as materials for pharmaceutical preparations can be used. Examples of such carriers include excipients, lubricants, binders, and disintegrants for solid preparations; and solvents, solubilizers, suspending agents, isotonizing agents, buffers, and soothing agents for liquid preparations. If necessary, additives for pharmaceutical preparations, such as preservatives, antioxidants, colorants, and sweeteners, may be used to formulate such preparations.

Preferable examples of excipients include lactose, sucrose, D-mannitol, D-sorbitol, starch, gelatinized starch, dextrin, crystalline cellulose, low-substituted hydroxypropyl cellulose, sodium carboxymethylcellulose, gum arabic, pullulan, light anhydrous silicic acid, synthetic aluminum silicate, magnesium aluminometasilicate, xylitol, sorbitol, and erythritol.

Preferable examples of lubricants include magnesium stearate, calcium stearate, talc, colloidal silica, and polyethylene glycol 6000.

Preferable examples of binders include gelatinized starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropyl cellulose, hydroxypropyl methylcellulose, and polyvinylpyrrolidone.

Preferable examples of disintegrants include lactose, sucrose, starch, carboxymethylcellulose, calcium carboxymethylcellulose, croscarmellose sodium, sodium carboxymethyl starch, low-substituted hydroxypropylcellulose, light anhydrous silicic acid, and calcium carbonate.

Preferable examples of solvents include water for injection, saline, Ringer's solution, alcohol, propylene glycol, polyethylene glycol, sesame oil, corn oil, olive oil, and cottonseed oil.

Preferable examples of solubilizers include polyethylene glycol, propylene glycol, D-mannitol, trehalose, benzylbenzoate, ethanol, tris-aminomethane, cholesterol, triethanolamine, sodium carbonate, sodium citrate, sodium salicylate, and sodium acetate.

Preferable examples of suspending agents include surfactants such as stearyltriethanolamine, sodium lauryl sulfate, lauryl aminopropionic acid, lecithin, benzalkonium chloride, benzethonium chloride, and glycerol monostearate; hydrophilic polymers such as polyvinyl alcohol, polyvinylpyrrolidone, sodium carboxymethylcellulose, methylcellulose, hydroxymethylcellulose, hydroxyethylcellulose, and hydroxypropylcellulose; polysorbates and polyoxyethylene hydrogenated castor oil.

Preferable examples of isotonizing agents include sodium chloride, glycerin, D-mannitol, D-sorbitol, glucose, xylitol, and fructose.

Preferable examples of buffers include buffer solutions such as phosphates, acetates, carbonates, and citrates.

Preferable examples of soothing agents include propylene glycol, lidocaine hydrochloride, and benzyl alcohol.

Preferable examples of preservatives include p-oxybenzoic acid esters, chlorobutanol, benzyl alcohol, phenethyl alcohol, dehydroacetic acid, and sorbic acid.

Preferable examples of antioxidants include sulfites and ascorbates.

Preferable examples of colorants include water-soluble edible tar pigments (e.g., food colors such as Food Color Red Nos. 2 and 3, Food Color Yellow Nos. 4 and 5, and Food Color Blue Nos. 1 and 2), water-insoluble lake pigments (e.g., aluminum salts of the aforementioned water-soluble edible tar pigments), and natural pigments (e.g., β-carotene, chlorophyll, and red iron oxide).

Preferable examples of sweeteners include sodium saccharin, dipotassium glycyrrhizate, aspartame, and stevia.

Examples of the dosage form of the aforementioned pharmaceutical composition include oral preparations such as tablets (including sublingual tablets and orally disintegrable tablets), capsules (including soft capsules and micro capsules), granules, powders, troches, syrups, emulsions, and suspensions; and parenteral preparations such as injections (e.g., subcutaneous injections, intravenous injections, intramuscular injections, intraperitoneal injections, and intravenous drips), external preparations (e.g., transdermal preparations and ointments), suppositories (e.g., rectal suppositories and vaginal suppositories), pellets, transnasal preparations, pulmonary preparations (inhalants), and eye drops. These preparations may be controlled-release formulations, such as quick-release formulations and sustained-release formulations (e.g., sustained-release microcapsules).

The content of the neuromedin U derivative in the pharmaceutical compositions is, for example, 0.1 to 100 wt %.

Methods for producing such oral preparations and parenteral preparations are specifically explained below. Oral preparations can be produced by adding, for example, an excipient (e.g., lactose, sucrose, starch, D-mannitol, xylitol, sorbitol, erythritol, crystalline cellulose, and light anhydrous silicic acid), a disintegrant (e.g., calcium carbonate, starch, carboxymethylcellulose, calcium carboxymethylcellulose, low-substituted hydroxypropylcellulose, croscarmellose sodium, sodium carboxymethyl starch, and light anhydrous silicic acid), a binder (e.g., gelatinized starch, gum arabic, carboxymethylcellulose, hydroxypropylcellulose, hydroxypropylmethylcellulose, polyvinylpyrrolidone, crystalline cellulose, methylcellulose, sucrose, D-mannitol, trehalose, and dextrin), a lubricant (e.g., talc, magnesium stearate, calcium stearate, colloidal silica, and polyethylene glycol 6000), etc. to the active ingredient, and compression-molding the mixture.

Further, oral preparations may be coated by a method known per se for the purpose of masking of the taste, enteric coating, or sustained release. Examples of usable coating agents include enteric polymers (e.g., cellulose acetate phthalate, methacrylic acid copolymer L, methacrylic acid copolymer LD, methacrylic acid copolymer S, hydroxypropylmethylcellulose phthalate, hydroxypropylmethylcellulose acetate succinate, and carboxymethylethylcellulose), gastrosoluble polymers (e.g., polyvinylacetal diethylaminoacetate, and aminoalkyl methacrylate copolymer E), water-soluble polymers (e.g., hydroxypropylcellulose, and hydroxypropylmethylcellulose), water insoluble polymers (e.g., ethyl cellulose, aminoalkyl methacrylate copolymer RS, and ethyl acrylate-methyl methacrylate copolymer), and waxes. For coating, plasticizers such as polyethylene glycol, and light-shielding agents such as titanium oxide and iron sesquioxide may be used together with the above-mentioned coating agents.

Injections can be produced by dissolving, suspending, or emulsifying the active ingredient in an aqueous solvent (e.g., distilled water, saline, and Ringer's solution) or an oily solvent (e.g., a vegetable oil such as olive oil, sesame oil, cottonseed oil, and corn oil; propylene glycol, macrogol, and tricaprylin) together with a dispersing agent (e.g., Tween 80 (manufactured by Atlas Powder, USA), HCO 60 (manufactured by Nikko Chemicals Co., Ltd.), polyethyleneglycol, carboxymethylcellulose, and sodium alginate), a preservative (e.g., methylparaben, propylparaben, benzyl alcohol, chlorobutanol, and phenol), an isotonizing agent (e.g., sodium chloride, glycerine, D-sorbitol, D-mannitol, xylitol, glucose, and fructose). In this case, if desired, the following additives may be added: a solubilizer (e.g., sodium salicylate, sodium acetate, polyethylene glycol, propylene glycol, D-mannitol, trehalose, benzyl benzoate, ethanol, tris-aminomethane, cholesterol, triethanolamine, sodium carbonate, and sodium citrate), a suspending agent (e.g., surfactants such as stearyl triethanolamine, sodium laurylsulfate, lauryl aminopropionic acid, lecithin, benzalkonium chloride, benzethonium chloride, and glycerol monostearate; and hydrophilic polymers such as polyvinyl alcohol, polyvinyl pyrrolidone, sodium carboxymethylcellulose, methylcellulose, hydroxymethylcellulose, hydroxyethylcellulose and hydroxypropylcellulose), a buffer (e.g., buffer solutions such as phosphates, acetates, carboxylates, and citrates), a stabilizer (e.g., human serum albumin), a soothing agent (e.g., propylene glycol, lidocaine hydrochloride, and benzyl alcohol), and a preservative (e.g., p-oxybenzoic acid esters, chlorobutanol, benzalkonium chloride, benzyl alcohol, phenethyl alcohol, dehydroacetic acid, and sorbic acid).

External preparations can be produced by formulating the active ingredient into solid, semi-solid or liquid compositions.

For example, solid compositions as mentioned above can be produced by pulverizing the active ingredient as is, or by adding an excipient (e.g., lactose, D-mannitol, starch, crystalline cellulose, and sucrose), a thickener (e.g., natural gums, cellulose derivatives, and acrylic acid polymers) to the active ingredient, mixing them, and then pulverizing the mixture. Liquid compositions as mentioned above can be produced in almost the same manner as the injections. Semi-solid compositions are preferably in the form of an aqueous or oily gel, or an ointment. All of these compositions may also contain a pH modulating agent (e.g., phosphoric acid, citric acid, hydrochloric acid, and sodium hydroxide), or a preservative (e.g., p-oxybenzoic acid esters, chlorobutanol, benzalkonium chloride, benzylalcohol, phenethylalcohol, dehydroacetic acid, and sorbic acid). Suppositories can be produced by formulating the active ingredient into an oily or aqueous, solid, semi-solid, or liquid composition. Examples of oily bases usable in the production of the composition include higher fatty acid glycerides (e.g., cacao butter, and Witepsols), medium fatty acid triglycerides (e.g., Miglyols), and vegetable oils (e.g., sesame oil, soybean oil, and cottonseed oil). Examples of aqueous bases include polyethyleneglycols and propyleneglycol. Examples of aqueous gel bases include natural gums, cellulose derivatives, vinyl polymers, and acrylic acid polymers.

The dose of the neuromedin U derivative of the present invention can be appropriately selected according to the administration subject, administration route, target disease, clinical symptoms, etc. For example, when the pharmaceutical composition containing the neuromedin U derivative of the present invention as an active ingredient is subcutaneously administered to an adult, the neuromedin U derivative as an active ingredient is typically given in a single dose of about 5 to 5,000 µg, and preferably about 50 to 500 µg per human. This dose is preferably administered once to three times a day.

The neuromedin U derivative of the present invention may be used concomitantly with other drugs having no adverse effects on the neuromedin U derivative of the present invention for the purpose of enhancing the activity (e.g., an anorectic effect, and a preventive or therapeutic effect on obesity) of the derivative of the invention or reducing the amount thereof. Examples of such drugs include "agents for treating diabetes", "agents for treating diabetic complications", "agents for treating obesity", and "agents for treating hyperlipidemia"). Two or more such drugs (hereinafter sometimes simply referred to as "concomitant drugs") may be combined at an appropriate ratio for use.

Examples of the "agents for treating diabetes" include insulin preparations (e.g., animal insulin preparations extracted from pancreas of bovine and swine; human insulin preparations genetically synthesized using *Escherichia coli* and yeast; zinc insulin; protamine zinc insulin; fragments or derivatives of insulin (e.g., INS-1), and oral insulin preparations), insulin sensitizers (e.g., pioglitazone or a salt thereof (preferably hydrochloride), rosiglitazone or a salt thereof (preferably maleate), Tesaglitazar, Ragaglitazar, Muraglitazar, Edaglitazone, Metaglidasen, Naveglitazar, AMG-131, THR-0921, α-glucosidase inhibitors (e.g., voglibose, acarbose, miglitol, and emiglitate), biguanides (e.g., metformin, buformin, and their salts (e.g., hydrochloride, fumarate, and succinate)), insulin secretagogues [sulfonylureas (e.g., tolbutamide, glibenclamide, gliclazide, chlorpropamide, tolazamide, acetohexamide, glyclopyramide, glimepiride, glipizide, and glybuzole), repaglinide, nateglinide, and mitiglinide or a calcium salt hydrate thereof], dipeptidyl-peptidase IV inhibitors (e.g., Vildagliptin, Sitagliptin, Saxagliptin, T-6666, and TS-021), β3 agonists (e.g., AJ-9677), GPR40 agonist, GLP-1 receptor agonists [e.g., GLP-1, GLP-1MR agent, N,N-2211, AC-2993 (exendin-4), BIM-51077, Aib (8,35) hGLP-1 (7,37)NH$_2$, and CJC-1131], amyrin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, and glucagon antagonists), SGLUT (sodium-glucose cotransporter) inhibitors (e.g., T-1095), 11β-hydroxysteroid dehydrogenase inhibitors (e.g., BVT-3498), adiponectin or adiponectin agonists, IKK inhibitors (e.g., AS-2868), leptin resistance-improving drugs, somatostatin receptor agonists, glucokinase activators (e.g., Ro-28-1675), and GIP (glucose-dependent insulinotropic peptide).

Examples of the "agents for treating diabetic complications" include aldose reductase inhibitors (e.g., tolrestat, epalrestat, zenarestat, zopolrestat, minalrestat, fidarestat, and ranirestat), neurotrophic factors and neurotrophic factor-increasing drugs (e.g., NGF, NT-3, BDNF, neurotrophic factor production-secretion promoters described in WO01/14372 (e.g., 4-(4-chlorophenyl)-2-(2-methyl-1-imidazolyl)-5-[3-(2-methylphenoxy)propyl]oxazole)), PKC inhibitors (e.g., ruboxistaurin mesylate), AGE inhibitors (e.g., ALT946, pimagedine, N-phenacylthiazolium bromide, EXO-226, pyridorin, and pyridoxamine), active oxygen scavengers (e.g., thioctic acid), cerebral vasodilators (e.g., tiapride and mexiletine), somatostatin receptor agonists (e.g., BIM23190), apoptosis signal regulating kinase-1 (ASK-1) inhibitors, and neuronal regeneration promoters (e.g., Y-128, VX-853, and prosaptide).

Examples of the "antiobesity agents" include central antiobesity agents (e.g., dexfenfluramine, fenfluramine, phentermine, sibutramine, amfepramone, dexamphetamine, mazindol, phenylpropanolamine, and clobenzorex; neuropeptide Y antagonists (e.g., CP-422935); cannabinoid receptor antagonists (e.g., SR-141716 and SR-147778); ghrelin antagonists; 11β-hydroxysteroid dehydrogenase inhibitors (e.g., BVT-3498), pancreatic lipase inhibitors (e.g., orlistat, cetilistat, β3 agonist (e.g., AJ-9677), peptide antifeedants (e.g., leptin, CNTF (Ciliary Neurotrophic Factor), cholecystokinin agonists (e.g., lintitript, and FPL-15849), and anorectic agents (e.g., P-57).

Examples of the "agents for treating hyperlipidemia" include HMG-CoA reductase inhibitors (e.g., pravastatin, simvastatin, lovastatin, atorvastatin, fluvastatin, rosuvastatin, pitavastatin, and their salts (e.g., sodium salts and calcium salts)), squalene synthase inhibitors (e.g., the compounds described in WO 97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]

acetyl]piperidine-4-acetic acid), fibrate compounds (e.g., bezafibrate, clofibrate, simfibrate, and clinofibrate), ACAT inhibitors (e.g., avasimibe, and eflucimibe), anion exchange resins (e.g., colestyramine), probucol, nicotinic acid drugs (e.g., nicomol and niceritrol), ethyl icosapentate, and phytosterols (e.g., soysterol and γ-oryzanol).

The timing of administration of the concomitant drug is not limited. The compound of the present invention and the concomitant drug may be administered to the subject simultaneously, or separately at staggered intervals. The dosage of the concomitant drug may be determined based on the dose clinically used, and can be appropriately selected depending on the administration subject, administration route, disease, combination, etc.

The mode of administration of the concomitant drug with the compound of the present invention is not particularly limited, insofar as the compound of the present invention and the concomitant drugs are administered in combination. Examples of the mode of administration are as follows:

(1) administration of a single preparation obtained by simultaneously formulating the compound of the present invention with the concomitant drug;
(2) simultaneous administration of two kinds of preparations, which are obtained by separately formulating the compound of the present invention and the concomitant drug, by a single administration route;
(3) staggered-interval administration of two kinds of preparations, which are obtained by separately formulating the compound of the present invention and the concomitant drug, by the same administration route;
(4) simultaneous administration of two kinds of preparations, which are obtained by separately formulating the compound of the present invention and the concomitant drug, by different administration routes; and
(5) staggered-interval administration of two kinds of preparations, which are obtained by separately formulating the compound of the present invention and the concomitant drug, by different administration routes (for example, administration in the order of the compound of the present invention and the concomitant drug, or in the reverse order).

The mixing ratio of the compound of the present invention and the concomitant drug can be appropriately selected according to the administration subject, administration route, disease, etc.

The compound of the present invention can be concurrently used with diet therapy (e.g., diet therapy for diabetes) and/or exercise therapy.

BRIEF DESCRIPTION OF DRAWINGS

FIG. 1-2 is a graph showing inhibition of 125I-NMU8 binding when NMU derivative or a PEG conjugate (Compound C, D, or E) is added at different concentrations to FM3 membrane fraction.

FIG. 1-3 is a graph showing inhibition of $^{125}$I-NMU8 binding when NMU derivative or a PEG conjugate (Compound F, G, H, I, or J) is added at different concentrations to FM3 membrane fraction.

FIG. 1-4 is a graph showing inhibition of $^{125}$I-NMU8 binding when NMU derivative or a PEG conjugate (Compound K) is added at different concentrations to FM3 membrane fraction.

FIG. 1-5 is a graph showing inhibition of $^{125}$I-NMU8 binding when NMU derivative or a PEG conjugate (Compound L, M, or N) is added at different concentrations to FM3 membrane fraction.

FIG. 1-6 is a graph showing inhibition of $^{125}$I-NMU8 binding when NMU derivative or a PEG conjugate (Compound O, P, Q, or R) is added at different concentrations to FM3 membrane fraction.

FIG. 1-7 is a graph showing inhibition of $^{125}$I-NMU8 binding when NMU derivative or a PEG conjugate (Compound S, T, U, or V) is added at different concentrations to FM3 membrane fraction.

FIG. 2-1 is a graph showing inhibition of $^{125}$I-NMU8 binding when NMU derivative or a PEG conjugate (Compound A or B) is added at different concentrations to TGR1 membrane fraction.

FIG. 2-2 is a graph showing inhibition of $^{125}$I-NMU8 binding when NMU derivative or a PEG conjugate (Compound C, D, or E) is added at different concentrations to TGR1 membrane fraction.

FIG. 2-3 is a graph showing inhibition of $^{125}$I-NMU8 binding when NMU derivative or a PEG conjugate (Compound F, G, H, I, or J) is added at different concentrations to TGR1 membrane fraction.

FIG. 2-4 is a graph showing inhibition of $^{125}$I-NMU8 binding when NMU derivative or a PEG conjugate (Compound K) is added at different concentrations to TGR1 membrane fraction.

FIG. 2-5 is a graph showing inhibition of $^{125}$I-NMU8 binding when NMU derivative or a PEG conjugate (Compound L, M, or N) is added at different concentrations to TGR1 membrane fraction.

FIG. 2-6 is a graph showing inhibition of $^{125}$I-NMU8 binding when NMU derivative or a PEG conjugate (Compound O, P, Q, or R) is added at different concentrations to TGR1 membrane fraction.

FIG. 2-7 is a graph showing inhibition of $^{125}$I-NMU8 binding when NMU derivative or a PEG conjugate (Compound S, T, U, or V) is added at different concentrations to TGR1 membrane fraction.

FIG. 3 is a graph showing the change in the food intake in mice when NMU-PEGylated form (100 nmol/kg) is subcutaneously administered to mice in a fasting and refeeding test (Compounds A, B).

FIG. 4 is a graph showing the change in the food intake in mice when NMU-PEGylated form (100 nmol/kg) is subcutaneously administered to mice in a fasting and refeeding test (Compounds C to E).

FIG. 5 is a graph showing the change in the food intake in mice when NMU-PEGylated form (100 nmol/kg) is subcutaneously administered to mice in a fasting and refeeding test (Compounds F to J).

FIG. 6 is a graph showing the change in the food intake in mice when NMU-PEGylated form is subcutaneously administered to mice in a fasting and refeeding test (Compounds C, J).

FIG. 7 is a graph showing the change in the food intake in mice when NMU-PEGylated form is subcutaneously administered to mice in a fasting and refeeding test (Compound K).

EXAMPLES

Figure 1:
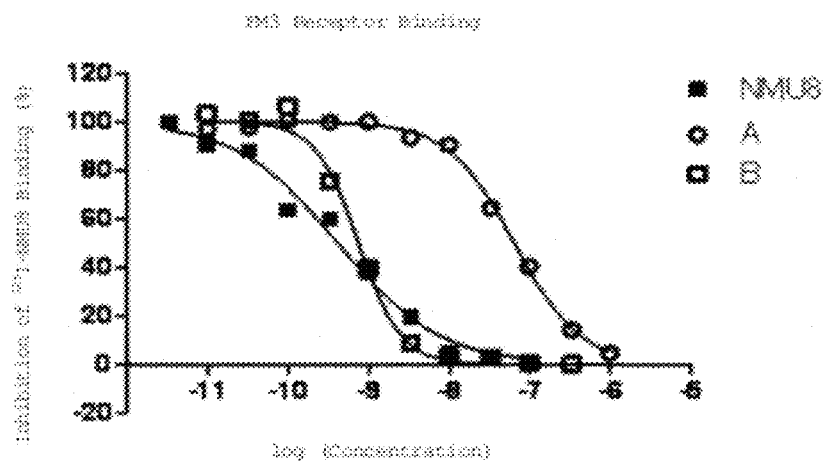
FIG. 1-1 is a graph showing inhibition of $^{125}$I-NMU8 binding when NMU derivative or a PEG conjugate (Compound A or B) is added at different concentrations to FM3 membrane fraction.

Hereinafter, the present invention is described with reference to Test Examples, Reference Examples, and Examples. However, the present invention is not limited thereto.

In the Examples, SEQ ID NO.: 1 or the peptide of SEQ ID NO.: 1 is sometimes expressed as NMU-8.

The number shown after an amino acid represents the amino acid number. The amino acid numbers in SEQ ID NO.: 1 are shown below. Specifically, the position of Tyr at the N-terminus of NMU-8 is regarded as 1 and the position of Asn at the C-terminus is regarded as 8.

```
Tyr-Phe-Leu-Phe-Arg-Pro-Arg-Asn-NH2
 1   2   3   4   5   6   7   8
```

For example, β-Ala0,Gln5-NMU-8, i.e., Compound 1 (Reference Example 1), represents a peptide in which β-Ala is extended to the N-terminus (position 0) of NMU-8, and Arg at position 5 is replaced by Gln.

Note that the above is a convenient notation; the β-Ala is a linker, and does not form the polypeptide used in the present invention.

The following are the compounds used in the Test Examples, Reference Examples, and Examples. The base sequences of the polypeptide moieties in the chemical formulae are shown above as SEQ ID NOs.: 2 to 20.

Here, the carboxyl group at the α-position of β-Ala is bound to the amino group (amino group at the α-position) of the amino acid residue at the N-terminus of the peptide used in the present invention. Further, the "—NH$_2$" indicates that the —OH in the carboxyl group (—COOH) of the amino acid residue at the C-terminus of the peptide used in the present invention is replaced by —NH$_2$.

(Compound 1)
β-Ala0, Gln5-NMU-8
β-Ala-Tyr-Phe-Leu-Phe-Gln-Pro-Arg-Asn-NH$_2$
SEQ ID NO: 2

(Compound 2)
β-Ala0, Gln3-NMU-8
β-Ala-Tyr-Phe-Gln-Phe-Arg-Pro-Arg-Asn-NH$_2$
SEQ ID NO: 3

(Compound 3)
β-Ala0, Arg3-NMU-8
β-Ala-Tyr-Phe-Arg-Phe-Arg-Pro-Arg-Asn-NH$_2$
SEQ ID NO: 4

(Compound 4)
β-Ala0, Val3-NMU-8
β-Ala-Tyr-Phe-Val-Phe-Arg-Pro-Arg-Asn-NH$_2$
SEQ ID NO: 5

(Compound 5)
β-Ala0, Tyr2-NMU-8
β-Ala-Tyr-Tyr-Leu-Phe-Arg-Pro-Arg-Asn-NH$_2$
SEQ ID NO: 6

(Compound 6)
β-Ala0, Cha3-NMU-8
β-Ala-Tyr-Phe-Cha-Phe-Arg-Pro-Arg-Asn-NH$_2$
SEQ ID NO: 7

(Compound 7)
β-Ala0, Arg1-NMU-8
β-Ala-Arg-Phe-Leu-Phe-Arg-Pro-Arg-Asn-NH$_2$
SEQ ID NO: 8

(Compound 8)
β-Ala0, Pro1-NMU-8
β-Ala-Pro-Phe-Leu-Phe-Arg-Pro-Arg-Asn-NH$_2$
SEQ ID NO: 9

(Compound 9)
Arg3-NMU-8
Tyr-Phe-Arg-Phe-Arg-Pro-Arg-Asn-NH$_2$
SEQ ID NO: 4

(Compound 10)
NpipAc-Arg3-NMU-8
NpipAc-Tyr-Phe-Arg-Phe-Arg-Pro-Arg-Asn-NH$_2$
SEQ ID NO: 4

(Compound 11)
NpipAc0, Phe1, Trp2, Ala6-NMU-8
NpipAc-Phe-Trp-Leu-Phe-Arg-Ala-Arg-Asn-NH$_2$
SEQ ID NO: 10

(Compound 12)
β-Ala0, Asp8-NMU-8
β-Ala-Tyr-Phe-Leu-Phe-Arg-Pro-Arg-Asp-NH$_2$
SEQ ID NO: 11

(Compound 13)
β-Ala0, NMeArg5-NMU-8
β-Ala-Tyr-Phe-Leu-Phe-NMeArg-Pro-Arg-Asn-NH$_2$
SEQ ID NO: 12

(Compound 14)
β-Ala0, Arg(Me)7-NMU-8
β-Ala-Tyr-Phe-Leu-Phe-Arg-Pro-Arg(Me)-Asn-NH$_2$
SEQ ID NO: 13

(Compound 15)
β-Ala0, NMeLeu3, NMeArg7-NMU-8
β-Ala-Tyr-Phe-NMeLeu-Phe-Arg-Pro-NMeArg-Asn-NH$_2$
SEQ ID NO: 14

(Compound 16)
β-Ala0, NMeTyr1, NMeLeu3, NMeArg5-NMU-8
β-Ala-NMeTyr-Phe-NMeLeu-Phe-NMeArg-Pro-Arg-Asn-NH$_2$
SEQ ID NO: 15

(Compound 17)
β-Ala0, Trp2, NMeAla6-NMU-8
β-Ala-Tyr-Trp-Leu-Phe-Arg-NMeAla-Arg-Asn-NH$_2$
SEQ ID NO: 16

(Compound 18)
β-Ala0, Glu2, NMeAla6-NMU-8
β-Ala-Tyr-Glu-Leu-Phe-Arg-NMeAla-Arg-Asn-NH$_2$
SEQ ID NO: 17

(Compound 19)
NpipAc0, Glu2, Ala6-NMU-8
NpipAc-Tyr-Glu-Leu-Phe-Arg-Ala-Arg-Asn-NH$_2$
SEQ ID NO: 18

(Compound 20)
NpipAc0, Trp2, Ala6-NMU-8
NpipAc-Tyr-Trp-Leu-Phe-Arg-Ala-Arg-Asn-NH$_2$
SEQ ID NO: 19

-continued
(Compound 21)
NpipAc0, Glu2, NMeAla6-NMU-8
NpipAc-Tyr-Glu-Leu-Phe-Arg-NMeAla-Arg-Asn-NH$_2$
SEQ ID NO: 17
(Compound 22)
NpipAc0, Nal(2)2, NMeAla6-NMU-8
NpipAc-Tyr-Nal(2)-Leu-Phe-Arg-NMeAla-Arg-Asn-NH$_2$
SEQ ID NO: 20
PEG30k-NH-β-Ala0, Gln5-NMU-8
PEG30K-NH-β-Ala-Tyr-Phe-Leu-Phe-Gln-Pro-Arg-Asn-NH$_2$
SEQ ID NO: 2
(Compound A)
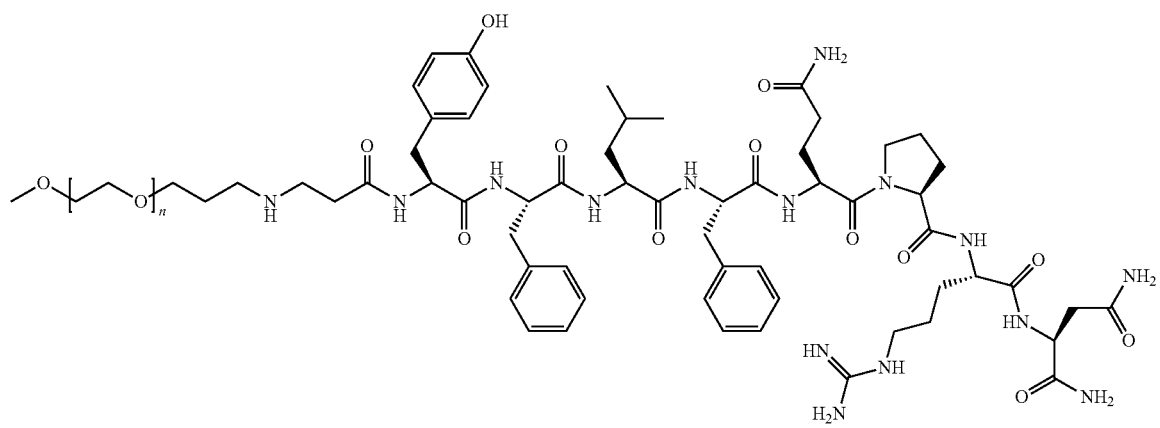
PEG30K-NH-β-Ala0, Gln3-NMU-8
PEG30K-NH-β-Ala-Tyr-Phe-Gln-Phe-Arg-Pro-Arg-Asn-NH$_2$
SEQ ID NO: 3
(Compound B)
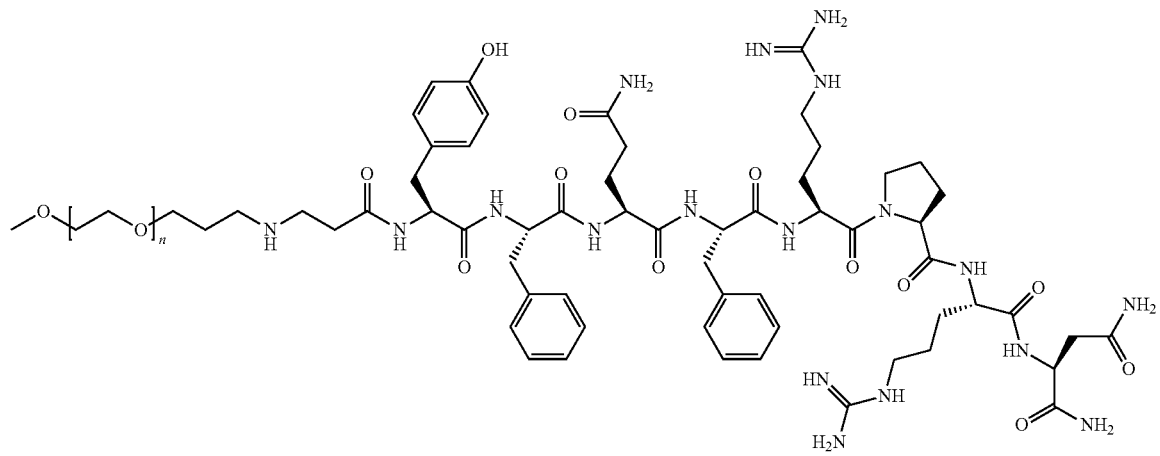

PEG30K-NH-β-Ala0, Arg3-NMU-8
PEG30K-NH-β-Ala-Tyr-Phe-Arg-Phe-Arg-Pro-Arg-Asn-NH₂
SEQ ID NO: 4
(Compound C)
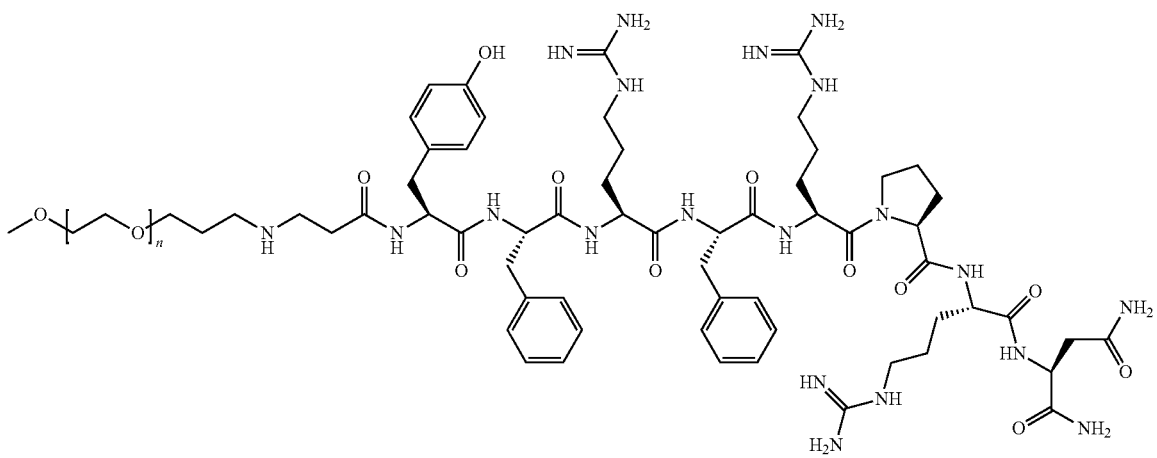
PEG30K-NH-β-Ala0, Val3-NMU-8
PEG30K-NH-β-Ala-Tyr-Phe-Val-Phe-Arg-Pro-Arg-Asn-NH₂
SEQ ID NO: 5
(Compound D)
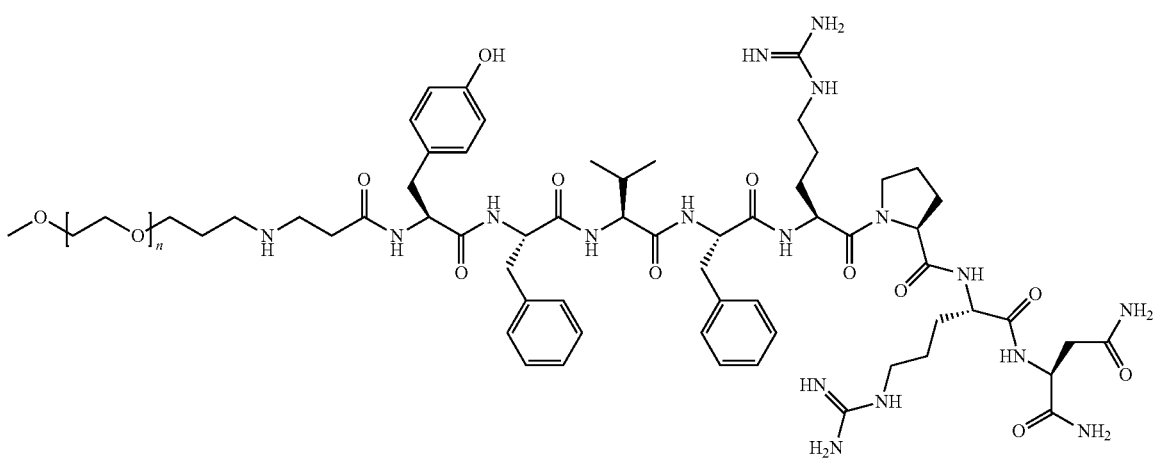
PEG30K-NH-β-Ala0, Tyr2-NMU-8
PEG30K-NH-β-Ala-Tyr-Tyr-Leu-Phe-Arg-Pro-Arg-Asn-NH₂
SEQ ID NO: 6
(Compound E)
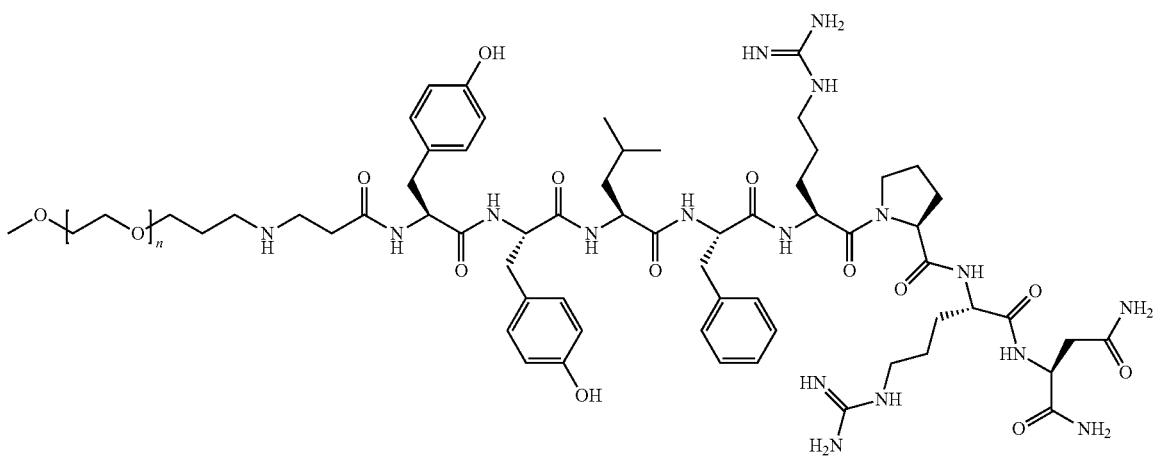

(Compound F)
PEG30K-NH-β-Ala0, Cha3-NMU-8
PEG30K-NH-β-Ala-Tyr-Phe-Cha-Phe-Arg-Pro-Arg-Asn-NH$_2$
SEQ ID NO: 7
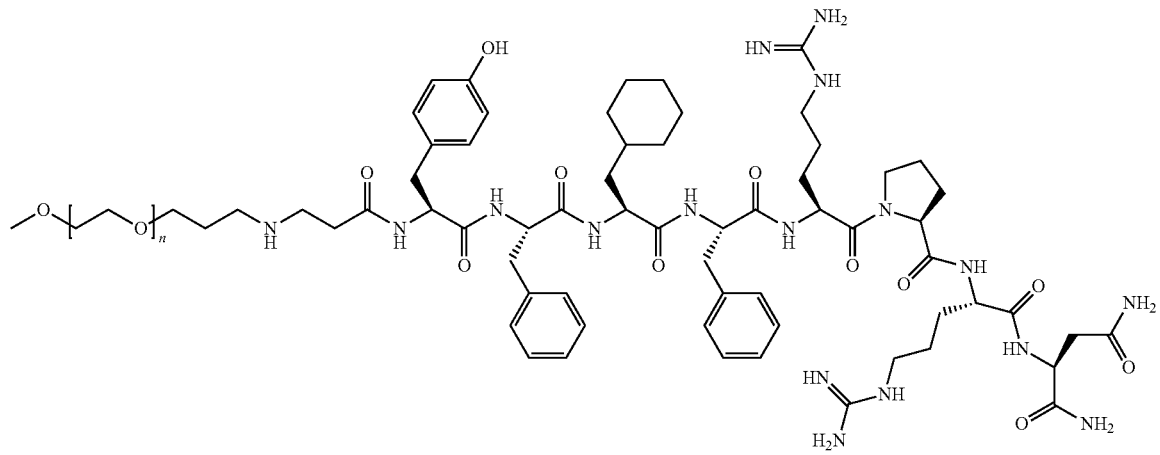
(Compound G)
PEG30K-NH-β-Ala0, Arg1-NMU-8
PEG30K-NH-β-Ala-Arg-Phe-Leu-Phe-Arg-Pro-Arg-Asn-NH$_2$
SEQ ID NO: 8
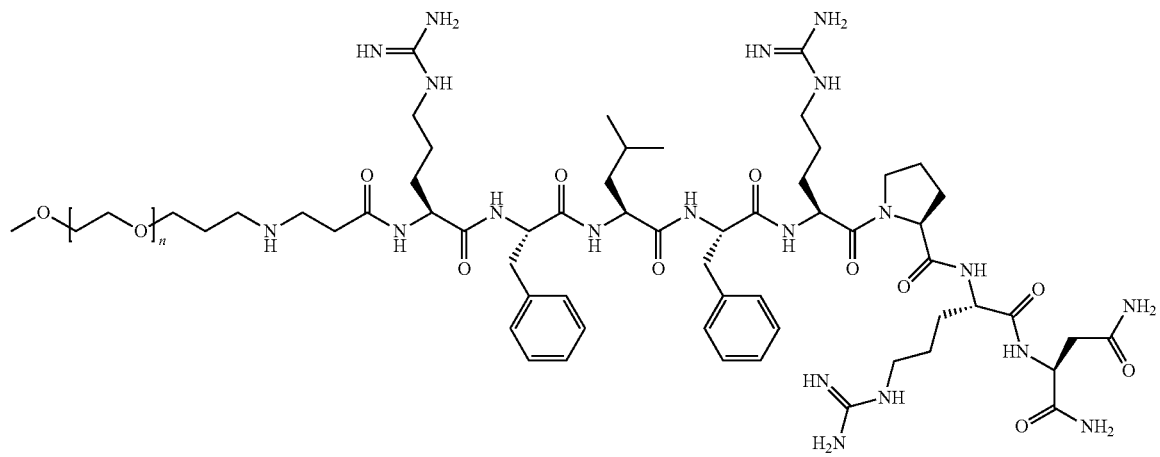
(Compound H)
PEG30K-NH-β-Ala0, Pro1-NMU-8
PEG30K-NH-β-Ala-Pro-Phe-Leu-Phe-Arg-Pro-Arg-Asn-NH$_2$
SEQ ID NO: 9
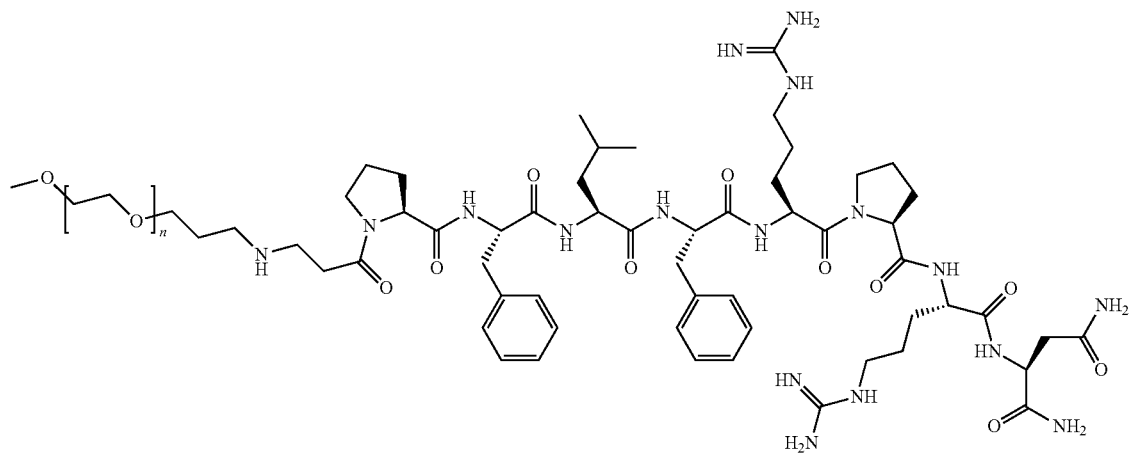

-continued
(Compound I)
PEG20k-NpipAc0, Arg3-NMU-8
PEG20k-NpipAc-Tyr-Phe-Arg-Phe-Arg-Pro-Arg-Asn-NH$_2$
SEQ ID NO: 4
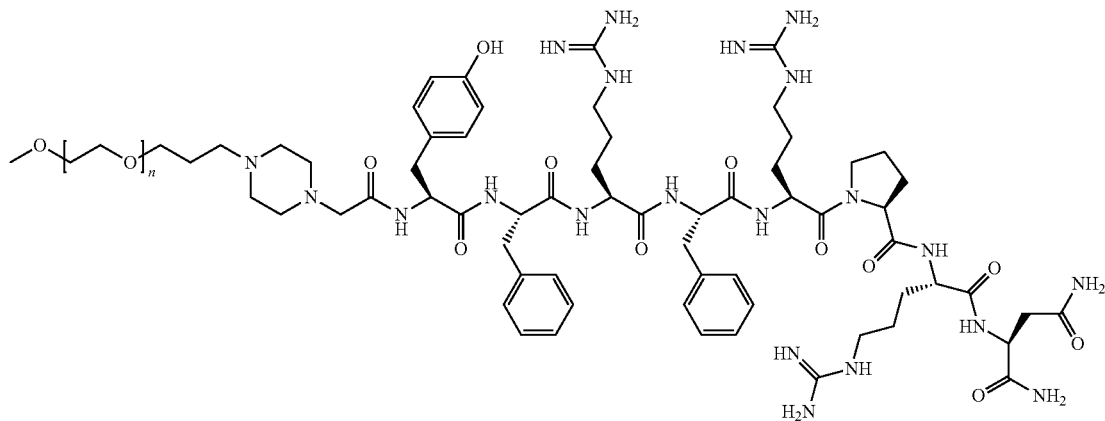
(Compound J)
PEG30k-NpipAc0, Arg3-NMU-8
PEG30k-NpipAc-Tyr-Phe-Arg-Phe-Arg-Pro-Arg-Asn-NH$_2$
SEQ ID NO: 4
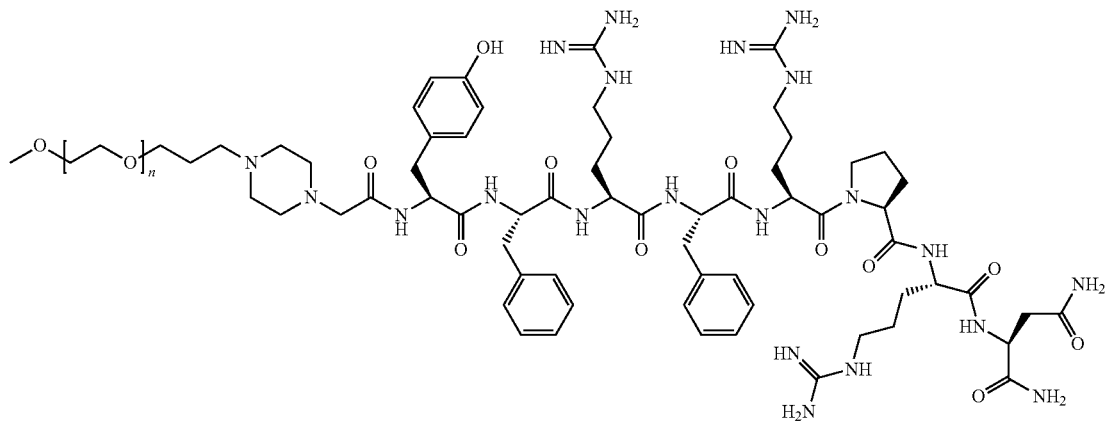
(Compound K)
PEG20k-NpipAc0, Phe1, Trp2, Ala6-NMU-8
PEG20k-NpipAc-Phe-Trp-Leu-Phe-Arg-Ala-Arg-Asn-NH$_2$
SEQ ID NO: 10
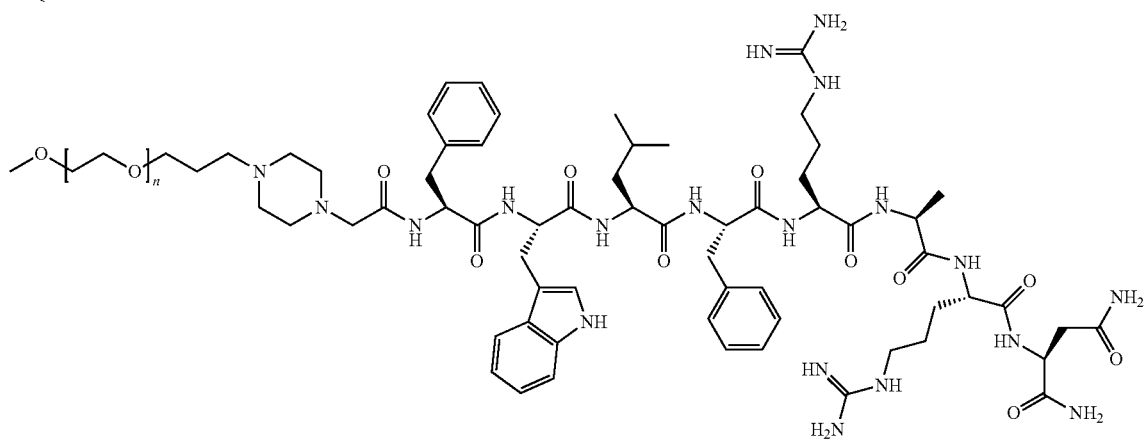

(Compound L)
PEG30k-NH-β-Ala0, Asp8-NMU-8
PEG30k-NH-β-Ala-Tyr-Phe-Leu-Phe-Arg-Pro-Arg-Asp-NH₂
SEQ ID NO: 11
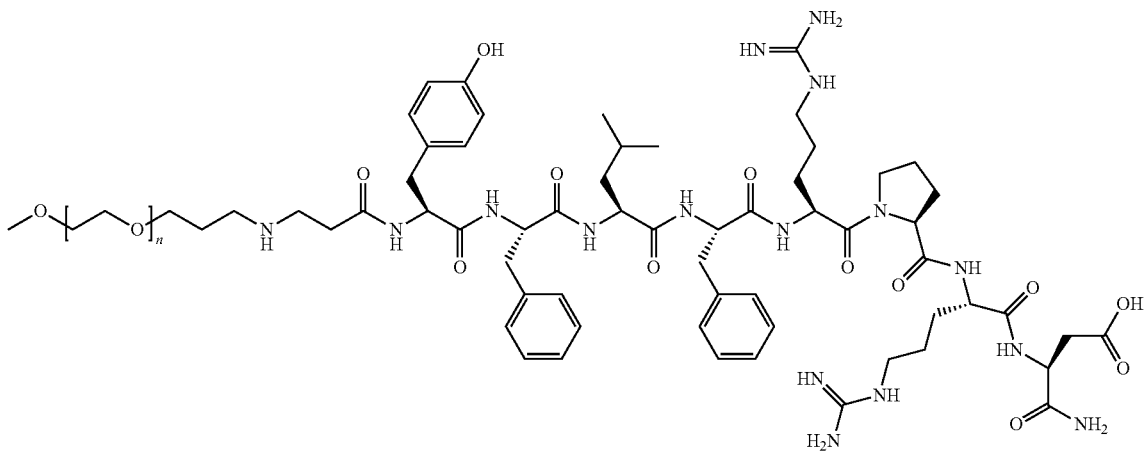
(Compound M)
PEG30k-NH-β-Ala0, NMeArg5-NMU-8
PEG30k-NH-β-Ala-Tyr-Phe-Leu-Phe-NMeArg-Pro-Arg-Asn-NH₂
SEQ ID NO: 12
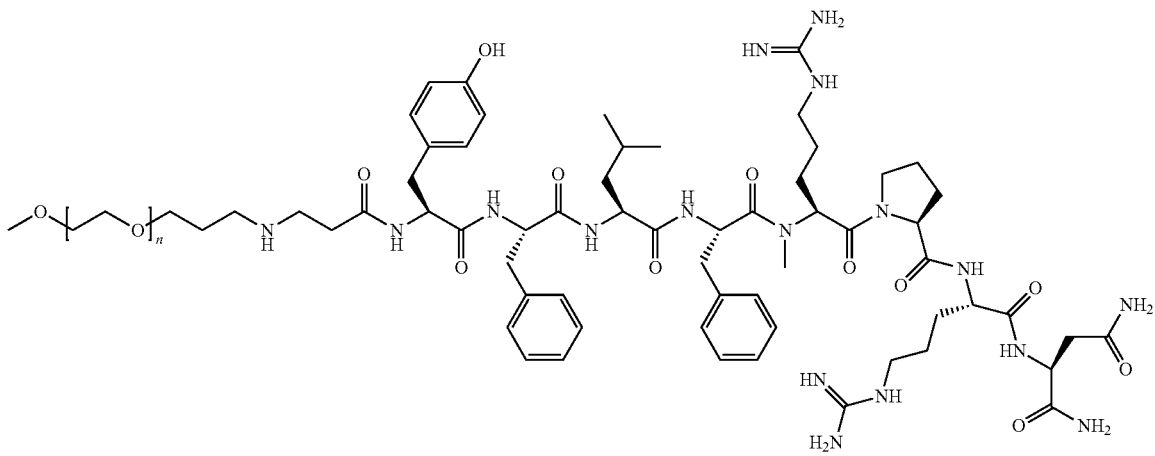
(Compound N)
PEG30k-NH-β-Ala0, Arg(Me)7-NMU-8
PEG30k-NH-β-Ala-Tyr-Phe-Leu-Phe-Arg-Pro-Arg(Me)-Asn-NH₂
SEQ ID NO: 13
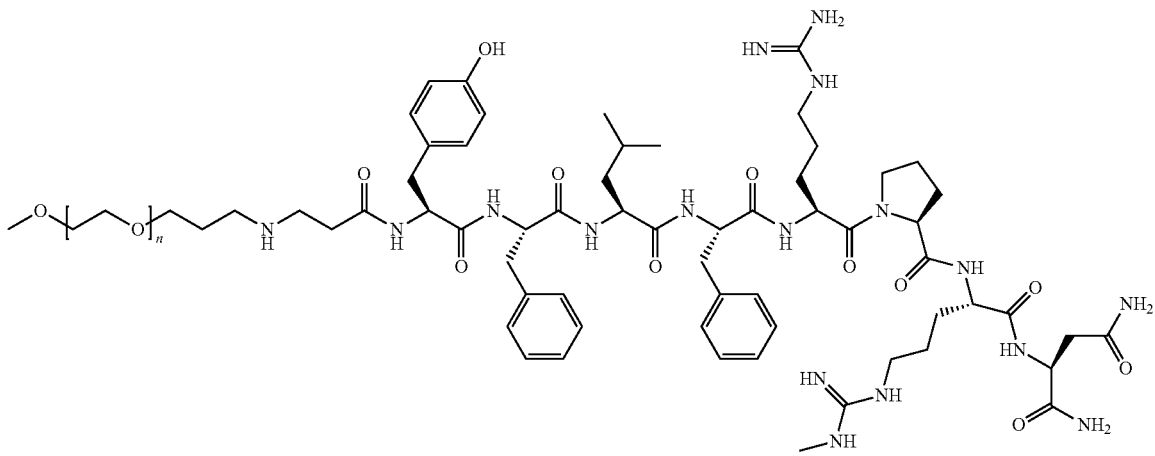

-continued
PEG20k-NH-β-Ala0, NMeLeu3, NMeArg7-NMU-8
PEG20k-NH-β-Ala-Tyr-Phe-NMeLeu-Phe-Arg-Pro-NMeArg-Asn-NH₂
SEQ ID NO: 14
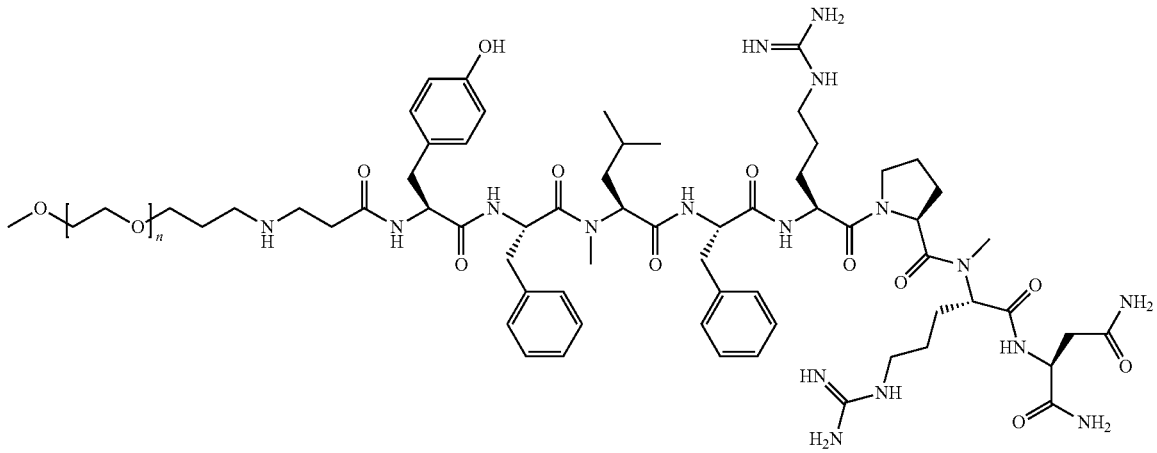
(Compound O)
PEG20k-NH-β-Ala0, NMeTyr1, NMeLeu3, NMeArg5-NMU-8
PEG20k-NH-β-Ala-NMeTyr-Phe-NMeLeu-Phe-NMeArg-Pro-Arg-Asn-NH₂
SEQ ID NO: 15
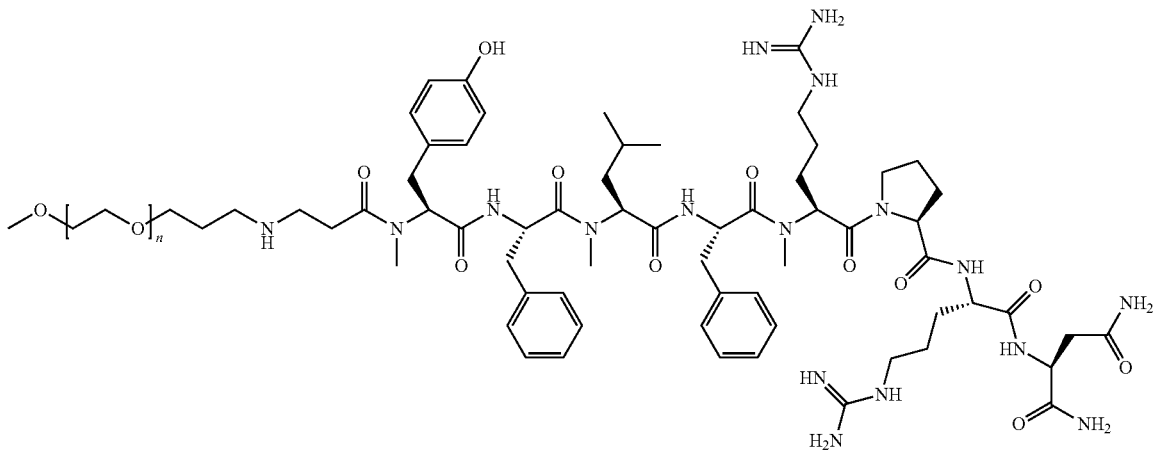
(Compound P)
PEG20k-NH-β-Ala0, Trp2, NMeAla6-NMU-8
PEG20k-NH-β-Ala-Tyr-Trp-Leu-Phe-Arg-NMeAla-Arg-Asn-NH₂
SEQ ID NO: 16
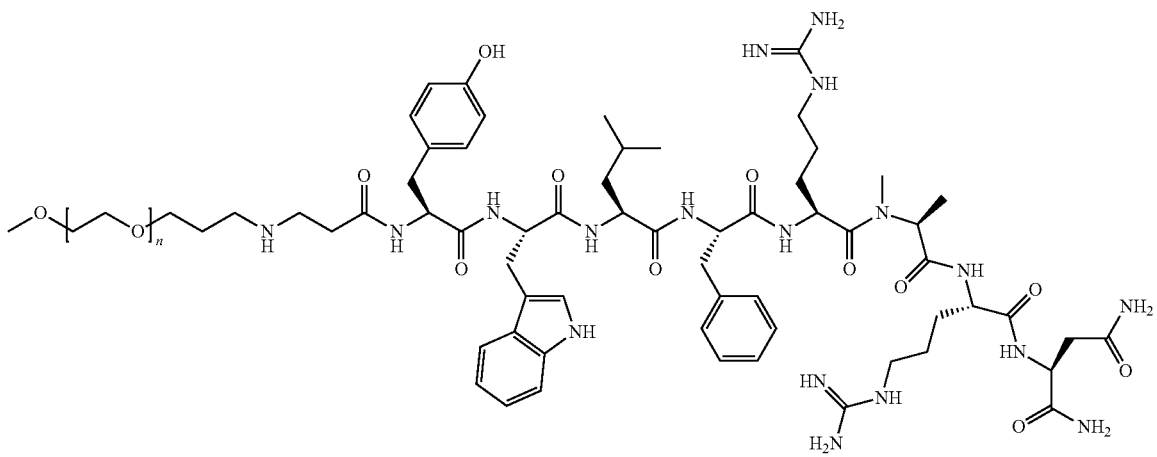
(Compound Q)

(Compound R)
PEG20k-NH-β-Ala0, Glu2, NMeAla6-NMU-8
PEG20k-NH-β-Ala-Tyr-Glu-Leu-Phe-Arg-NMeAla-Arg-Asn-NH₂
SEQ ID NO: 17
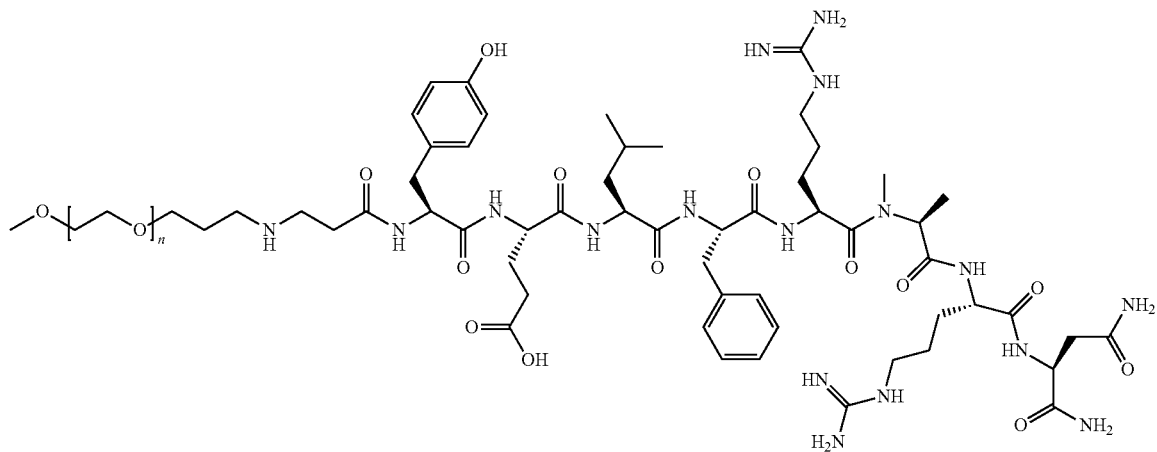
(Compound S)
PEG20k-NpipAc0, Glu2, Ala6-NMU-8
PEG20k-NpipAc-Tyr-Glu-Leu-Phe-Arg-Ala-Arg-Asn-NH₂
SEQ ID NO: 18
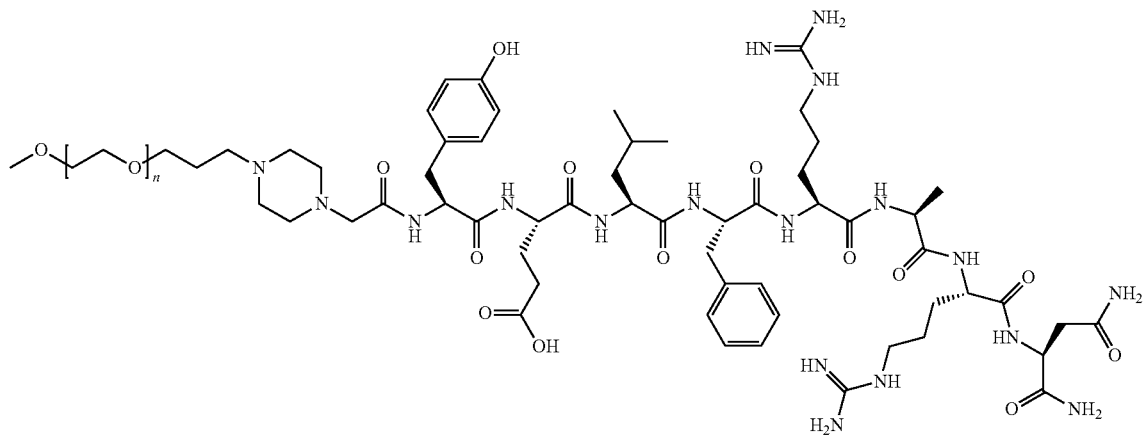
(Compound T)
PEG20k-NpipAc0, Trp2, Ala6-NMU-8
PEG20k-NpipAc-Tyr-Trp-Leu-Phe-Arg-Ala-Arg-Asn-NH₂
SEQ ID NO: 19
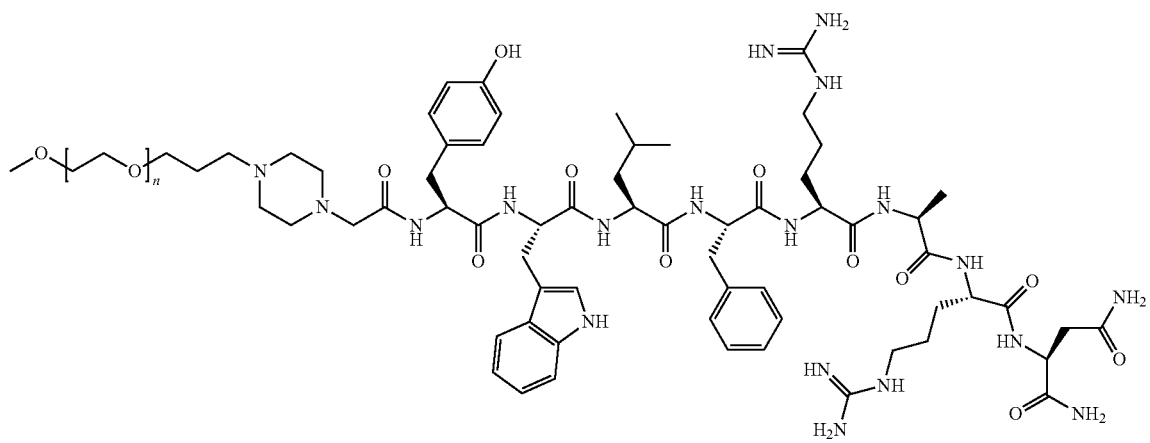

-continued (Compound U)
PEG20k-NpipAc0, Glu2, NMeAla6-NMU-8
PEG20k-NpipAc-Tyr-Glu-Leu-Phe-Arg-NMeAla-Arg-Asn-NH$_2$
SEQ ID NO: 17

(Compound V)
PEG20k-NpipAc0, Nal(2)2, NMeAla6-NMU-8
PEG20k-NpipAc-Tyr-Nal(2)-Leu-Phe-Arg-NMeAla-Arg-Asn-NH$_2$
SEQ ID NO: 20

The abbreviations used herein indicate the following:
Abbreviation: Name
Ac: acetyl
Abu: 2-aminobutanoic acid
AcOEt: ethyl acetate
AcOH: acetic acid
Aib: α-aminoisobutanoic acid
Arg(Me): N$^\omega$-methylarginine
Arg(Pbf): N$^\omega$-2,2,4,6,7-pentamethyldihydrobenzofuran-sulfonyl arginine
β-Ala: β-alanine
Boc: tert-butoxycarbonyl
Bu$^t$: tert-butyl
Bzl: benzyl
Cha: β-cyclohexylalanine
Dbu: 2,4-diaminobutanoic acid
DCM: dichloromethane
DEA: diethylamine
DIEA: N,N-diisopropylethylamine
DIPCDI: 1,3-diisopropylcarbodiimide
DMAP: 4-dimethylaminopyridine
DMF: N,N-dimethylformamide
EDT: 1,2-ethanedithiol
Fmoc: 9-fluorenylmethoxycarbonyl
HOAt: 1-hydroxy-7-aza-benzotriazole
HOBt: 1-hydroxybenzotriazole
HOOBt: 3,4-dihydro-3-hydroxy-4-oxo-1,2,3-benzotriazine
HONB: N-hydroxy-5-norbornene-2,3-dicarboxylmide
Hse: homoserine
Hyp: trans-4-hydroxyproline
Leu(Me): γ-methylleucine
MBHA: p-methylbenzhydrylamine
MeOH: methanol
αMePhe: C$^\alpha$-methylphenylalanine
Nal(1): 1-naphthylalanine
Nal(2): 2-naphthylalanine
Nle: norleucine
NMeAla: N$^\alpha$-methylalanine
NMeArg: N$^\alpha$-methylarginine
NMeAsn: N$^\alpha$-methylasparagine
NMeLeu: N$^\alpha$-methylleucine
NMePhe: N$^\alpha$-methylphenylalanine
NMeSer: N$^\alpha$-methylserine
NMeTyr: N$^\alpha$-methyltyrosine
NpipAc: 2-(piperazin-1-yl)acetyl
OBu$^t$: tert-butoxy Orn: ornithine
Pbf: 2,2,4,6,7-pentamethyldihydrobenzofuran-5-sulfonyl
Phe(4F): 4-fluorophenylalanine
PhOH: phenol
PhSMe: thioanisole
Pya(4): 4-pyridylalanine
PyAOP: (7-azabenzotriazol-1-yloxy)-tris(pyrrolidino)phosphonium hexafluorophosphate
PyBOP: (benzotriazol-1-yloxy)-tris(pyrrolidino)phosphonium hexafluorophosphate
PyBrop: bromo-tris(pyrrolidino)phosphonium hexafluorophosphate
MeGly: N-methylglycine
TIS: triisopropylsilane
Trt: trityl
TFA: trifluoroacetic acid
TFE: trifluoroethanol
Tyr($PO_3H_2$): O-phosphotyrosine
Z: benzyloxycarbonyl Reference Example 1

Synthetic Method A

Production of β-Ala0,Gln5-NMU-8 (Compound 1)

425 mg of Fmoc-NH-SAL resin (Watanabe Chemical Industries, Ltd., 0.59 mmol/g) was used as a starting material, and Fmoc-amino acids were sequentially condensed in accordance with a general Fmoc strategy (HBTU/HOBt) using a Model 433A Peptide Synthesizer (produced by Applied Biosystems). Thereby, 881 mg of β-Ala-Tyr($Bu^t$)-Phe-Leu-Phe-Gln(Trt)-Pro-Arg(Pbf)-Asn(Trt)-NH-SAL resin was obtained. Then, 7.94 mL of TFA/TIS/$H_2O$ (95:2.5:2.5) was added to the obtained peptide resin, treated at room temperature for 2 hours, and precipitated with diethyl ether, making the crude peptide into a white powder. The obtained crude peptide was purified by preparative HPLC using an ODS column (Shimadzu LC-8A System, YMC-Pack ODS-A, 30×250 mm). Linear density gradient elution (80 minutes) was performed at a flow rate of 20 mL/min. with Solution A (0.1% TFA-water)/Solution B (0.1% TFA-containing acetonitrile): 85.3/14.7 to 65.3/34.7. The elution fractions containing a target product were collected, concentrated, and freeze-dried to yield 107 mg of a white powder.
Mass spectrum $(M+H)^+$ 1154.6 (Calcd.: 1154.6)
HPLC elution time: 13.8 minutes
Elution Conditions
  Column: Wakosil-II 5C18 HG (4.6×100 mm)
  Eluant: Solution A: 0.1% TFA-water; Solution B: 0.1% TFA-containing acetonitrile, linear density gradient elution (25 minutes) performed with Solution A/Solution B: 100/0 to 50/50
  Flow rate: 1.0 mL/min.

Reference Example 2

Synthetic Method B

Production of β-Ala0,Arg1-NMU-8 (Compound 7)

391 mg of Sieber amide resin (Nova, 0.64 mmol/g) was used as a starting material, and Fmoc-amino acids were sequentially condensed in accordance with a general Fmoc strategy (DCC/HOBt) using a Model 433A Peptide Synthesizer (produced by Applied Biosystems). Thereby, 763 mg of Phe-Leu-Phe-Arg(Pbf)-Pro-Arg(Pbf)-Asn(Trt)-NH-Sieber amide resin was obtained. Then, 61.1 mg (0.02 mmol) of the obtained resin was washed with DMF, swollen in DMF, and then treated for 120 minutes with 51.9 mg (0.08 mmol) of Fmoc-Arg (Pbf), 0.16 mL (0.08 mmol) of 0.5 M HOAt/DMF solution, and 13.9 μL (0.08 mmol) of DIPCDI, thereby introducing Arg(Pbf) residue. After completion of the reaction, the resin was washed and then treated with 20% piperidine/DMF to remove the N-terminus Fmoc group. In a manner similar to that above, Boc-β-Ala was introduced. Then, 0.6 mL of TFA:thioanisole:m-cresol:$H_2O$:EDT:TIS (80:5:5:5:2.5:2.5) was added to the obtained peptide resin, treated at room temperature for 90 minutes, and precipitated with diethyl ether, making the crude peptide into a white powder. The obtained crude peptide was purified by preparative HPLC using an ODS column (Shimadzu LC-8A System, Daisopak-SP100-5-ODS-P, 20×250 mm). Linear density gradient elution (120 minutes) was performed at a flow rate of 15 mL/min. with Solution A (0.1% TFA-water)/Solution B (0.1% TFA-containing acetonitrile): 88/12 to 68/32. The elution fractions containing a target product were collected, concentrated, and freeze-dried to yield 11.2 mg of a white powder.
Mass spectrum $(M+H)^+$ 1175.5 (Calcd. 1175.7)
HPLC elution time: 10.6 minutes
Elution Conditions
  Column: Wakosil-II 5C18 HG (4.6×100 mm)
  Eluant: Solution A: 0.1% TFA-water; Solution B: 0.1% TFA-containing acetonitrile, linear density gradient elution (25 minutes) performed with Solution A/Solution B: 100/0 to 50/50
  Flow rate: 1.0 ml/min.

Reference Example 3

Synthetic Method C

Production of 2-(piperazin-1-yl)acetyl-Arg3-NMU8 (Compound 10)

9 μmol (10.6 mg) of Arg3-NMU8 (Compound 9) was dissolved in 1,000 μL of dimethylformamide. To this solution, a solution obtained by adding 13.5 μmol of diethyl cyanophosphate and 36 μmol of triethylamine to a solution previously prepared by dissolving an amount equivalent to 18 μmol of 2-(4-tert-butoxycarbonylpiperazin-1-yl)acetic acid (Fluorochem Ltd.) in 500 μL of dimethylformamide was added to perform a reaction at room temperature for 1 hour. After the reaction solution was evaporated, the resulting product was dissolved in 100 μL of distilled water. Then, 1.9 mL of trifluoroacetic acid was added thereto to perform a reaction at room temperature for 30 minutes, thereby removing the Boc group. The reaction solution was diluted 15-fold with diethyl ether, and thoroughly mixed. Thereafter, the mixture was centrifuged for 15 minutes at 3,000 rpm at 4° C. The supernatant was discarded by decantation, and 15 mL of diethyl ether was added to the pellets again and mixed thoroughly. Subsequently, the same procedure was repeated. The obtained pellets were dried at room temperature, and dissolved in 6 mL of 0.1 M acetic acid. The resulting solution was injected at a flow rate of 30.0 mL/min. into a CAPCELL PAK CN column (UG120, 30×250 mm, Shiseido Co., Ltd.) equilibrated with Solution A and Solution B (0.1% trifluoroacetic acid/80% acetonitrile) at a ratio of 100%/0%. After the concentration was rapidly elevated to Solution A/Solution B: 85%/15%, the concentration was further elevated linearly to Solution A/Solution B: 45%/55% during a period of 40 minutes. Thereby, 2-(piperazin-1-yl)acetyl-$Arg^3$-NMU8 was eluted. Then, the peaks of the target product were fractionated, and the product was freeze-dried.

Reference Example 4

Compounds 2 to 6, Compounds 8-9, and Compounds 11-22 were synthesized in a manner similar to the methods of Reference Examples 1 to 3.

Table 1 (Tables 1-1 and 1-2) below indicates each of the synthetic methods.

Example 1

Synthetic Method D

Preparation of NMU Derivative-PEG Conjugate using PEG-Aldehyde (1)

2.0 μmol each of the NMU-8 derivatives (β-Ala0,Gln5-NMU-8; β-Ala0,Gln3-NMU-8; β-Ala0,Arg3-NMU-8; β-Ala0,Val3-NMU-8; β-Ala0,Cha3-NMU-8; β-Ala0,Tyr2-NMU-8; β-Ala0,Arg1-NMU-8; and β-Ala0,Pro1-NMU-8) and 4.0 μmol (~120 mg) of aldehyde group-containing PEG (SUNBRIGHT ME-300AL, Nippon Oil & Fats Co., Ltd.) were dissolved in 1,000 μL of dimethylformamide, and an amount equivalent to 40 μmol of sodium cyanotrihydroborate was added thereto to perform a reaction at room temperature for 2 hours.

Acetic acid was added to the reaction solution to a final concentration of 0.1 M. Then, the resulting solution was diluted with 40 mL of 0.1 M acetic acid and loaded into an SP-Sephadex C50 ion exchange column (capacity: 10 mL). After rinsing the column with 0.1 M acetic acid, and then with 10 mM ammonium formate/0.1 M acetic acid, a NMU-8 derivative-PEG conjugate was eluted from the column with 2 M ammonium formate/20% acetonitrile, and then with 3.2 M ammonium formate/20% acetonitrile.

The obtained eluate was injected at a flow rate of 30.0 mL/min. into a CAPCELL PAK CN column (UG120, 30×250 mm, Shiseido Co., Ltd.) equilibrated with Solution A and Solution B at a ratio of 100%/0%. After the concentration was rapidly elevated to Solution A/Solution B: 55%/45%, the concentration was further elevated linearly to Solution A/Solution B: 15%/85% during a period of 40 minutes. Thereby, a NMU-8 derivative-PEG conjugate was eluted. The peaks of the NMU-8 derivative-PEG conjugates (PEG30k-NH-β-Ala0,Gln5-NMU-8 (Compound A), PEG30k-NH-β-Ala0,Gln3-NMU-8 (Compound B), PEG30k-NH-β-Ala0,Arg3-NMU-8 (Compound C), PEG30k-NH-β-Ala0,Val3-NMU-8 (Compound D), PEG30k-NH-β-Ala0,Tyr2-NMU-8 (Compound E), PEG30k-NH-β-Ala0,Cha3-NMU-8 (Compound F), PEG30k-NH-β-Ala0,Arg1-NMU-8 (Compound G), and PEG30k-NH-β-Ala0,Pro1-NMU-8 (Compound H)) were fractionated, and the resulting products were freeze-dried.

Each of the obtained freeze-dried NMU-8-PEG conjugates was dissolved in distilled water, and the peptide concentration was determined by amino acid analysis.

Example 2

Synthetic Method E

Preparation of NMU Derivative-PEG Conjugate using PEG-Aldehyde (2)

2.0 μmol of 2-(piperazin-1-yl)acetyl-Arg3-NMU8 (Compound 10) and 4.0 μmol (~120 or 80 mg) of aldehyde group-containing PEG (SUNBRIGHT ME-200AL or SUNBRIGHT ME-300AL, Nippon Oil & Fats Co., Ltd.) were dissolved in 1,000 μL of dimethylformamide, and an amount equivalent to 40 μmol of sodium cyanotrihydroborate was added thereto to perform a reaction at room temperature for 2 hours. Acetic acid was added to the reaction solution to a final concentration of 0.1 M. Then, the resulting solution was diluted with 40 mL of 0.1 M acetic acid and loaded into an SP-Sephadex C50 ion exchange column (capacity: 10 mL). After rinsing the column with 0.1 M acetic acid, and then with 10 mM ammonium formate/0.1 M acetic acid, a NMU-8 derivative-PEG conjugate was eluted from the column with 2 M ammonium formate/20% acetonitrile, and then with 3.2 M ammonium formate/20% acetonitrile.

The obtained eluate was injected at a flow rate of 30.0 mL/min into a CAPCELL PAK CN column (UG120, 30×250 mm, Shiseido Co., Ltd.) equilibrated with Solution A and Solution B at a ratio of 100%/0%. After the concentration was rapidly elevated to Solution A/Solution B: 55%/45%, the concentration was further elevated linearly to Solution A/Solution B: 15%/85% during a period of 40 minutes. Thereby, a NMU-8 derivative-PEG conjugate was eluted. The peaks of NMU-8 derivative-PEG conjugates (PEG20k-NpipAc-Arg3-NMU-8 (Compound I) and PEG30k-NpipAc-Arg3-NMU-8 (Compound J)) were fractionated, and the resulting products were freeze-dried.

Example 3

Synthetic Method F

Preparation of NMU Derivative-PEG Conjugate using PEG-Aldehyde (3)

4.0 μmol each of the NMU-8 derivatives (β-Ala0,Asp8-NMU-8; β-Ala0,NMeArg5-NMU-8; β-Ala0,Arg(Me)7-NMU-8; p-Ala0,NMeLeu3,NMeArg7-NMU-8; β-Ala0, NMeTyr1,NMeLeu3,NMeArg5-NMU-8; β-Ala0,Trp2, NMeAla6-NMU-8; and β-Ala0,Glu2,NMeAla6-NMU-8) and 6.0 μmol (~180 mg or 120 mg) of aldehyde group-containing PEG (SUNBRIGHT ME-300AL or ME-200AL, Nippon Oil, & Fats Co., Ltd.) were dissolved in 1,000 μL of dimethylformamide, and an amount equivalent to 80 μmol of sodium cyanotrihydroborate was added thereto to perform a reaction at room temperature for 2 hours. Acetic acid was added to the reaction solution to a final concentration of 0.1 M. Then, the resulting solution was diluted with 40 mL of 0.1 M acetic acid and loaded into an SP-Sephadex C50 ion exchange column (capacity: 10 mL). After rinsing the column with 0.1 M acetic acid, and then with 10 mM ammonium formate/0.1 M acetic acid, a NMU-8 derivative-PEG conjugate was eluted from the column with 2 M ammonium formate/20% acetonitrile, and then with 3.2 M ammonium formate/20% acetonitrile.

The obtained eluate was injected at a flow rate of 30.0 mL/min into a CAPCELL PAK CN column (UG120, 30×250 mm, Shiseido Co., Ltd.) equilibrated with Solution A and Solution B at a ratio of 100%/0%. After the concentration was rapidly elevated to Solution A/Solution B: 60%/40%, the concentration was further elevated linearly to Solution A/Solution B: 20%/80% during a period of 40 minutes. Thereby, a NMU-8 derivative-PEG conjugate was eluted. The peaks of the NMU-8 derivative-PEG conjugates (PEG30k-NH-β-Ala0,Asp8-NMU-8 (Compound L), PEG30k-NH-β-Ala0, NMeArg5-NMU-8 (Compound M), PEG30k-NH-β-Ala0, Arg(Me) 7-NMU-8 (Compound N), PEG20k-NH-β-Ala0, NMeLeu3,NMeArg7-NMU-8 (Compound O), PEG20k-NH- β-Ala0,NMeTyr1,NMeLeu3,NMeArg5-NMU-8 (Compound P), PEG20k-NH-β-Ala0,Trp2,NMeAla6-NMU-8 (Compound Q), and PEG20k-NH-β-Ala0,Glu2,NMeAla6-NMU-8 (Compound R)) were fractionated, and the resulting products were further freeze-dried.

Example 4

Synthetic Method G

Preparation of NMU Derivative-PEG Conjugate using PEG-Aldehyde (4)

4.0 μmol each of 2-(piperazin-1-yl)acetyl-[Phe1,Trp2,Ala6]-NMU-8, 2-(piperazin-1-yl)acetyl-[Glu2,Ala6]-NMU8, 2-(piperazin-1-yl)acetyl-[Trp2,Ala6]-NMU8, 2-(piperazin-1-yl)acetyl-[Glu2,NMeAla6]-NMU8, and 2-(piperazin-1-yl)acetyl-[Nal(2)2,NMeAla6]-NMU8, and 6.0 μmol (~120 mg) of aldehyde group-containing PEG (SUNBRIGHT ME-200AL, Nippon Oil & Fats Co., Ltd.) were dissolved in 1,000 μL of dimethylformamide, and an amount equivalent to 80 μmol of sodium cyanotrihydroborate was added thereto to perform a reaction at room temperature for 2 hours. Acetic acid was added to the reaction solution to a final concentration of 0.1 M. Then, the resulting solution was diluted with 40 mL of 0.1 M acetic acid and loaded into an SP-Sephadex C50 ion exchange column (capacity: 10 mL). After rinsing the column with 0.1 M acetic acid, and then with 10 mM ammonium formate/0.1 M acetic acid, a NMU-8 derivative-PEG conjugate was eluted from the column with 2 M ammonium formate/20% acetonitrile, and then with 3.2 M ammonium formate/20% acetonitrile.

The obtained eluate was injected at a flow rate of 30.0 mL/min into a CAPCELL PAK CN column (UG120, 30×250 mm, Shiseido Co., Ltd.) equilibrated with Solution A and Solution B at a ratio of 100%/0%. After the concentration was rapidly elevated to Solution A/Solution B: 60%/40%, the concentration was further elevated linearly to Solution A/Solution B: 20%/80% during a period of 40 minutes. Thereby, a NMU-8 derivative-PEG conjugate was eluted. The peaks of NMU-8 derivative-PEG conjugates (PEG20k-NPipAc-Phe1,Trp2,Ala6-NMU-8 (Compound K), PEG20k-NpipAc-Glu2,Ala6-NMU8 (Compound S), PEG20k-NpipAc-Trp2,Ala6-NMU8 (Compound T), PEG20k-NpipAc-Glu2,NMeAla6-NMU8 (Compound U), and PEG20k-NpipAc-Nal(2)2,NMeAla6-NMU8 (Compound V)) were fractionated, and the resulting products were freeze-dried.

Table 1 below shows the structure, physicochemical properties, etc., of each of the compounds synthesized above.

The column titled "Synthetic Method" in the table shows that the compounds described in Reference Examples 1 to 3 were synthesized by the synthetic methods a, b, or c, and that the compounds not described in Reference Examples 1 to 3 were synthesized in a manner similar to the synthetic method a, b, or c.

The column titled "Analysis Condition" in the table shows the following HPLC analysis conditions h, i, j, k, l, m, or n:

h: Wakosil-II 5C18 HG 4.6×100 mm; gradient: 0-50% B (A: DW/0.1% TFA, B: 100% AcCN/0.1% TFA), 0-25 min., 1 mL/min.

i: CAPCELL PAK UG120, CN 30×250 mm; gradient: 20-60% B (A: DW/0.1% TFA, B: 80% AcCN/0.1% TFA), 3-43 min., 30 mL/min.

j: Merck Chromolith Performance RP-18e 4.6×100 mm; gradient: 5-65% B (A: DW/0.1% TFA, B:100% AcCN/0.1% TFA), 0-10 min., 3 mL/min.

k: CAPCELL PAK UG120, C1 30×250 mm; gradient: 40-80% B (A: DW/0.1% TFA, B: 80% AcCN/0.1% TFA), 6-46 min., 30 mL/min.

l: CAPCELL PAK UG120, CN 30×250 mm; gradient: 40-80% B (A: DW/0.1% TFA, B:80% AcCN/0.1% TFA), 3-43 min., 30 mL/min.

m: CAPCELL PAK UG120, CN 30×250 mm; gradient: 45-85% B (A: DW/0.1% TFA, B: 80% AcCN/0.1% TFA), 3-43 min., 30 mL/min.

n: CAPCELL PAK UG120, CN 50×250 mm, and gradient 40-80% B (A:DW/0.1% TFA, B:80% AcCN/0.1% TFA), 10-50 min., 60 mL/min.

TABLE 1-1

| Compound No. | Structure | M + H$^+$ (obs.) | M + H$^+$ (cal.) | HPLC (min.) | Synthetic Method | Analysis Condition |
|---|---|---|---|---|---|---|
| 1 | β-Ala0,Gln5-NMU-8 | 1154.6 | 1154.6 | 13.8 | a | h |
| 2 | β-Ala0,Gln3-NMU-8 | 1197.5 | 1197.6 | 11.7 | a | h |
| 3 | β-Ala0,Arg3-NMU-8 | 1225.4 | 1225.7 | 11.0 | a | h |
| 4 | β-Ala0,Val3-NMU-8 | 1168.4 | 1168.6 | 12.4 | a | h |
| 5 | β-Ala0,Try2-NMU-8 | 1198.5 | 1198.6 | 12.0 | a | h |
| 6 | β-Ala0,Cha3-NMU-8 | 1222.4 | 1222.7 | 15.0 | a | h |
| 7 | β-Ala0,Arg1-NMU-8 | 1175.5 | 1175.7 | 10.6 | b | h |
| 8 | β-Ala0,Pro1-NMU-8 | 1116.6 | 1116.6 | 12.2 | b | h |
| 9 | Arg3-NMU-8 | 1154.5 | 1154.6 | 10.3 | b | h |
| 10 | NpipAc-Arg3-NMU-8 | 1281.1 | 1280.7 | 10.8 | c | i |
| 12 | β-Ala0,Asp8-NMU-8 | 1183.5 | 1183.6 | 13.2 | a | h |
| 13 | β-Ala0,NMeArg5-NMU-8 | 1196.7 | 1196.7 | 13.4 | a | h |
| 14 | β-Ala0,Arg(Me)7-NMU-8 | 1196.6 | 1196.7 | 13.0 | a | h |
| 15 | β-Ala0,NMeLeu3,NMeArg7-NMU-8 | 1210.6 | 1210.7 | 13.5 | a | h |
| 16 | β-Ala0,NMeTry1,NMeLeu3,NMEArg5-NMU-8 | 1224.3 | 1224.7 | 14.9 | a | h |
| 17 | β-Ala0,Trp2,NMeAla6-NMU-8 | 1209.7 | 1209.7 | 4.7 | a | j |
| 18 | β-Ala0,Glu2,NMeAla6-NMU-8 | 1152.6 | 1152.6 | 3.9 | a | j |
| 19 | NpipAc0,Glu2,Ala6-NMU-8 | 1193.6 | 1193.7 | 3.8 | a | j |
| 20 | NpipAc0,Trp2,Ala6-NMU-8 | 1250.6 | 1250.7 | 4.7 | a | j |
| 21 | NpipAc0,Glu2,NMeAla6-NMU-8 | 1207.6 | 1207.7 | 3.9 | a | j |
| 22 | NpipAc0,Nal(2)2,NMeAla6-NMU-8 | 1275.7 | 1275.7 | 5.2 | a | j |
| A | PEG-NH-β-Ala0,Gln5-NMU-8 | | | 23.6 | d | k |
| B | PEG-NH-β-Ala0,Gln3-NMU-8 | | | 23.0 | d | k |
| C | PEG-NH-β-Ala0,Arg3-NMU-8 | | | 15.4 | d | l |

TABLE 1-1-continued

| Compound No. | Structure | M + H+ (obs.) | M + H+ (cal.) | HPLC (min.) | Synthetic Method | Analysis Condition |
|---|---|---|---|---|---|---|
| D | PEG-NH-β-Ala0,Val3-NMU-8 | | | 15.6 | d | l |
| E | PEG-NH-β-Ala0,Tyr2-NMU-8 | | | 15.5 | d | l |
| F | PEG-NH-β-Ala0,Cha3-NMU-8 | | | 23.8 | d | k |
| G | PEG-NH-β-Ala0,Arg1-NMU-8 | | | 17.5 | d | l |
| H | PEG-NH-β-Ala0,Pro1-NMU-8 | | | 17.6 | d | l |
| I | PEG20k-NpipAc-Arg3-NMU-8 | | | 12.0 | e | m |
| J | PEG30k-NpipAc-Arg3-NMU-8 | | | 13.2 | e | m |
| K | PEG20k-NpipAc0,Phe1,Trp2,Ala6-NMU-8 | | | 23.7 | g | n |
| L | PEG30k-NH-β-Ala0,Asp8-NMU-8 | | | 12.6 | f | m |
| M | PEG30k-NH-β-Ala0,NMeArg5-NMU-8 | | | 12.9 | f | m |
| N | PEG30k-NH-β-Ala0,Arg(Me)7-NMU-8 | | | 12.7 | f | m |
| O | PEG20k-NH-β-Ala0,NMeLeu3,NMeArg7-NMU-8 | | | 18.7 | f | l |
| P | PEG20k-NH-β-Ala0,NMeTyr1,NMeLeu3,NMeArg5-NMU-8 | | | 19.2 | f | l |
| Q | PEG20k-NH-β-Ala0,Trp2,NMeAla6-NMU-8 | | | 18.6 | f | l |
| R | PEG20k-NH-β-Ala0,Glu2,NMeAla6-NMU-8 | | | 19.0 | f | l |
| S | PEG20k-NpipAc0,Glu2,Ala6-NMU-8 | | | 18.8 | g | l |
| T | PEG20k-NpipAc0,Trp2,Ala6-NMU-8 | | | 19.3 | g | l |
| U | PEG20k-NpipAc0,Glu2,NMeAla6-NMU-8 | | | 18.9 | g | l |
| V | PEG20k-NpipAc0,Nal(2)2,NMeAla6-NMU-8 | | | 19.3 | g | l |

Test Example 1

Receptor Binding Test of NMU-8 Derivative and PEG Conjugate

CHO cells expressing Human FM3 (dhfr-) and CHO cells expressing human TGR1 (dhfr-) were cultured in 10% dialyzed FBS-containing MEMα (Invitrogen) medium under conditions of 5% carbon dioxide at 37° C. The adherent cells were detached with 10 mL of 0.1 mM EDTA-containing D-PBS (Invitrogen) and centrifuged for 10 minutes at 1,000 rpm at 4° C., thereby collecting the cells. 15 mL of homogenized buffer (10 mM NaHCO₃ (pH 7.4), 5 mM EDTA, protease inhibitor=0.5 mM PMSF, 10 μg/mL Pepstatin A, 20 μg/mL Leupeptin, and 4 μg/mL E-64) was added to the obtained cell pellets, the cellular membrane was disrupted using a polytron homogenizer (Kinematica GmbH), centrifugation was conducted for 10 minutes at 1,000 g at 4° C., and the supernatant was collected. This process was further repeated twice, and ultracentrifugation was conducted for 60 minutes at 30,000 rpm at 4° C. Thereafter, 8 mL of homogenized buffer was added to the pellets and suspended homogeneously to prepare a membrane fraction. The protein concentration of the FM3-expressing CHO cellular membrane fraction was 1.2 mg/mL, and the protein concentration of the TGR1-expressing CHO cellular membrane fraction was 1.1 mg/mL.

Figures 1, 2:
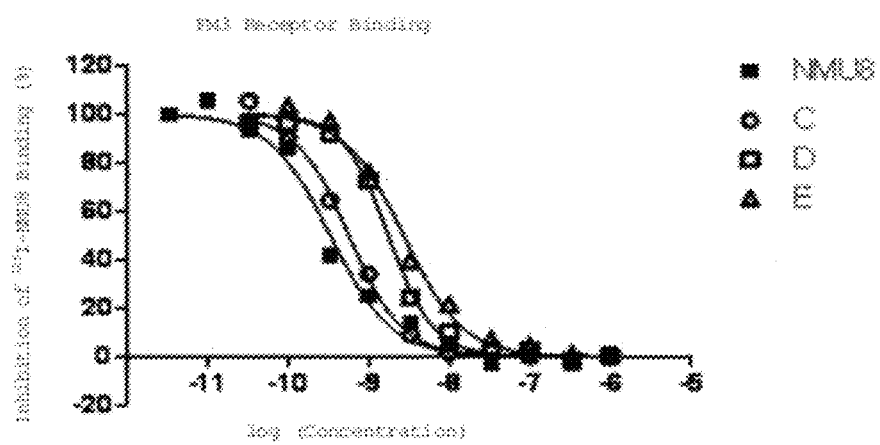

The affinity of the NMU-8 derivatives and PEG conjugates shown in Table 2 (Table 2-1 and Table 2-2) with respect to each receptor was evaluated based on the inhibition of $^{125}$I-NMU8 labeled ligand binding to the FM3 membrane fraction or to the TGR1 membrane fraction. Specifically, each of the NMU derivatives and PEG conjugates was dissolved in DMSO so as to prepare 2 μL of each dilution series of the NMU derivatives and PEG conjugates. Then, 100 μL of membrane fraction solutions diluted with a reaction buffer (50 mM HEPES, 1 mM EDTA protease inhibitor (0.5 mM PMSF), 10 μg/mL Pepstatin A, 20 μg/mL Leupeptin, and 4 μg/mL E-64, pH 6.8, 0.1% BSA) was added thereto, followed by further addition of 100 μL of the labeled ligand (final concentration: 135 pM) similarly diluted with the reaction buffer. The resulting product was thoroughly mixed, and then a reaction was carried out at 25° C. for 70 minutes. In accordance with the above-described procedure, the binding amount of the labeled ligand remaining in the filter was measured using a top count (PerkinElmer) by a liquid scintillation method, and the IC₅₀ values were calculated using a Graph Pad Prism (FIG. 1 (FM3 receptor binding), FIG. 2 (TGR1 receptor binding), and Table 2). In FIGS. 1 and 2, the horizontal axis indicates logarithmic values of the concentration of each derivative, and the vertical axis indicates the percentage inhibition of binding of each derivative, normalized with 0% to 100% residual radioactivity, calculated based on the binding of NMU-8. Table 2 shows the ratios of IC₅₀ values when the affinity of NMU-8 was 1.

TABLE 2-1

| Compound No. | Structure | FM3 Receptor Binding IC₅₀ ratio | TGR1 Receptor Binding IC₅₀ ratio |
|---|---|---|---|
| 1 | β-Ala0,Gln5-NMU-8 | 15 | 3.4 |
| 2 | β-Ala0,Gln3-NMU-8 | 0.31 | 3.9 |
| 3 | β-Ala0,Arg3-NMU-8 | 0.07 | 0.38 |
| 4 | β-Ala0,Val3-NMU-8 | 0.43 | 0.37 |
| 5 | β-Ala0,Try2-NMU-8 | 0.44 | 0.17 |
| 6 | β-Ala0,Cha3-NMU-8 | 0.55 | 9.9 |
| 7 | β-Ala0,Arg1-NMU-8 | 0.42 | 3.7 |
| 8 | β-Ala0,Pro1-NMU-8 | 0.59 | 3.8 |
| 9 | Arg3-NMU-8 | 0.62 | 1.9 |
| 10 | NpipAc-Arg3-NMU-8 | 0.27 | 0.66 |
| 11 | NpipAc0,Phe1,Trp2,Ala6-NMU-8 | 280 | 0.19 |
| 12 | β-Ala0,Asp8-NMU-8 | 2.4 | 2.0 |
| 13 | β-Ala0,NMeArg5-NMU-8 | 0.46 | 1.1 |
| 14 | β-Ala0,Arg(Me)7-NMU-8 | 6.3 | 3.6 |

TABLE 2-1-continued

| Compound No. | Structure | FM3 Receptor Binding IC$_{50}$ ratio | TGR1 Receptor Binding IC$_{50}$ ratio |
|---|---|---|---|
| 15 | β-Ala0,NMeLeu3,NMeArg7-NMU-8 | 8.6 | 19 |
| 16 | β-Ala0,NMeTry1,NMeLeu3,NMEArg5-NMU-8 | 8.5 | 27 |
| 17 | β-Ala0,Trp2,NMeAla6-NMU-8 | 92 | 1.9 |
| 18 | β-Ala0,Glu2,NMeAla6-NMU-8 | 26000 | 31 |
| 19 | NpipAc0,Glu2,Ala6-NMU-8 | 24000 | 25 |
| 20 | NpipAc0,Trp2,Ala6-NMU-8 | 900 | 1.9 |
| 21 | NpipAc0,Glu2,NMeAla6-NMU-8 | 6500 | 5.5 |
| 22 | NpipAc0,Nal(2)2,NMeAla6-NMU-8 | 99 | 1.7 |
| A | PEG-NH-β-Ala0,Gln5-NMU-8 | 160 | 9.6 |
| B | PEG-NH-β-Ala0,Gln3-NMU-8 | 1.8 | 7.3 |
| C | PEG-NH-β-Ala0,Arg3-NMU-8 | 1.7 | 2.6 |
| D | PEG-NH-β-Ala0,Val3-NMU-8 | 5.3 | 2.2 |
| E | PEG-NH-β-Ala0,Tyr2-NMU-8 | 8.1 | 1.7 |
| F | PEG-NH-β-Ala0,Cha3-NMU-8 | 1.3 | 11 |
| G | PEG-NH-β-Ala0,Arg1-NMU-8 | 1.5 | 8.5 |
| H | PEG-NH-β-Ala0,Pro1-NMU-8 | 9.4 | 21 |
| I | PEG20k-NpipAc-Arg3-NMU-8 | 1.6 | 2.1 |
| J | PEG30k-NpipAc-Arg3-NMU-8 | 2.2 | 2.6 |
| K | PEG20k-NpipAc0,Phe1,Trp2,Ala6-NMU-8 | 11000 | 34 |
| L | PEG30k-NH-β-Ala0,Asp8-NMU-8 | 150 | 34 |
| M | PEG30k-NH-β-Ala0,NMeArg5-NMU-8 | 9.0 | 29 |
| N | PEG30k-NH-β-Ala0,Arg(Me)7-NMU-8 | 290 | 63 |
| O | PEG20k-NH-β-Ala0,NMeLeu3,NMeArg7-NMU-8 | 75 | 170 |
| P | PEG20k-NH-β-Ala0,NMeTyr1,NMeLeu3,NMeArg5-NMU-8 | 83 | 240 |
| Q | PEG20k-NH-β-Ala0,Trp2,NMeAla6-NMU-8 | 1600 | 47 |
| R | PEG20k-NH-β-Ala0,Glu2-NMeAla6-NMU-8 | >7300 | 540 |
| S | PEG20k-NpipAc0,Glu2,Ala6-NMU-8 | >10000 | 750 |
| T | PEG20k-NpipAc0,Trp2,Ala6-NMU-8 | >10000 | 55 |
| U | PEG20k-NpipAc0,Glu2,NMeAla6-NMU-8 | >10000 | 360 |
| V | PEG20k-NpipAc0,Nal(2)2,NMeAla6-NMU-8 | 10000 | 27 |

Test Example 2

Anorectic Activity of NMU-8 Derivative-PEG Conjugate in Mice

Male C57BL/6J mice, seven weeks old, purchased from Charles River Laboratories Japan Inc., were housed in groups (four animals per cage) for 5 to 10 days after introduction under a rearing environment where the temperature, humidity and lighting time were adjusted (25° C., 12 hours of light period and 12 hours of dark period, light was lit at 8:00). After being handled for 5 to 8 days, the mice were housed individually in cages with mesh floors, and habituated to subcutaneous administration for 3 days prior to peptide (conjugate) administration. The habituated mice were fasted for 16 hours from 18:00 on the previous day of peptide (conjugate) administration; however, the mice had free access to drinking water. Subsequently, 100 µL each of solutions obtained by dissolving, in physiological saline, each of the PEG-NMU8 derivative conjugates, i.e., PEG30k-NH-β-Ala0,Gln5-NMU-8 (Compound A), PEG30k-NH-β-Ala0,Gln3-NMU-8 (Compound B), PEG30k-NH-β-Ala0,Arg3-NMU-8 (Compound C), PEG30k-NH-β-Ala0,Val3-NMU-8 (Compound D), PEG30k-NH-β-Ala0,Tyr2-NMU-8 (Compound E), PEG30k-NH-β-Ala0,Cha3-NMU-8 (Compound F), PEG30k-NH-β-Ala0,Arg1-NMU-8 (Compound G), PEG30k-NH-β-Ala0,Pro1-NMU-8 (Compound H), PEG20k-NpipAc-Arg3-NMU8 (Compound I), and PEG30k-NpipAc-Arg3-NMU8 (Compound J), was subcutaneously administered to the mice at 10:00 on the day of administration such that the dosage of each of the solutions was 100 nmol/kg. Immediately after the administration of the peptide (conjugate) solution, the mice were fed ad libitum with MF feed (Oriental Yeast Co., Ltd.) that had been weighed, and the residual amount of the feed was weighed after 3, 6, and 24 hours. The food intakes at 3, 6, and 24 hours were calculated by subtracting the residual amount of the feed weighed after 3, 6, and 24 hours from the amount of the feed originally given. FIGS. 3 to 6 show the results. FIG. 6 shows the results obtained when 100 µL each of the solutions of Compounds C and J was subcutaneously administered to the mice such that the dosage of each of the solutions was 30 nmol/kg.

Figures 1, 2, 3:
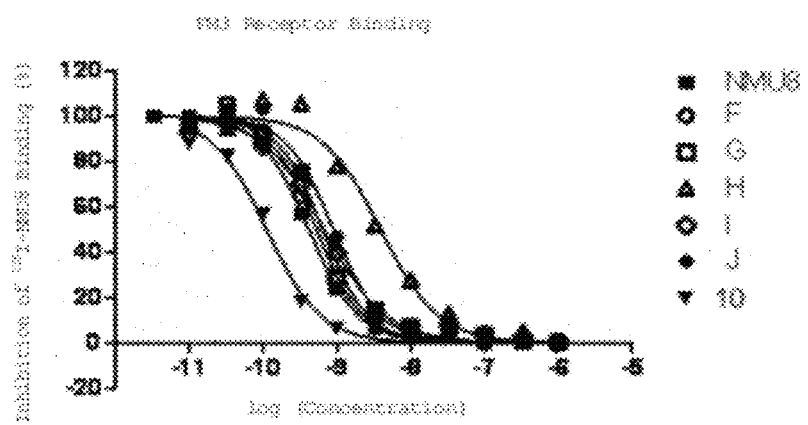

In FIG. 3, the columns represent, from left, a physiological saline, Compound A, and Compound B. The feed intakes of the NMU-PEGylated form administration groups and the feed intake of the physiological saline administration group were tested by a 2-sample test. The number of asterisks represents the following significance levels:
Significance level smaller than 0.01 (P<0.01): **
Significance level smaller than 0.001 (P<0.001): ***

Figures 1, 2, 3, 4:
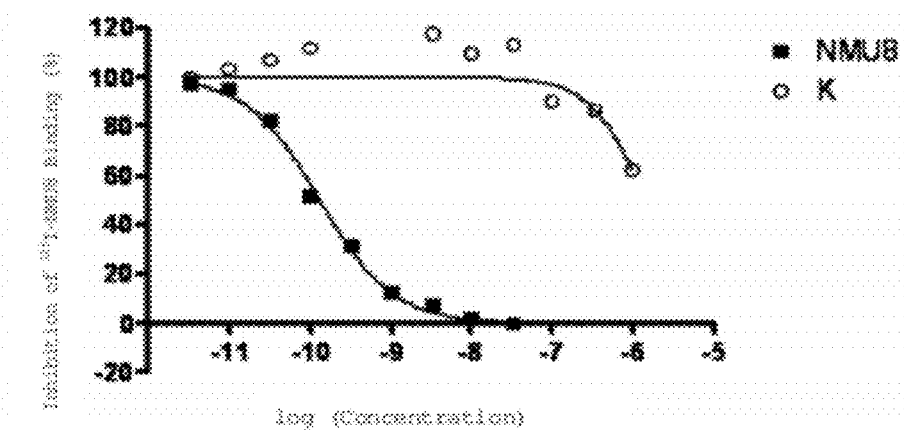

In FIG. 4, the columns represent, from left, a physiological saline, Compound C, Compound D, and Compound E. The feed intakes of the NMU-PEGylated form administration groups and the feed intake of the physiological saline administration group were tested by a 2-sample test. The number of asterisks represents the following significance levels:
Significance level smaller than 0.05 (P<0.05): *
Significance level smaller than 0.01 (P<0.01): **
Significance level smaller than 0.001 (P<0.001): ***

Figures 1, 2, 3, 4, 5:
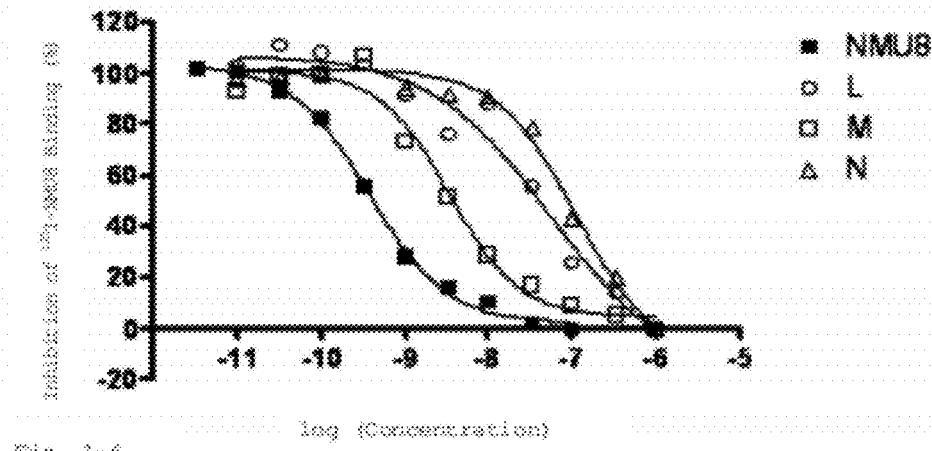
Figures 1, 2, 3, 4, 5, 6:
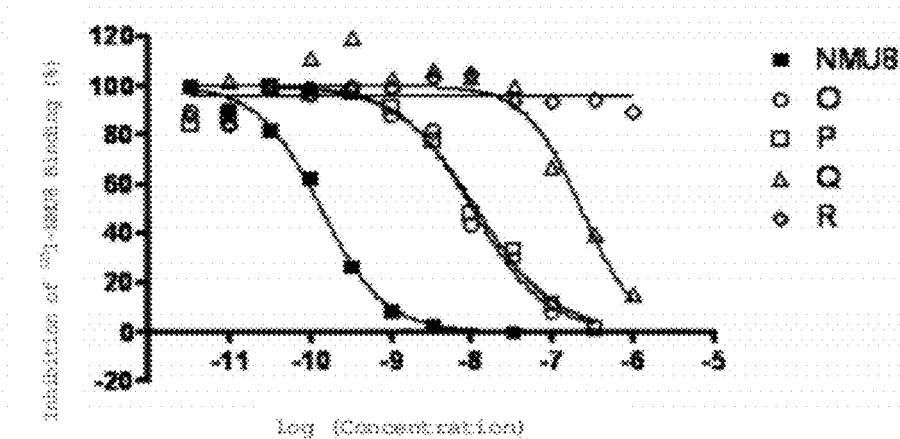

In FIG. 5, the columns represent, from left, physiological saline, Compound F, Compound G, Compound H, Compound I, and Compound J. The feed intakes of the NMU-PEGylated form administration groups and the feed intake of the physiological saline group were tested by a 2-sample test. The number of asterisks represents the significance level as follows:
Significance level smaller than 0.05 (P<0.05): *
Significance level smaller than 0.01 (P<0.01): **
Significance level smaller than 0.001 (P<0.001): ***

In FIG. 6, the columns represent, from left, physiological saline, Compound C (30 nmol/kg), Compound C (100 nmol/kg), Compound J (30 nmol/kg), and Compound J (100 nmol/kg).
# indicates that the significance level was smaller than 0.025 (P<0.025), based on William's test performed with respect to the feed intakes.

As is clear from FIGS. 3 to 6, each of the NMU-8-PEG conjugates significantly suppressed food intake in mice.

Test Example 3

Anorectic Activity of NMU-8 Derivative-PEG Conjugate in Mice (2)

Male C57BL/6J mice, six to seven weeks old, purchased from Charles River Laboratories Japan Inc., were housed in groups (four animals per cage) for 9 to 12 days after introduction under a rearing environment where the temperature, humidity and lighting time were adjusted (25° C., 12 hours of light period and 12 hours of dark period, light was lit at 8:00). After being handled for 5 to 8 days, the mice were housed individually in cages with mesh floors, and habituated to subcutaneous administration for 3 days prior to peptide (conjugate) administration. The habituated mice were fasted for 16 hours from 18:00 on the previous day of peptide (conjugate) administration; however, the mice had free access to drinking water. Subsequently, 100 μL each of solutions obtained by dissolving, in physiological saline, each of the PEG-NMU8 derivative conjugates, i.e., PEG20k-NPipAc-Phe1, Trp2,Ala6-NMU-8 (Compound K), PEG30k-NH-β-Ala0,Asp8-NMU-8 (Compound L), PEG30k-NH-β-Ala0, NMeArg5-NMU-8 (Compound M), PEG30k-NH-β-Ala0, Arg(Me)7-NMU-8 (Compound N), PEG20k-NH-β-Ala0, NMeTyr1,NMeLeu3,NMeArg5-NMU-8 (Compound P), PEG20k-NH-β-Ala0,Trp2,NMeAla6-NMU-8 (Compound Q), PEG20k-NH-β-Ala0,Glu2,NMeAla6-NMU-8 (Compound R), PEG20k-NpipAc-Glu2,Ala6-NMU8 (Compound S), PEG20k-NpipAc-Trp2,Ala6-NMU8 (Compound T), PEG20k-NpipAc-Glu2,NMeAla6-NMU8 (Compound U), and PEG20k-NpipAc-Nal(2)2,NMeAla6-NMU8 (Compound V), was subcutaneously administered to the mice at 10:00 on the day of administration such that the dosage of each of the solutions was 100 nmol/kg. Immediately after the administration of the peptide (conjugate) solution, the mice were fed ad libitum with MF feed (Oriental Yeast Co., Ltd.) that had been weighed, and the residual amount of the feed was weighed after 3, 6, and 24 hours. The food intakes at 3, 6, and 24 hours were calculated by subtracting the residual amount of the feed weighed after 3, 6, and 24 hours from the amount of the feed originally given. FIGS. 7 to 11 show the results.

Figures 1, 2, 3, 4, 5, 6, 7:
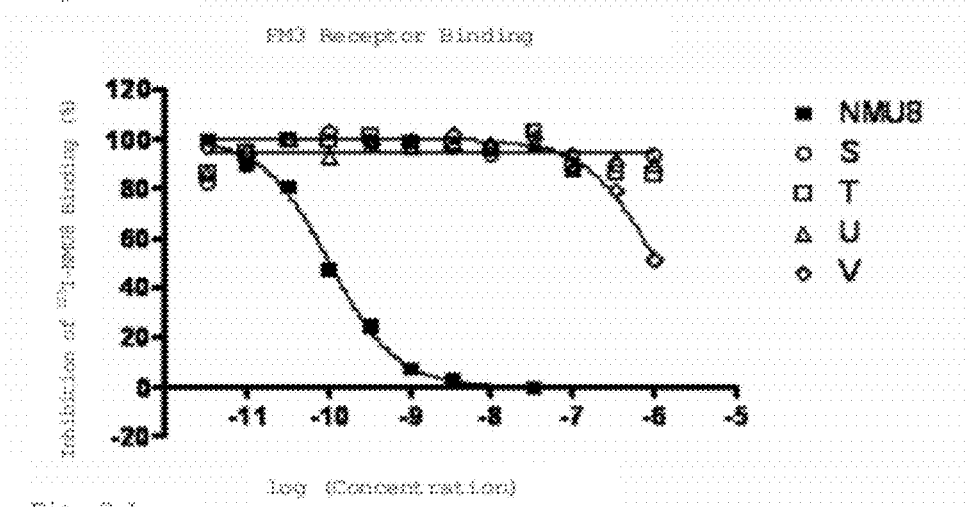
Figures 1, 2:
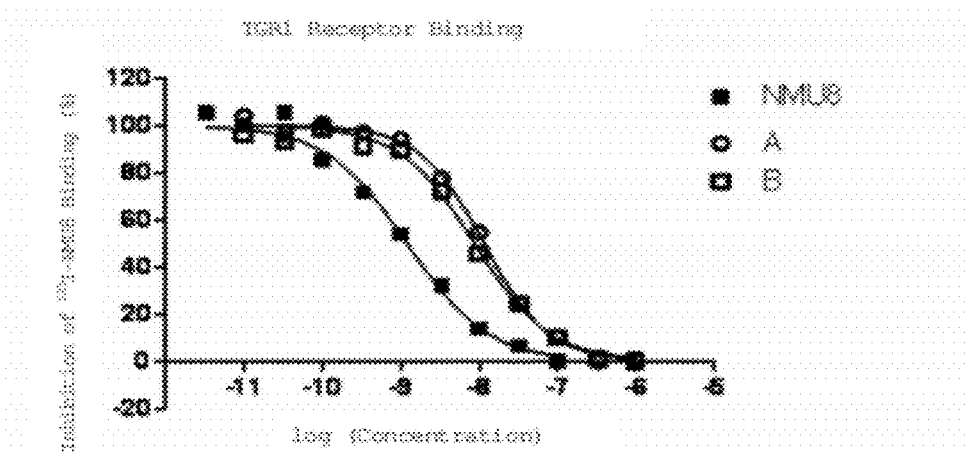
Figure 2:
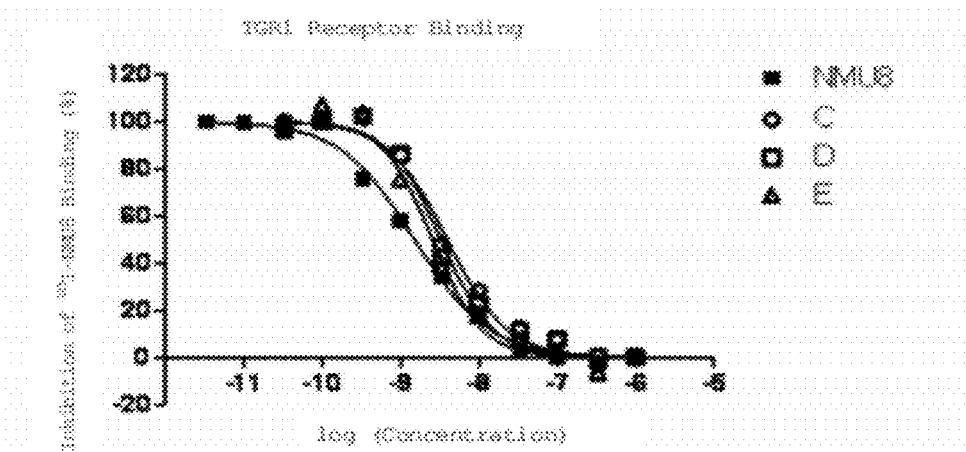
Figures 2, 3:
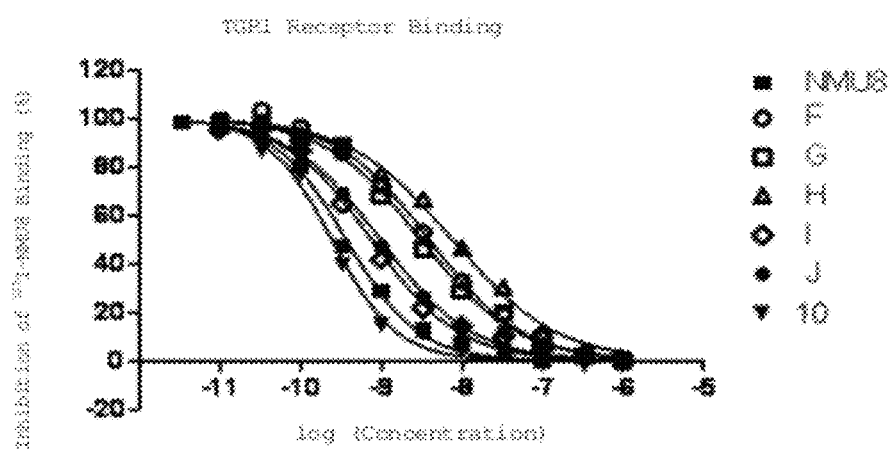
Figures 2, 3, 4:
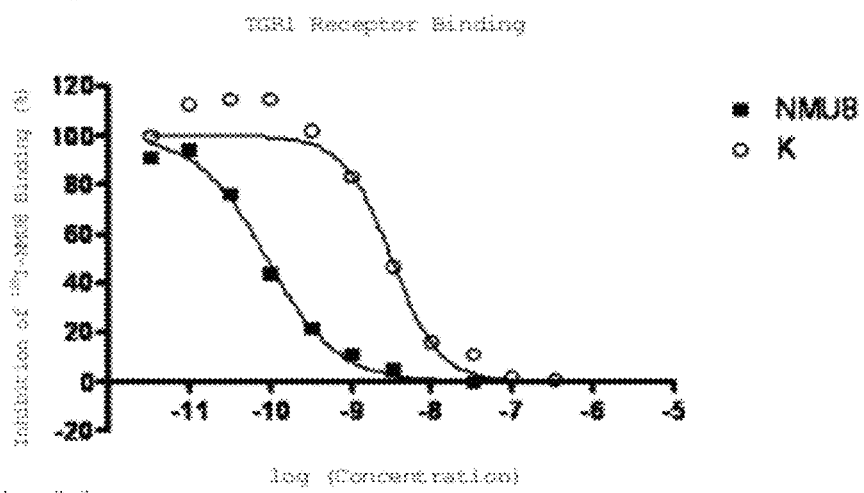
Figures 2, 3, 4, 5:
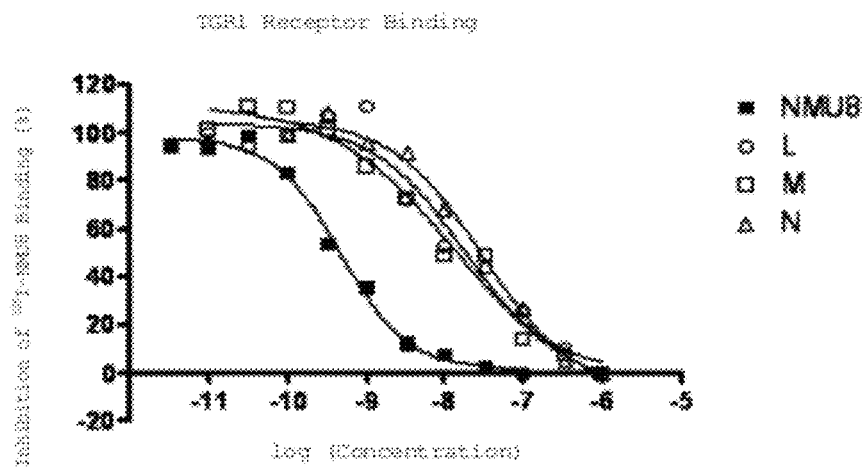
Figures 2, 3, 4, 5, 6:
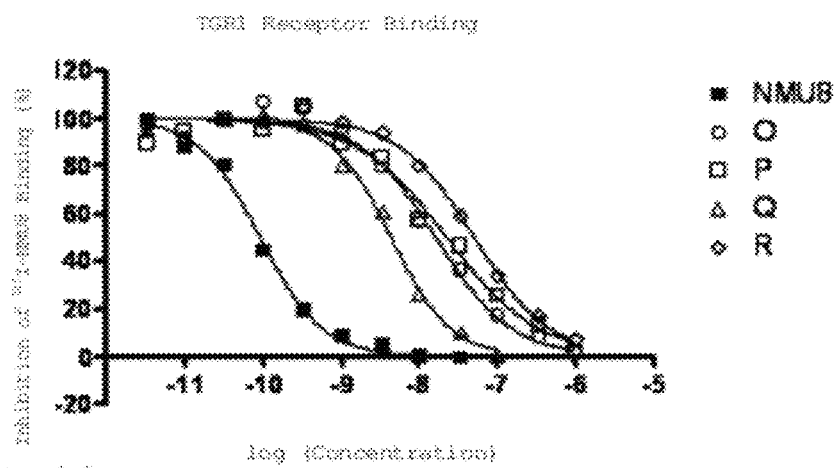
Figures 2, 3, 4, 5, 6, 7:
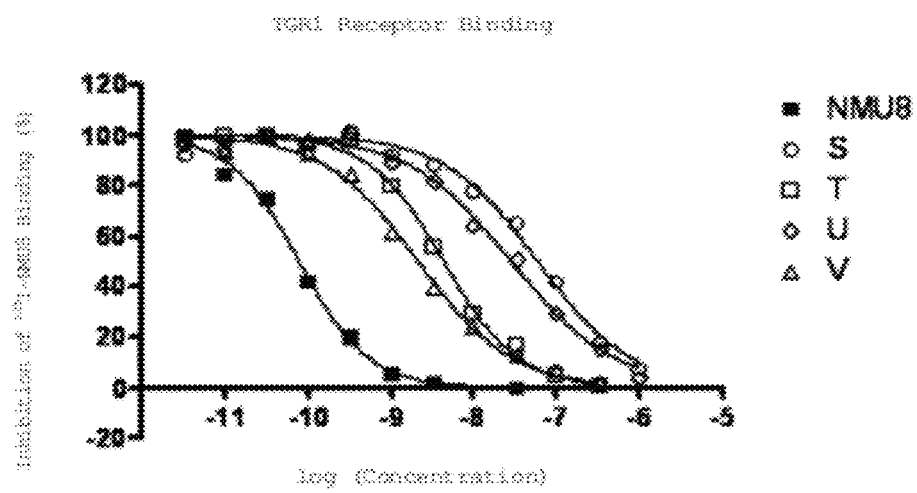
Figure 3:
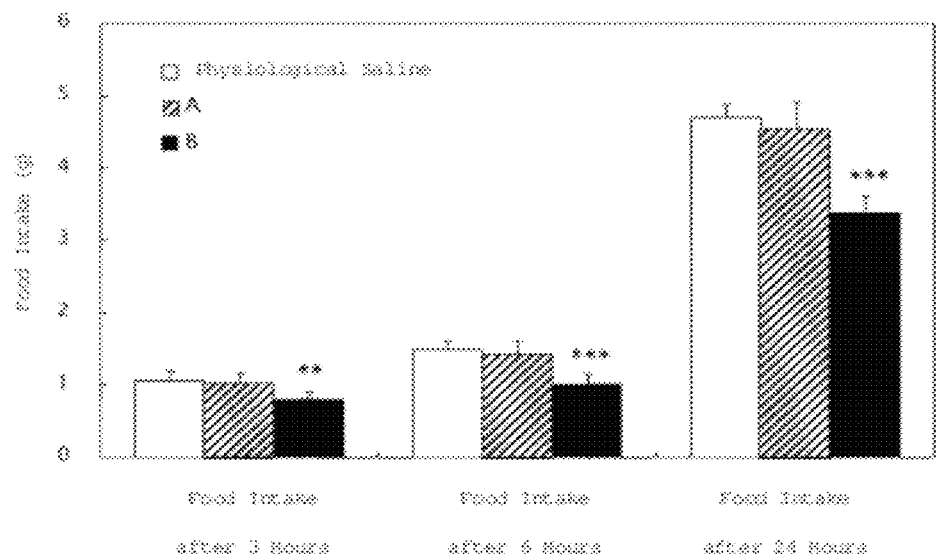
Figure 4:
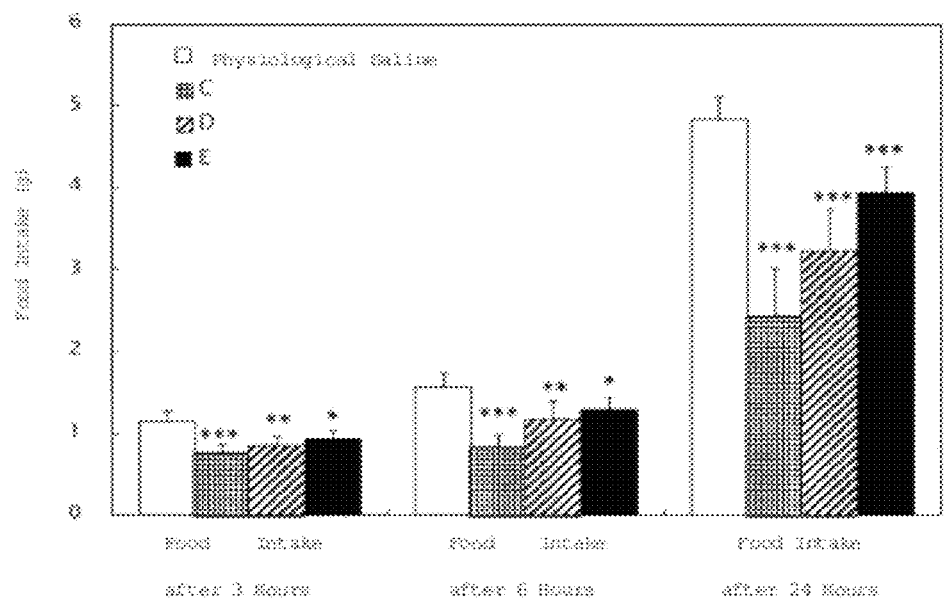
Figure 5:
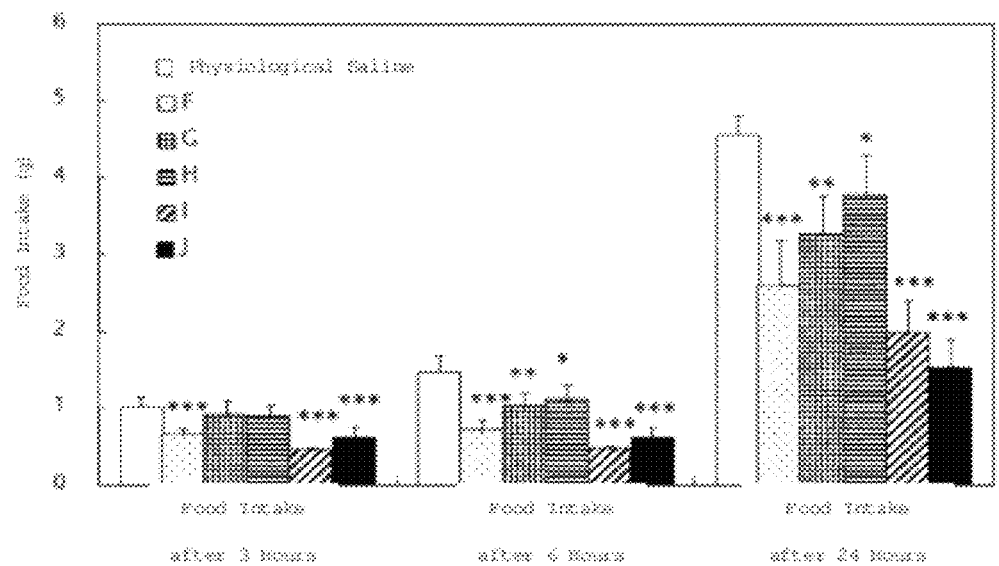
Figure 6:
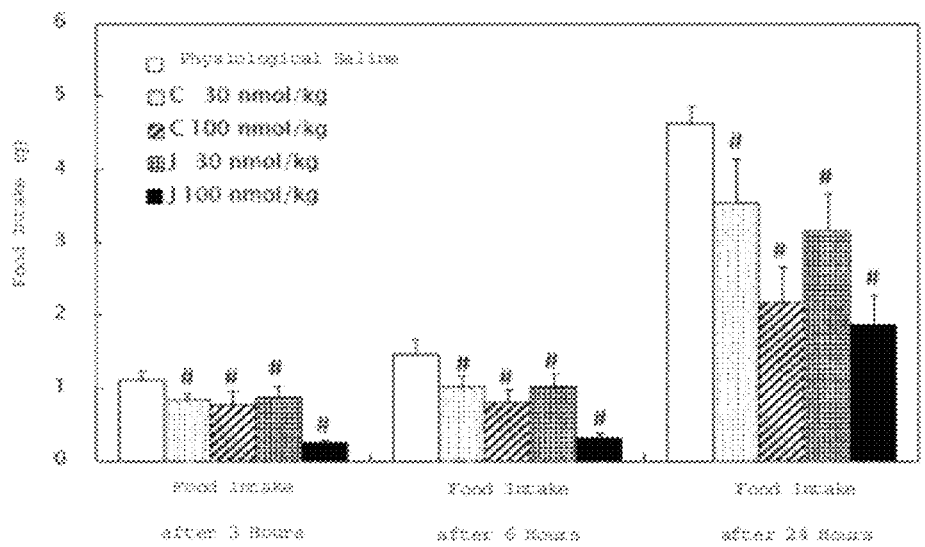
Figure 7:
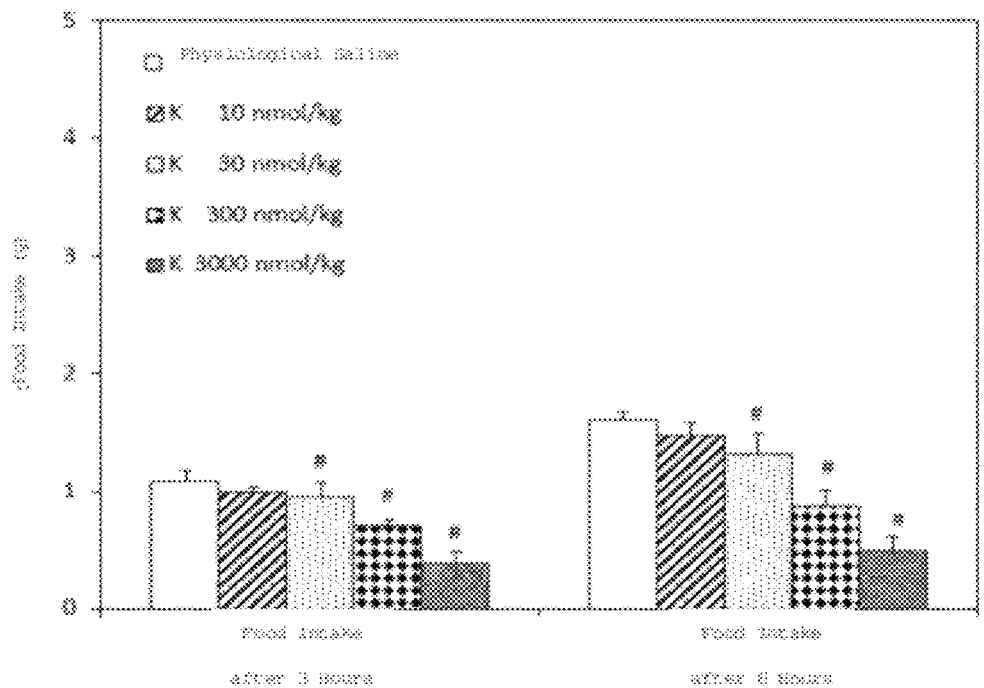

In FIG. 7, the columns represent, from left, physiological saline, Compound K (10 nmol/kg), Compound K (30 nmol/kg), Compound K (300 nmol/kg), and Compound K (3000 nmol/kg). # indicates that the significance level was smaller than 0.025 (P<0.025), based on William's test performed with respect to the feed intakes.

The mice were 10 weeks old with an average weight of 24.5 g, and the number thereof was five to six animals.

Figure 8:
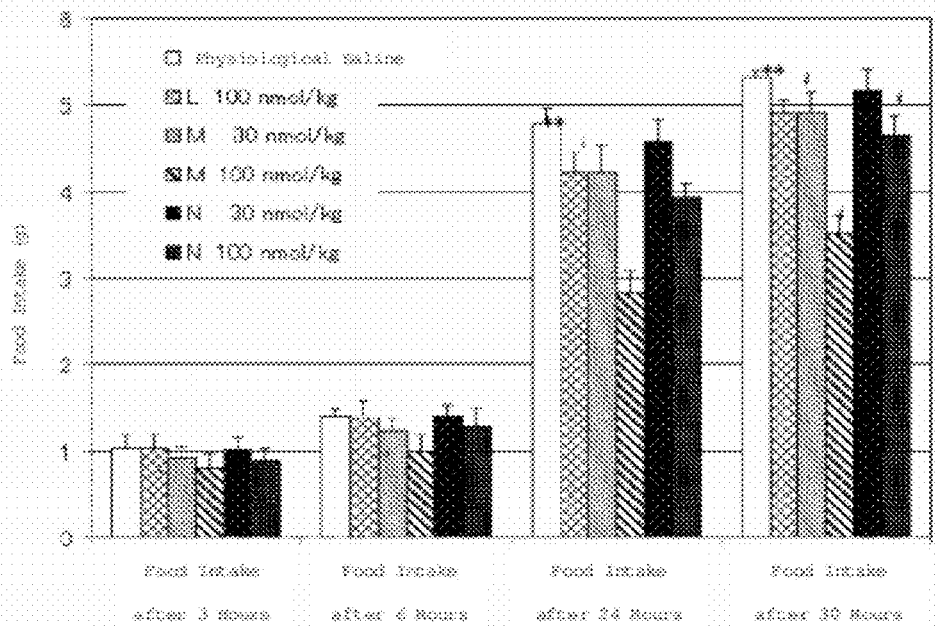
FIG. 8 is a graph showing the change in the food intake in mice when NMU-PEGylated form is subcutaneously administered to mice in a fasting and refeeding test (Compounds L, M, N).

In FIG. 8, the columns represent, from left, physiological saline, Compound L (100 nmol/kg), Compound M (30 nmol/kg), Compound M (100 nmol/kg), Compound N (30 nmol/kg), and Compound N (100 nmol/kg). # indicates that the significance level was smaller than 0.025 (P<0.025), based on William's test performed with respect to the feed intakes. ** indicates that the significance level was smaller than 0.01 (P<0.01), which was determined based on a 2-sample test performed with respect to the feed intake of the Compound L (100 nmol/kg) administration group and the feed intake of the physiological saline group.

The mice were 9 weeks old with an average weight of 23.6 g, and the number was five to six animals.

Figure 9:
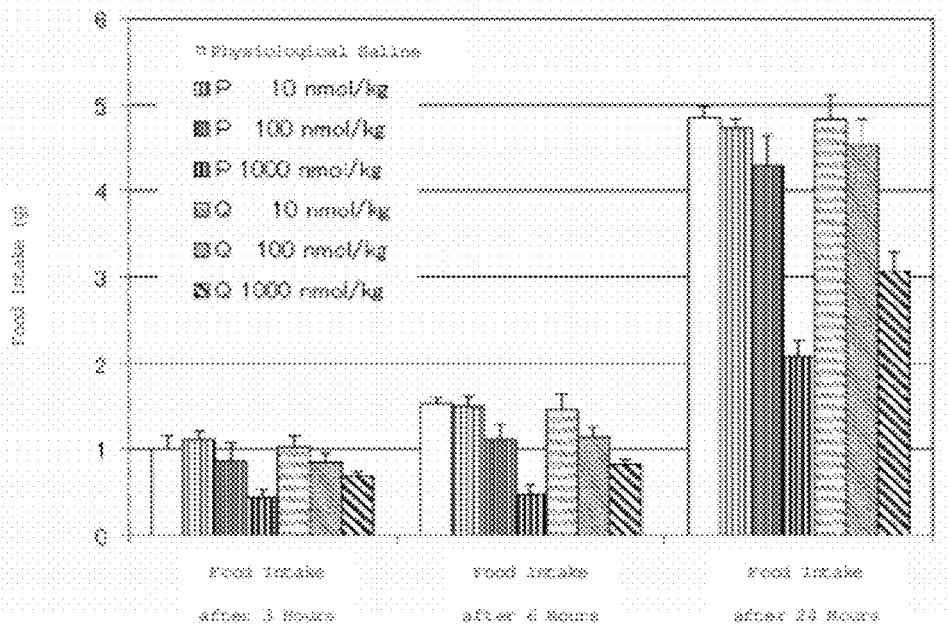
FIG. 9 is a graph showing the change in the food intake in mice when NMU-PEGylated form is subcutaneously administered to mice in a fasting and refeeding test (Compounds P, Q).

In FIG. 9, the columns represent, from left, physiological saline, Compound P (10 nmol/kg), Compound P (100 nmol/kg), Compound P (1000 nmol/kg), Compound Q (10 nmol/kg), Compound Q (100 nmol/kg), and Compound Q (1000 nmol/kg). # indicates that the significance level was smaller than 0.025 (P<0.025), based on William's test performed with respect to the feed intakes.

The mice were 10 weeks old with an average weight of 24.8 g, and the number thereof was five animals.

Figure 10:
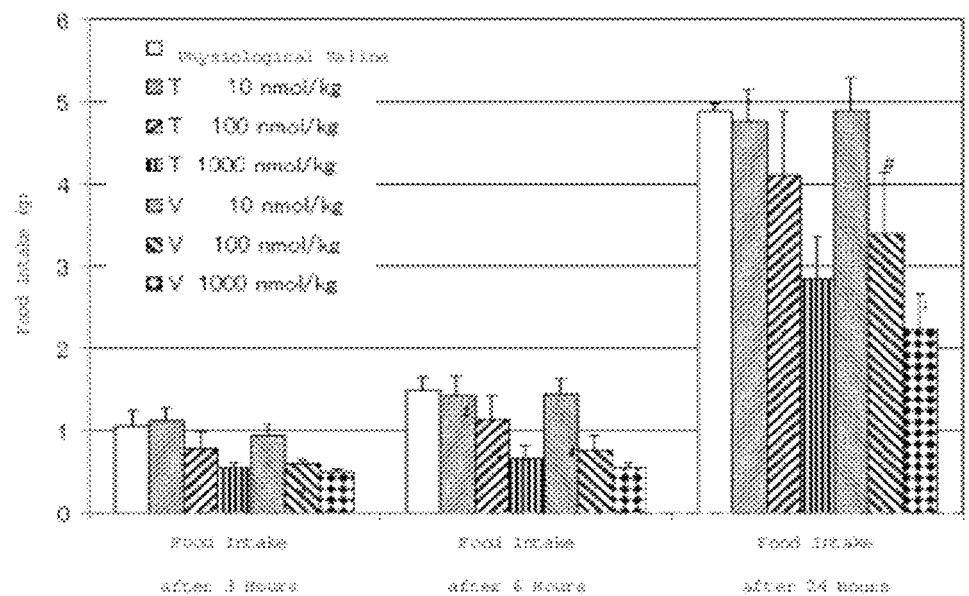
FIG. 10 is a graph showing the change in the food intake in mice when NMU-PEGylated form is subcutaneously administered to mice in a fasting and refeeding test (Compounds T, V).

In FIG. 10, the columns represent, from left, physiological saline, Compound T (10 nmol/kg), Compound T (100 nmol/kg), Compound T (1000 nmol/kg), Compound V (10 nmol/kg), Compound V (100 nmol/kg), and Compound V (1000 nmol/kg). # indicates that the significance level was smaller than 0.025 (P<0.025), based on William's test performed with respect to the feed intakes.

The mice were 10 weeks old with an average weight of 24.8 g, and the number thereof was four to five animals.

Figure 11:
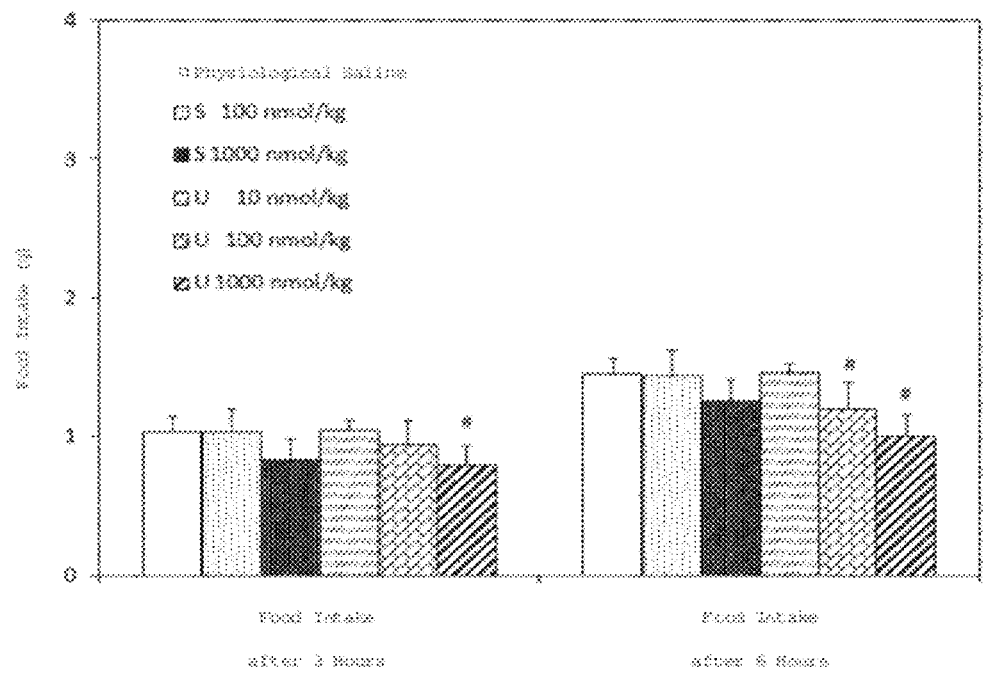
FIG. 11 is a graph showing the change in the food intake in mice when NMU-PEGylated form is subcutaneously administered to mice in a fasting and refeeding test (Compounds S, U).

In FIG. 11, the columns represent, from left, physiological saline, Compound S (100 nmol/kg), Compound S (1000 nmol/kg), Compound U (10 nmol/kg), Compound U (100 nmol/kg), Compound U (1000 nmol/kg), and Compound K (100 nmol/kg). # indicates that the significance level was smaller than 0.025 (P<0.025), based on William's test performed with respect to the feed intakes.

The mice were 10 weeks old with an average weight of 24.6 g, and the number thereof was five animals.

As is clear from FIGS. 7 to 11, the NMU-8-PEG conjugates significantly suppressed food intake in mice.

INDUSTRIAL APPLICABILITY

The compounds of the present invention can be used as an anorectic agent, or as a therapeutic and prophylactic agent for obesity.

Sequence Listing Free Text

[SEQ ID NO.: 2]
  A variant of NMU-8
  Position 8 (C-terminus) is amidated.
[SEQ ID NO.: 3]
  A variant of NMU-8
  Position 8 (C-terminus) is amidated.
[SEQ ID NO.: 4]
  A variant of NMU-8
  Position 8 (C-terminus) is amidated.
[SEQ ID NO.: 5]
  A variant of NMU-8
  Position 8 (C-terminus) is amidated.
[SEQ ID NO.: 6]
  A variant of NMU-8
  Position 8 (C-terminus) is amidated.
  The alanine at position 3 is substituted with cyclohexyl. Therefore, position 3 is β-cyclohexylalanine.
[SEQ ID NO.: 7]
  A variant of NMU-8
  Position 8 (C-terminus) is amidated.
[SEQ ID NO.: 8]
  A variant of NMU-8
  Position 8 (C-terminus) is amidated.
[SEQ ID NO.: 9]
  A variant of NMU-8
  Position 8 (C-terminus) is amidated.
[SEQ ID NO.: 10]
  A variant of NMU-8
  Position 8 (C-terminus) is amidated.
[SEQ ID NO.: 11]
  A variant of NMU-8
  Position 8 (C-terminus) is amidated.
[SEQ ID NO.: 12]
  A variant of NMU-8
  Position 8 (C-terminus) is amidated.
[SEQ ID NO.: 13]
  A variant of NMU-8
  Position 8 (C-terminus) is amidated.
  The arginine at position 7 is substituted with methyl, and position 7 is thus $N^{\alpha}$-methylarginine.
[SEQ ID NO.: 14]
  A variant of NMU-8
  Position 8 (C-terminus) is amidated.
  The leucine at position 3 is substituted with methyl. Therefore, position 3 is $N^{\alpha}$-methylleucine.
  The arginine at position 7 is substituted with methyl, and position 7 is thus $N^{\omega}$-methylarginine.

[SEQ ID NO.: 15]
A variant of NMU-8
Position 8 (C-terminus) is amidated.
The tyrosine at position 1 is substituted with methyl. Therefore, position 1 is N$^\alpha$-methyltyrosine.
The leucine at position 3 is substituted with methyl. Therefore, position 3 is N$^\alpha$-methylleucine.
The arginine at position 5 is substituted with methyl. Therefore, position 5 is N$^\alpha$-methylarginine.

[SEQ ID NO.: 16]
A variant of NMU-8
Position 8 (C-terminus) is amidated.
Position 6 is N$^\alpha$-methylalanine.

[SEQ ID NO.: 17]
A variant of NMU-8
Position 8 (C-terminus) is amidated.
Position 6 is N$^\alpha$-methylalanine.

[SEQ ID NO.: 18]
A variant of NMU-8
Position 8 (C-terminus) is amidated.

[SEQ ID NO.: 19]
A variant of NMU-8
Position 8 (C-terminus) is amidated.

[SEQ ID NO.: 20]
A variant of NMU-8
Position 8 (C-terminus) is amidated.
Position 2 is 2-naphtylalanine.
Position 6 is N$^\alpha$-methylalanine.

The invention claimed is:
1. A compound represented by formula
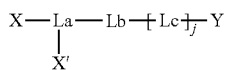  (I)
wherein Y represents a polypeptide consisting of an amino acid sequence set forth in SEQ ID NO.: 1 wherein 1 to 5. The compound of claim 1 or a salt thereof, wherein Lc is a divalent group represented by formula (ii):

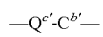

wherein $Q^{c'}$ is a divalent group represented by formula:

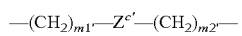

wherein m1' is an integer of 0 to 15, $Z^{c'}$ represents

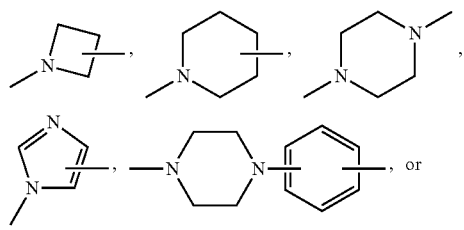

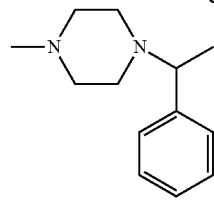

and m2' is an integer of 0 to 15, and
$C^{b'}$ represents a bond, —CO— or —SO$_2$—.

6. An anorectic agent comprising the compound of claim 1 or a salt thereof.

7. An agent for treating obesity comprising the compound of claim 1 or a salt thereof.

8. A method for treating obesity in a mammal, comprising administering the compound of claim 1 or a salt thereof to the mammal.

9. A compound wherein the amino acid sequence consists of SEQ ID No. 20: PEG20k-NpipAc-Tyr-Nal(2)-Leu-Phe-Arg-NMeAla-Arg-Asn-NH$_2$ or a salt thereof.

* * * * *

SEQUENCE LISTING

```
<160> NUMBER OF SEQ ID NOS: 20

<210> SEQ ID NO 1
<211> LENGTH: 8
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: AMIDATION

<400> SEQUENCE: 1

Tyr Phe Leu Phe Arg Pro Arg Asn
1               5

<210> SEQ ID NO 2
<211> LENGTH: 8
<212> TYPE: PRT
<213> ORGANISM: Artificial Sequence
<220> FEATURE:
<223> OTHER INFORMATION: variant NMU-8
<220> FEATURE:
<221> NAME/KEY: MOD_RES
<222> LOCATION: (8)..(8)
<223> OTHER INFORMATION: AMIDATION

<400> SEQUENCE: 2

Tyr Phe Leu Phe Gln Pro Arg Asn
1               5

<210> SEQ ID NO 3
<211> LENGTH: 8
<212> TYPE: PRT
<213> ORGANISM: Artificial Sequence
<220> FEATURE:
<223> OTHER INFORMATION: variant NMU-8

<400> SEQUENCE: 3

Tyr Phe Gln Phe Arg Pro Arg Asn
1               5

<210> SEQ ID NO 4
<211> LENGTH: 8
<212> TYPE: PRT
<213> ORGANISM: Artificial Sequence
<220> FEATURE:
<223> OTHER INFORMATION: variant NMU-8
<220> FEATURE:
<221> NAME/KEY: MOD_RES
<222> LOCATION: (8)..(8)
<223> OTHER INFORMATION: AMIDATION

<400> SEQUENCE: 4
```

```
Tyr Phe Arg Phe Arg Pro Arg Asn
1               5

<210> SEQ ID NO 5
<211> LENGTH: 8
<212> TYPE: PRT
<213> ORGANISM: Artificial Sequence
<220> FEATURE:
<223> OTHER INFORMATION: variant NMU-8

<400> SEQUENCE: 5

Tyr Phe Val Phe Arg Pro Arg Asn
1               5

<210> SEQ ID NO 6
<211> LENGTH: 8
<212> TYPE: PRT
<213> ORGANISM: Artificial Sequence
<220> FEATURE:
<223> OTHER INFORMATION: variant NMU-8
<220> FEATURE:
<221> NAME/KEY: MOD_RES
<222> LOCATION: (8)..(8)
<223> OTHER INFORMATION: AMIDATION

<400> SEQUENCE: 6

Tyr Tyr Leu Phe Arg Pro Arg Asn
1               5

<210> SEQ ID NO 7
<211> LENGTH: 8
<212> TYPE: PRT
<213> ORGANISM: Artificial Sequence
<220> FEATURE:
<223> OTHER INFORMATION: variant NMU-8
<220> FEATURE:
<221> NAME/KEY: misc_feature
<222> LOCATION: (3)..(3)
<223> OTHER INFORMATION: The alanine is substituted by cyclohexyl.
<220> FEATURE:
<221> NAME/KEY: MOD_RES
<222> LOCATION: (8)..(8)
<223> OTHER INFORMATION: AMIDATION

<400> SEQUENCE: 7

Tyr Phe Ala Phe Arg Pro Arg Asn
1               5

<210> SEQ ID NO 8
<211> LENGTH: 8
<212> TYPE: PRT
<213> ORGANISM: Artificial Sequence
<220> FEATURE:
<223> OTHER INFORMATION: variant NMU-8
<220> FEATURE:
<221> NAME/KEY: MOD_RES
<222> LOCATION: (8)..(8)
<223> OTHER INFORMATION: AMIDATION

<400> SEQUENCE: 8

Arg Phe Leu Phe Arg Pro Arg Asn
1               5

<210> SEQ ID NO 9
<211> LENGTH: 8
<212> TYPE: PRT
<213> ORGANISM: Artificial Sequence
<220> FEATURE:
<223> OTHER INFORMATION: variant NMU-8
<220> FEATURE:
```

```
<221> NAME/KEY: MOD_RES
<222> LOCATION: (8)..(8)
<223> OTHER INFORMATION: AMIDATION

<400> SEQUENCE: 9

Pro Phe Leu Phe Arg Pro Arg Asn
1               5

<210> SEQ ID NO 10
<211> LENGTH: 8
<212> TYPE: PRT
<213> ORGANISM: Artificial Sequence
<220> FEATURE:
<223> OTHER INFORMATION: variant NMU-8
<220> FEATURE:
<221> NAME/KEY: MOD_RES
<222> LOCATION: (8)..(8)
<223> OTHER INFORMATION: AMIDATION

<400> SEQUENCE: 10

Phe Trp Leu Phe Arg Ala Arg Asn
1               5

<210> SEQ ID NO 11
<211> LENGTH: 8
<212> TYPE: PRT
<213> ORGANISM: Artificial Sequence
<220> FEATURE:
<223> OTHER INFORMATION: variant NMU-8
<220> FEATURE:
<221> NAME/KEY: MOD_RES
<222> LOCATION: (8)..(8)
<223> OTHER INFORMATION: AMIDATION

<400> SEQUENCE: 11

Tyr Phe Leu Phe Arg Pro Arg Asp
1               5

<210> SEQ ID NO 12
<211> LENGTH: 8
<212> TYPE: PRT
<213> ORGANISM: Artificial Sequence
<220> FEATURE:
<223> OTHER INFORMATION: variant NMU-8
<220> FEATURE:
<221> NAME/KEY: misc_feature
<222> LOCATION: (5)..(5)
<223> OTHER INFORMATION: Xaa is N(alpha)-methyl arginine.
<220> FEATURE:
<221> NAME/KEY: MOD_RES
<222> LOCATION: (8)..(8)
<223> OTHER INFORMATION: AMIDATION

<400> SEQUENCE: 12

Tyr Phe Leu Phe Xaa Pro Arg Asn
1               5

<210> SEQ ID NO 13
<211> LENGTH: 8
<212> TYPE: PRT
<213> ORGANISM: Artificial Sequence
<220> FEATURE:
<223> OTHER INFORMATION: variant NMU-8
<220> FEATURE:
<221> NAME/KEY: MOD_RES
<222> LOCATION: (7)..(7)
<223> OTHER INFORMATION: METHYLATION
<220> FEATURE:
<221> NAME/KEY: MOD_RES
<222> LOCATION: (8)..(8)
<223> OTHER INFORMATION: AMIDATION
```

```
<400> SEQUENCE: 13

Tyr Phe Leu Phe Arg Pro Arg Asn
1               5

<210> SEQ ID NO 14
<211> LENGTH: 8
<212> TYPE: PRT
<213> ORGANISM: Artificial Sequence
<220> FEATURE:
<223> OTHER INFORMATION: variant NMU-8
<220> FEATURE:
<221> NAME/KEY: misc_feature
<222> LOCATION: (3)..(3)
<223> OTHER INFORMATION: Xaa is N(alpha)-methyl leucine.
<220> FEATURE:
<221> NAME/KEY: misc_feature
<222> LOCATION: (7)..(7)
<223> OTHER INFORMATION: Xaa is N(alpha)-methyl arginine.
<220> FEATURE:
<221> NAME/KEY: MOD_RES
<222> LOCATION: (8)..(8)
<223> OTHER INFORMATION: AMIDATION

<400> SEQUENCE: 14

Tyr Phe Xaa Phe Arg Pro Xaa Asn
1               5

<210> SEQ ID NO 15
<211> LENGTH: 8
<212> TYPE: PRT
<213> ORGANISM: Artificial Sequence
<220> FEATURE:
<223> OTHER INFORMATION: variant NMU-8
<220> FEATURE:
<221> NAME/KEY: misc_feature
<222> LOCATION: (1)..(1)
<223> OTHER INFORMATION: Xaa is N(alpha)-methyl tyrosine.
<220> FEATURE:
<221> NAME/KEY: misc_feature
<222> LOCATION: (3)..(3)
<223> OTHER INFORMATION: Xaa is N(alpha)-methyl leucine.
<220> FEATURE:
<221> NAME/KEY: misc_feature
<222> LOCATION: (5)..(5)
<223> OTHER INFORMATION: Xaa is N(alpha)-methyl arginine.
<220> FEATURE:
<221> NAME/KEY: MOD_RES
<222> LOCATION: (8)..(8)
<223> OTHER INFORMATION: AMIDATION

<400> SEQUENCE: 15

Xaa Phe Xaa Phe Xaa Pro Arg Asn
1               5

<210> SEQ ID NO 16
<211> LENGTH: 8
<212> TYPE: PRT
<213> ORGANISM: Artificial Sequence
<220> FEATURE:
<223> OTHER INFORMATION: variant NMU-8
<220> FEATURE:
<221> NAME/KEY: misc_feature
<222> LOCATION: (6)..(6)
<223> OTHER INFORMATION: Xaa is N(alpha)-methyl alanine.
<220> FEATURE:
<221> NAME/KEY: MOD_RES
<222> LOCATION: (8)..(8)
<223> OTHER INFORMATION: AMIDATION

<400> SEQUENCE: 16

Tyr Trp Leu Phe Arg Xaa Arg Asn
```

```
<210> SEQ ID NO 17
<211> LENGTH: 8
<212> TYPE: PRT
<213> ORGANISM: Artificial Sequence
<220> FEATURE:
<223> OTHER INFORMATION: variant NMU-8
<220> FEATURE:
<221> NAME/KEY: misc_feature
<222> LOCATION: (6)..(6)
<223> OTHER INFORMATION: Xaa is N(alpha)-methyl alanine.
<220> FEATURE:
<221> NAME/KEY: MOD_RES
<222> LOCATION: (8)..(8)
<223> OTHER INFORMATION: AMIDATION

<400> SEQUENCE: 17

Tyr Glu Leu Phe Arg Xaa Arg Asn
1               5

<210> SEQ ID NO 18
<211> LENGTH: 8
<212> TYPE: PRT
<213> ORGANISM: Artificial Sequence
<220> FEATURE:
<223> OTHER INFORMATION: variant NMU-8
<220> FEATURE:
<221> NAME/KEY: MOD_RES
<222> LOCATION: (8)..(8)
<223> OTHER INFORMATION: AMIDATION

<400> SEQUENCE: 18

Tyr Glu Leu Phe Arg Ala Arg Asn
1               5

<210> SEQ ID NO 19
<211> LENGTH: 8
<212> TYPE: PRT
<213> ORGANISM: Artificial Sequence
<220> FEATURE:
<223> OTHER INFORMATION: variant NMU-8
<220> FEATURE:
<221> NAME/KEY: MOD_RES
<222> LOCATION: (8)..(8)
<223> OTHER INFORMATION: AMIDATION

<400> SEQUENCE: 19

Tyr Trp Leu Phe Arg Ala Arg Asn
1               5

<210> SEQ ID NO 20
<211> LENGTH: 8
<212> TYPE: PRT
<213> ORGANISM: Artificial Sequence
<220> FEATURE:
<223> OTHER INFORMATION: variant NMU-8
<220> FEATURE:
<221> NAME/KEY: misc_feature
<222> LOCATION: (2)..(2)
<223> OTHER INFORMATION: Xaa is 2-naphtylalanine.
<220> FEATURE:
<221> NAME/KEY: misc_feature
<222> LOCATION: (6)..(6)
<223> OTHER INFORMATION: Xaa is N(alpha)-methyl alanine.
<220> FEATURE:
<221> NAME/KEY: MOD_RES
<222> LOCATION: (8)..(8)
<223> OTHER INFORMATION: AMIDATION
```

```
<400> SEQUENCE: 20
Tyr Xaa Leu Phe Arg Xaa Arg Asn
1               5
```